(12) United States Patent
Nakamura et al.

(10) Patent No.: US 6,921,655 B1
(45) Date of Patent: Jul. 26, 2005

(54) ENDOGLUCANASES AND CELLULASE PREPARATIONS CONTAINING THE SAME

(75) Inventors: Yuko Nakamura, Saitama (JP); Tatsuki Moriya, Kanagawa (JP); Yuko Baba, Saitama (JP); Koji Yanai, Kanagawa (JP); Naomi Sumida, Kanagawa (JP); Tomoko Nishimura, Saitama (JP); Kouichirou Murashima, Saitama (JP); Akitaka Nakane, Saitama (JP); Takashi Yaguchi, Kanagawa (JP); Jinichiro Koga, Saitama (JP); Takeshi Murakami, Kanagawa (JP); Toshiaki Kono, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/807,933
(22) PCT Filed: Oct. 25, 1999
(86) PCT No.: PCT/JP99/05884
§ 371 (c)(1),
(2), (4) Date: Apr. 20, 2001
(87) PCT Pub. No.: WO00/24879
PCT Pub. Date: May 4, 2000

(30) Foreign Application Priority Data

Oct. 23, 1998 (JP) .......................... 10/302387

(51) Int. Cl.⁷ .......................... C12P 21/06; C12N 9/00; C12N 9/24; C07H 21/04
(52) U.S. Cl. .............. 435/200; 435/4; 435/6; 435/69.1; 435/183; 435/192; 435/252.3; 435/320.1; 510/114; 510/392; 510/515; 536/23.2; 536/23.7
(58) Field of Search .............. 435/4, 6, 69.1, 435/183, 192, 200, 252.3, 320.1; 510/114, 392, 515; 536/23.2–23.7, 23.74

(56) References Cited

U.S. PATENT DOCUMENTS 4,966,850 A * 10/1990 Yu et al. .................... 435/200
6,387,690 B1 * 5/2002 Schulein et al. ............ 435/200

FOREIGN PATENT DOCUMENTS

| EP | 0 633 311 A | 1/1995 |
|---|---|---|
| EP | 0 843 041 A | 5/1998 |
| WO | WO 94/07998 * | 4/1994 |
| WO | 96/29397 | 9/1996 |
| WO | 97/43409 | 11/1997 |
| WO | 98/12307 | 3/1998 |
| WO | WO 00 20555 A | 4/2000 |

OTHER PUBLICATIONS

Somkuti (J. Gen. Microbiol., 1974, vol. 81, pp. 1–6).*

Saloheimo Anu et al., "A novel, small endoglucanase gene, egl5, from *Trichoderma reesei* isolated by expression in yeast," Molecular Microbiology (1994), vol. 13, No. 2, pp. 219–228.

Theberge, M. et al.: "Purification and Characterization of an Endoglucanase from *Streptomyces lividans* 66 and DNA Sequence of the Gene" in Applied and Environmental Microbiology, Washington, DC., US, vol. 58, No. 3, Mar. 1992, pp. 815–820, XP002102200, ISSN: 0099–2240.

Moriya Tatsuki et al.: "Molecular cloning of endo–beta–D–1,4–glucanase genes, rce1, rce2, and rce3, from *Rhizopus oryzae*." in Journal of Bacteriology, vol. 185, No. 5, Mar. 2003 pp. 1749–1756, XP002269183, ISN: 0021–9193.

* cited by examiner

Primary Examiner—Manjunath Rao
(74) Attorney, Agent, or Firm—Varndell & Varndell, PLLC

(57) ABSTRACT

It is an object of the present invention to provide enzymes that have high endoglucanase activity and yet exhibit high activity even under alkaline conditions, and genes encoding the same. The enzyme according to the invention has the following properties: a) exhibiting endoglucanase activity; and b) capable of completely removing fuzz from regenerated cellulose fabrics at a concentration of 1 mg of the protein/L or below. The enzyme of the invention having endoglucanase activity is a protein comprising the amino acid sequence as shown in SEQ ID NO: 1, 3, 5, 7, 9 or 11; a modified protein thereof exhibiting endoglucanase activity; or a homologue of the protein or the modified protein.

28 Claims, 3 Drawing Sheets

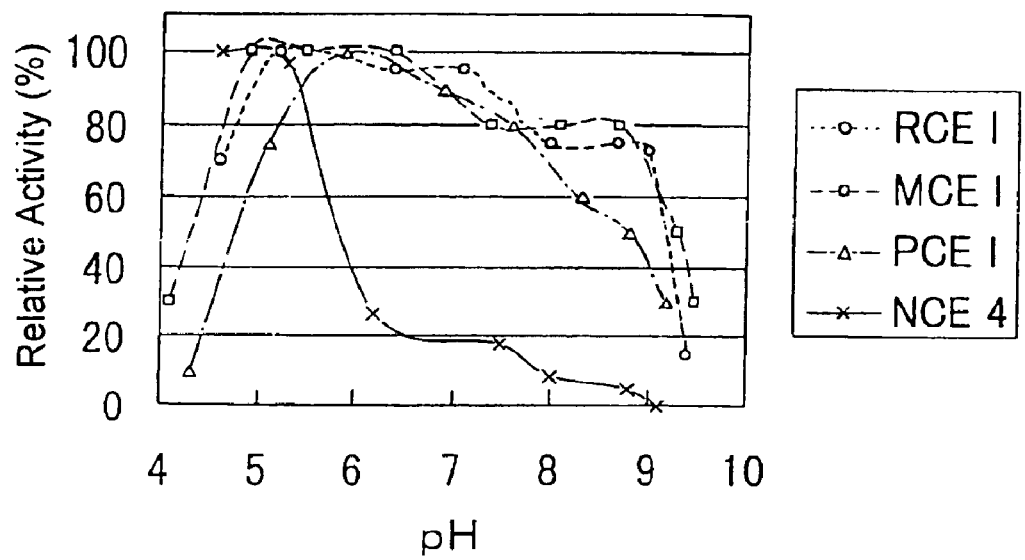
F I G. 1
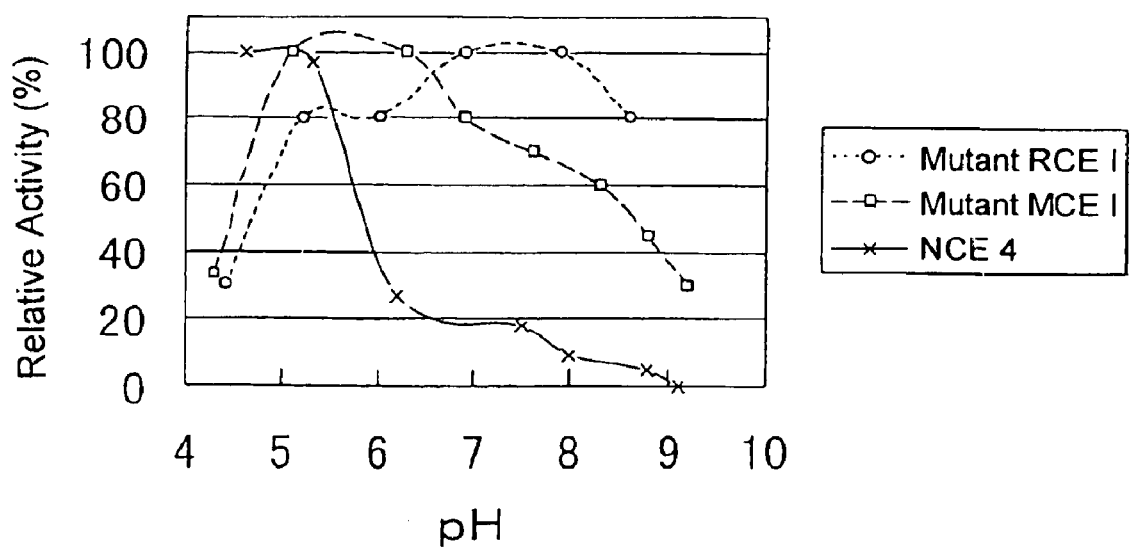
F I G. 2

| Codon | Count | Codon | Count | Codon | Count | Codon | Count |
|---|---|---|---|---|---|---|---|
| TTT-Phe | 2 | TCT-Ser | 24 | TAT-Tyr | 4 | TGT-Cys | 20 |
| TTC-Phe | 6 | TCC-Ser | 9 | TAC-Tyr | 8 | TGC-Cys | 6 |
| TTA-Leu | 0 | TCA-Ser | 2 | TAA-*** | 1 | TGA-*** | 0 |
| TTG-Leu | 3 | TCG-Ser | 1 | TAG-*** | 0 | TGG-Trp | 10 |
| CTT-Leu | 8 | CCT-Pro | 7 | CAT-His | 1 | CGT-Arg | 1 |
| CTC-Leu | 3 | CCC-Pro | 5 | CAC-His | 1 | CGC-Arg | 1 |
| CTA-Leu | 0 | CCA-Pro | 1 | CAA-Gln | 9 | CGA-Arg | 0 |
| CTG-Leu | 1 | CCG-Pro | 0 | CAG-Gln | 1 | CGG-Arg | 0 |
| ATT-Ile | 6 | ACT-Thr | 19 | AAT-Asn | 10 | AGT-Ser | 6 |
| ATC-Ile | 3 | ACC-Thr | 7 | AAC-Asn | 16 | AGC-Ser | 11 |
| ATA-Ile | 0 | ACA-Thr | 2 | AAA-Lys | 10 | AGA-Arg | 3 |
| ATG-Met | 6 | ACG-Thr | 1 | AAG-Lys | 17 | AGG-Arg | 0 |
| GTT-Val | 4 | GCT-Ala | 17 | GAT-Asp | 7 | GGT-Gly | 34 |
| GTC-Val | 7 | GCC-Ala | 12 | GAC-Asp | 7 | GGC-Gly | 8 |
| GTA-Val | 3 | GCA-Ala | 2 | GAA-Glu | 12 | GGA-Gly | 2 |
| GTG-Val | 0 | GCG-Ala | 0 | GAG-Glu | 0 | GGG-Gly | 0 |

FIG. 3

| Codon | Count | Codon | Count | Codon | Count | Codon | Count |
|---|---|---|---|---|---|---|---|
| TTT-Phe | 0 | TCT-Ser | 2 | TAT-Tyr | 4 | TGT-Cys | 0 |
| TTC-Phe | 19 | TCC-Ser | 9 | TAC-Tyr | 18 | TGC-Cys | 18 |
| TTA-Leu | 0 | TCA-Ser | 0 | TAA-*** | 1 | TGA-*** | 0 |
| TTG-Leu | 0 | TCG-Ser | 7 | TAG-*** | 0 | TGG-Trp | 10 |
| CTT-Leu | 1 | CCT-Pro | 3 | CAT-His | 0 | CGT-Arg | 4 |
| CTC-Leu | 13 | CCC-Pro | 13 | CAC-His | 7 | CGC-Arg | 13 |
| CTA-Leu | 0 | CCA-Pro | 0 | CAA-Gln | 1 | CGA-Arg | 0 |
| CTG-Leu | 8 | CCG-Pro | 8 | CAG-Gln | 17 | CGG-Arg | 0 |
| ATT-Ile | 3 | ACT-Thr | 0 | AAT-Asn | 1 | AGT-Ser | 0 |
| ATC-Ile | 13 | ACC-Thr | 25 | AAC-Asn | 33 | AGC-Ser | 12 |
| ATA-Ile | 0 | ACA-Thr | 0 | AAA-Lys | 0 | AGA-Arg | 0 |
| ATG-Met | 12 | ACG-Thr | 2 | AAG-Lys | 17 | AGG-Arg | 4 |
| GTT-Val | 3 | GCT-Ala | 10 | GAT-Asp | 8 | GGT-Gly | 12 |
| GTC-Val | 19 | GCC-Ala | 29 | GAC-Asp | 19 | GGC-Gly | 30 |
| GTA-Val | 0 | GCA-Ala | 0 | GAA-Glu | 0 | GGA-Gly | 0 |
| GTG-Val | 2 | GCG-Ala | 2 | GAG-Glu | 20 | GGG-Gly | 0 |

FIG. 4

| Codon | Count | Codon | Count | Codon | Count | Codon | Count |
|---|---|---|---|---|---|---|---|
| TTT-Phe | 2 | TCT-Ser | 3 | TAT-Tyr | 2 | TGT-Cys | 1 |
| TTC-Phe | 14 | TCC-Ser | 2 | TAC-Tyr | 18 | TGC-Cys | 10 |
| TTA-Leu | 1 | TCA-Ser | 0 | TAA-*** | 0 | TGA-*** | 1 |
| TTG-Leu | 3 | TCG-Ser | 14 | TAG-*** | 0 | TGG-Trp | 12 |
| CTT-Leu | 4 | CCT-Pro | 6 | CAT-His | 0 | CGT-Arg | 1 |
| CTC-Leu | 16 | CCC-Pro | 15 | CAC-His | 7 | CGC-Arg | 16 |
| CTA-Leu | 0 | CCA-Pro | 0 | CAA-Gln | 2 | CGA-Arg | 0 |
| CTG-Leu | 3 | CCG-Pro | 11 | CAG-Gln | 19 | CGG-Arg | 2 |
| ATT-Ile | 5 | ACT-Thr | 7 | AAT-Asn | 4 | AGT-Ser | 0 |
| ATC-Ile | 16 | ACC-Thr | 30 | AAC-Asn | 25 | AGC-Ser | 11 |
| ATA-Ile | 0 | ACA-Thr | 0 | AAA-Lys | 0 | AGA-Arg | 0 |
| ATG-Met | 6 | ACG-Thr | 6 | AAG-Lys | 12 | AGG-Arg | 2 |
| GTT-Val | 4 | GCT-Ala | 13 | GAT-Asp | 2 | GGT-Gly | 12 |
| GTC-Val | 20 | GCC-Ala | 45 | GAC-Asp | 17 | GGC-Gly | 24 |
| GTA-Val | 0 | GCA-Ala | 0 | GAA-Glu | 1 | GGA-Gly | 1 |
| GTG-Val | 2 | GCG-Ala | 7 | GAG-Glu | 20 | GGG-Gly | 0 |

FIG. 5

| Codon | Count | Codon | Count | Codon | Count | Codon | Count |
|---|---|---|---|---|---|---|---|
| TTT-Phe | 1 | TCT-Ser | 2 | TAT-Tyr | 0 | TGT-Cys | 0 |
| TTC-Phe | 15 | TCC-Ser | 12 | TAC-Tyr | 6 | TGC-Cys | 20 |
| TTA-Leu | 0 | TCA-Ser | 0 | TAA-*** | 0 | TGA-*** | 0 |
| TTG-Leu | 1 | TCG-Ser | 4 | TAG-*** | 1 | TGG-Trp | 9 |
| CTT-Leu | 2 | CCT-Pro | 7 | CAT-His | 1 | CGT-Arg | 3 |
| CTC-Leu | 7 | CCC-Pro | 9 | CAC-His | 1 | CGC-Arg | 7 |
| CTA-Leu | 0 | CCA-Pro | 2 | CAA-Gln | 1 | CGA-Arg | 0 |
| CTG-Leu | 3 | CCG-Pro | 6 | CAG-Gln | 12 | CGG-Arg | 1 |
| ATT-Ile | 2 | ACT-Thr | 5 | AAT-Asn | 3 | AGT-Ser | 1 |
| ATC-Ile | 4 | ACC-Thr | 17 | AAC-Asn | 11 | AGC-Ser | 13 |
| ATA-Ile | 0 | ACA-Thr | 1 | AAA-Lys | 0 | AGA-Arg | 0 |
| ATG-Met | 2 | ACG-Thr | 2 | AAG-Lys | 10 | AGG-Arg | 1 |
| GTT-Val | 2 | GCT-Ala | 9 | GAT-Asp | 4 | GGT-Gly | 5 |
| GTC-Val | 11 | GCC-Ala | 17 | GAC-Asp | 13 | GGC-Gly | 26 |
| GTA-Val | 0 | GCA-Ala | 0 | GAA-Glu | 0 | GGA-Gly | 2 |
| GTG-Val | 4 | GCG-Ala | 2 | GAG-Glu | 6 | GGG-Gly | 0 |

FIG. 6

ENDOGLUCANASES AND CELLULASE PREPARATIONS CONTAINING THE SAME

CROSS-REFERENCE TO RELATED APPLICATION

This application is a U.S. national phase application of International Application No. PCT/JP99/05884 filed Oct. 25, 1999, which application was not published in English.

BACKGROUND OF THE INVENTION

1. Field of the Invention

The present invention relates to endoglucanases and cellulase preparations containing the same, as well as methods of treating cellulose-containing fabrics, papers, pulps or animal feeds with the cellulase preparations.

2. Background Art

Treatment of cellulose-containing fabrics with cellulase is carried out to give the fabrics desired properties. For example, treatment with cellulase is carried out in the fiber industry in order to improve the touch and appearance of cellulose-containing fabrics or to give colored cellulose-containing fabrics an appearance of "stone-washed" material, i.e. partial color change (European Patent No. 307,564).

On the other hand, lyocell which is a regenerated cellulose fiber prepared from wood pulp-derived cellulose by an organic solvent spinning process has been attracting attention recently for its properties (such as high strength, water absorption) and the production process that causes less environmental pollution. However, since lyocell generates fuzz during its production, lyocell in that form is commercially evaluated rather low as a fabric product. Then, methods of removing the fuzz generating during production using cellulase have been proposed.

The term "cellulose-containing fabrics" used herein include fabrics prepared from cellulosic fiber materials such as natural cellulose (e.g., cotton, linen), regenerated cellulose (e.g., lyocell, rayon, polynosic, cupraammonium rayon); woven or knitted cloths from these fibers; and clothing items prepared by sewing these cloths. Further, those fabrics, cloths and sewn clothing items which comprise cellulosic fiber material(s) and other material(s) such as synthetic fiber, wool or silk, are also included in this term.

At present, cellulases derived from *Trichoderma* and *Humicola* (both are wood-rotting fungi) are mainly used in the treatment of cellulose-containing fabrics. These cellulases are mixtures of a plurality of cellulase components. Practical use of these cellulases has been hindered by the difficulty that a large quantity of cellulase preparation is needed in order to achieve a desired effect on a cellulose-containing fabrics.

The above-described drawback of these cellulose preparations is being improved by the development of preparations containing a large quantity of endoglucanases. For example, a number of endoglucanase-enriched cellulase preparations are disclosed in WO89/09259, WO91/17243, WO98/03640 and WO94/21801. In particular, WO91/17243 discloses that a *Humicola*-derived purified 43 kD endoglucanase component (EGV) exhibits jeans decoloring activity about 100-fold greater than that activity of conventional cellulase preparations which are mixtures of a plurality of cellulase components. WO98/03640 discloses that a *Humicola*-derived endoglucanase component NCE4 exhibits jeans decoloring activity and lyocell fuzz removal activity which are 25-fold and 100-hold greater than those activities of the conventional cellulase preparations, respectively. However, in order to remove strong fuzz generated in regenerated cellulose fabrics such as lyocell, cellulase preparations containing endoglucanase components of still higher activity are required to put them into practical use on an industrial scale.

Generally, the processing of cellulose-containing fabrics includes refining, bleaching, dyeing and mercerization; all of them are carried out under alkaline conditions. However, in the above-described conventional cellulose preparations containing a large quantity of endoglucanase, those derived from *Trichoderma* have an optimum pH in an acidic range and those derived from *Humicola* have an optimum pH in a neutral range. Thus, when these cellulase preparations are used, the cellulase treatment should be carried out separately from the above-mentioned fabrics processing steps, after pH adjustment by addition of buffers, etc.

Accordingly, if an endoglucanase component functioning under alkaline conditions is available, cellulase treatment can be carried out in the above-mentioned fabric processing steps. Thus, production steps can be shortened. As a result, it is believed that a great cost reduction can be achieved.

It is disclosed that *Rhizopus*-derived cellulases are capable of retaining their activity under alkaline conditions (Japanese Unexamined Patent Publications Nos. 60-226599, 64-40667, 64-26779 and 7-90300). In all of these disclosures, *Rhizopus* cultivation preparations are used for the purpose of providing detergents for use in the washing/rinsing of clothing. However, the activity of these *Rhizopus* cultivation preparations is extremely low and by far below the level required for practical use.

Highly active cellulase preparations are often provided as preparations containing a large quantity of endoglucanase as described above. For preparing such endoglucanase, methods are known in which an endoglucanase component of interest is recombinantly expressed in a host cell in a large quantity as described in WO91/17243, WO98/03667 and WO98/11139. Examples of preferable host cells in these methods include filamentous fungi belonging to Deuteromycotina, e.g., *Aspergillus*, *Humicola*, and *Trichoderma*. Considering enzyme production at an industrial level, these filamentous fungi belonging to Deuteromycotina will be extremely excellent hosts.

However, when a heterogeneous gene is expressed in these filamentous fungi belonging to Deuteromycotina, high expression is often hindered for reasons such as difference in codon usage. In particular, there has been no report of high expression of a gene derived from the genus *Rhizopus* belonging to Zygomycotina in the above-mentioned filamentous fungi belonging to Deuteromycotina. Thus, technology for high expression has been desired.

Under such circumstances, recently, a technology is being constructed which achieves high expression of a gene of interest in a host cell by optimizing the codons of the gene in conformity with the codon frequency in the host cell. The optimum use of codons for high expression of a gene of interest in a host may be presumed by examining the codon frequency in those genes expressed relatively abundantly in the host in natural environment. This is supported by the report of Lloyd et al. (Andrew T. Lloyd and Paul M. Sharp, 1991, Mol. Gen. Genet. 230, 288–294) concerning the codon frequency in *Aspergillus nidulans*, a filamentous fungus belonging to Deuteromycotina. However, even if information on appropriate codon use has been obtained from known DNA sequences, that information does not necessarily result in the realization of high expression of a gene of interest immediately. Especially, in filamentous fungi, which are complex to control, selection of a single sequence most suitable for expression from a number of sequences having suitable codon use has been required.

SUMMARY OF THE INVENTION

The present inventors have isolated highly active endoglucanases and genes thereof from Zygomycotina fungi *Rhizopus oryzae, Mucor circinelloides* and *Phycomyces nitens*. The inventors have found that these enzymes exhibit extremely strong activities in the removal of fuzz from regenerated cellulose fabrics and that they retain very strong activities under alkaline conditions. These endoglucanases have remarkably high activities 10- to 20-fold higher in neutral range and 20- to 50-fold higher in alkaline range than the activities of EGV (WO91/17243) and NCE4 (WO98/03640) derived from *Humicola* which are known to have high activities in fuzz removal from cellulose-containing fabrics.

Furthermore, even when these endoglucanases are used in a form of detergent composition for use at low temperatures and under alkaline conditions in general, it has been found that they have strong activities in the removal of fuzz from cotton. For example, these highly active endoglucanases have strong activities 2- to 20-fold greater than the activities of *Humicola*-derived EGV (WO91/17243) and NCE4 (WO98/03640) which are known to have strong activities in the removal of fuzz when used as a detergent.

More surprisingly, the present inventors have found that these endoglucanases have completely novel and characteristic amino acid sequences. Briefly, the conserved consensus sequence Gln-Cys-Gly-Gly in their cellulose binding domains is followed by Lys; or the conserved consensus residue Asn in the domain is followed by Lys.

Further, the present inventors have found a completely novel and characteristic sequence that is believed to be necessary for removal of fuzz from regenerated cellulose fabrics, in a part of their linker domains located close to the N-terminus of their catalytic domains.

Further, the present inventors have also found that these endoglucanases have a structure completely new as filamentous fungi-derived endoglucanases belonging to family 45 in the sense that their cellulose binding domains are located on the N-terminal side.

It is an object of the invention to provide enzymes, which exhibit very high endoglucanase activity on regenerated cellulose and retain high activity under alkaline conditions; and genes encoding the enzymes.

It is another object of the invention is to provide cellulase preparations with good properties.

It is still another object of the invention to provide effective and inexpensive methods of treating cellulose-containing fabrics, papers, pulps and animal feeds with the above-described enzymes.

The enzyme according to the present invention has the following properties:

a) exhibiting endoglucanase activity; and
b) capable of completely removing fuzz from a regenerated cellulose fabric at a concentration of I mg of the protein/L or below.

In another aspect of the invention, the enzyme having endoglucanase activity is a protein comprising the amino acid sequence as shown in SEQ ID NO: 1, 3, 5, 7, 9 or 11; a modified protein thereof exhibiting endoglucanase activity; or a homologue of the protein or the modified protein.

Further, the gene of the invention for the enzyme having endoglucanase activity comprises a nucleotide sequence encoding the above enzyme (e.g., the nucleotide sequence as shown in SEQ ID NO: 2, 4, 6, 8, 10, 12 or 13).

Further, the cellulase preparation of the invention comprises the above-described enzyme exhibiting endoglucanase activity.

Further, the method of the invention for treating cellulose-containing fabrics or the like comprises contacting the cellulose-containing fabrics or the like with the enzyme of the invention exhibiting endoglucanase activity or the cellulase preparation of the invention.

BRIEF DESCRIPTION OF THE INVENTION

FIG. 1 is a graph showing the relationship between reaction pH and relative activity in the removal of fuzz from lyocell on endoglucanases RCE I, MCE I, PCE I and NCE4.

FIG. 2 is a graph showing the relationship between reaction pH and relative activity in the removal of fuzz from lyocell on mutant endoglucanases RCE I, MCE I and endoglucanase NCE4.

FIG. 3 is a table showing the codon frequency in the gene encoding RCE I.

FIG. 4 is a table showing the codon frequency in the gene encoding NCE 1.

FIG. 5 is a table showing the codon frequency in the gene encoding NCE 2.

FIG. 6 is a table showing the codon frequency in the gene encoding NCE 4.

DISCLOSURE OF THE INVENTION

Definition

Amino acids are expressed in three-letter abbreviations.

The term "any amino acid residue" used herein includes Ala, Arg, Asn, Asp, Cys, Gin, Glu, Gly, His, Ile, Leu, Lys, Met, Phe, Pro, Ser, Thr, Trp, Tr and Val.

The term "nucleotide sequence" used herein includes not only DNA sequences but also RNA sequences.

Deposit of Microorganisms

*Rhizopus oryzae* CP96001 strain was deposited at the National Institute of Bioscience and Human-Technology, Agency of Industrial Science and Technology (1–3 Higashi 1-chome, Tsukuba City, Ibaraki Pref., Japan) under the accession No. FERM BP-6889 on Apr.21, 1997.

*Mucor circinelloides* CP99001 strain was deposited at the National Institute of Bioscience and Human-Technology, Agency of Industrial Science and Technology under the accession No. FERM BP-6890 on Jul. 2, 1999.

*Phycomyces nirens* CP99002 strain was deposited at the National Institute of Bioscience and Human-Technology, Agency of Industrial Science and Technology under the accession No. FERM BP-6891 on Jul. 2, 1999.

Enzymes Exhibiting Endoglucanase Activity

The enzyme of the invention has higher activity than hitherto known highly active endoglucanases in the removal of fuzz from regenerated cellulose fabrics such as lyocell, and has an advantage that it functions even under alkaline conditions. The high activity of the enzyme of the invention enables practical use of the enzyme because only a small quantity of cellulase preparation containing the enzyme is required to give desired effects on regenerated cellulose fabrics. Furthermore, the advantage that the enzyme functions even under alkaline conditions enables fuzz removal processing of regenerated cellulose fabrics under alkaline conditions which is now believed impossible. Thus, according to the enzyme of the invention, fabric-processing steps can be shortened and cost reduction can be realized.

Lyocell is a term for a regenerated cellulose fabric designated formerly by the Comite International de la Rayonne et des Fibres Synthetiques (CIRFS). As a common product, it is called Tencel™ (a trademark of Acordis Fibers). Since lyocell is a fiber prepared from wood pulp-derived cellulose by an organic solvent spinning process, it is classified into regenerated cellulose fiber. The other regenerated cellulose fibers such as viscose, rayon and polynosic are also prepared from wood pulp-derived cellulose and have the same crystal structure as that of lyocell. Therefore, when applied to these regenerated cellulose fibers, the enzyme according to the invention is capable of producing effects similar to those produced when applied to lyocell.

According to the first aspect of the invention, enzymes having the above-described properties a) and b) are provided.

Details of the properties of the enzyme according to the invention are as described blow.

(i) Function and Substrate Specificity

The enzyme of the invention is an enzyme exhibiting endoglucanase activity, i.e. endo-1,4-β-glucanase EC3.2.1.4. Specifically, the enzyme of the invention hydrolyzes the β-1,4-glucopyranosyl bond of β-1,4-glucan. This enzyme specifically acts on a regenerated cellulose fabric such as lyocell as a substrate, and is capable of removing fuzz from Tencel™ completely at an extremely low concentration (0.2–1.0 mg of the protein/L).

The term "activity of fuzz removal from a regenerated cellulose fabric" used herein means the activity that is evaluated by the method described in Example A4 or A5.

The expression "capable of completely removing fuzz from a regenerated cellulose fabric" used herein refers to a state in which no fuzz can be detected by the eye when a knit lyocell cloth that has been dyed brown and undergone fuzz-raising treatment is treated with an enzyme for fuzz removal. Specifically, the expression refers to a state of the fuzz-removed cloth in which the L* value (lightness) of L*a*b* color system as determined with a spectrophotometer (Minolta; model CM525i) under the conditions described in Example A6 is 24.5 or less. The cloth dyed brown before fuzz-raising treatment refers to a cloth whose L* value is in the range from 24 to 26; a* value (chromaticity) is in the range from 4.7 to 5.1; and b* value is in the range from 7.2 to 7.9. This lyocell cloth is a knit smooth cloth prepared with No. 40/1 count yarn and with gauge 30" *24G and then dyed brown with Sumifix (Sumitomo Chemical). As a specific example of a knit lyocell cloth product, OT7440 Knit Smooth (Toshima Co., Ltd.) may be given. In the above-mentioned fuzz-raising treatment, fuzz should be generated until the L* value reaches approximately 30 when a cloth with this color (brown) is used.

(ii) Optimum pH and pH at which the Enzyme is Stable

The fuzz removal activity of the endoglucanase of the invention when it is acted on regenerated cellulose fabrics at pH 8.5 is 50% or more of its fuzz removal activity at the optimum pH.

The *Rhizopus oryzae*-derived endoglucanase has high CMCase activity at pH 4–8, though the optimum pH for this activity is about 5. Also, it has high lyocell fuzz removal activity at pH 5–9, though the optimum pH for this activity is about 5.

The *Mucor circinelloides*-derived endoglucanase has high CMCase activity at pH 5–8, though the optimum pH for this activity is about 6. Also, it has high lyocell fuzz removal activity at pH 5–9, though the optimum pH for this activity is 5–6.

The *Phycomyces nitens*-derived endoglucanase has high CMCase activity at pH 5–8, though the optimum pH for this activity is about 6. Also, it has high lyocell fuzz removal activity at pH 5–8, though the optimum pH for this activity is about 6.

(iii) Optimum Temperature and Thermal Stability

The *Rhizopus oryzae*-derived endoglucanase has high CMCase activity at 45–65° C., though the optimum temperature range for this activity is 55–60° C. Also, it has high lyocell fuzz removal activity at 45–60° C., though the optimum temperature for this activity is about 55° C.

The *Mucor circinelloides*-derived endoglucanase has high CMCase activity at 40–60° C., though the optimum temperature range for this activity is $_{45-55}$° C. Also, it has high lyocell fuzz removal activity at about 45–55° C., though the optimum temperature for this activity is about 50° C.

The *Phycomyces nitens*-derived endoglucanase has high CMCase activity at about 40–60° C., though the optimum temperature range for this activity is 45–55° C. Also, it has high lyocell fuzz removal activity at about 45–55° C., though the optimum temperature for this activity is about 50° C.

(iv) Molecular Weight

The *Rhizopus oryzae*-derived endoglucanase may have a molecular weight of approximately 40 kDa; the *Mucor circinelloides*-derived endoglucanases may have a molecular weight of approximately 41 kDa; and the *Phycomyces nitens*-derived endoglucanase may have a molecular weight of approximately 45 kDa as determined by SDS-PAGE.

(v) N-Terminal Sequence

The *Rhizopus oryzae*-derived endoglucanase may have an N-terminal sequence represented by the amino acid sequence of SEQ ID NO: 14. The *Mucor circinelloides*-derived endoglucanase may have an N-terminal sequence represented by the amino acid sequence of SEQ ID NO: 15. The *Phycomyces nitens*-derived endoglucanase may have an N-terminal sequence represented by the amino acid sequence of SEQ ID NO: 16.

(vi) Cellulose Binding Domain

It is known that cellulases generally have a cellulose binding domain (CBD) at which they bind to cellulose. Further, it has been confirmed that filamentous fungi-derived cellulose binding domains have the following consensus sequence conserved (Hoffren, A.-M. et al, Protein Engineering 8:443–450, 1995):

```
Xaa  Xaa  Xaa  Xaa  Xaa  Xaa  Gln  Cys  Gly Gly  Xaa  Xaa  Xaa  Xaa
1                                            10

Gly Xaa  Xaa  Xaa  Cys  Xaa  Xaa  Xaa  Xaa  Xaa  Xaa  Cys  Xaa  Xaa
                20

Xaa Xaa  Xaa  Asn  Xaa  Xaa  Tyr  Xaa  Gln Cys  Xaa    (SEQ ID NO: 17)
30
``` wherein Xaa is independently any amino acid; and Xaa's at positions 20, 21, 22, 23, 24, 30 and 31 may be independently absent.

In the above sequence, the conserved consensus sequence Gln-Cys-Gly-Gly is usually followed by Ile, Gln, Ala, Ser or Asn; this consensus sequence followed by Lys has not been found. Also, the conserved consensus residue Asn in the above-described sequence is usually followed by Asp, Pro, Gin, Tyr or Ala; this consensus residue followed by Lys has not been found. The present inventors have found that the consensus sequence Gln-Cys-Gly-Gly is followed by Lys in the cellulose binding domains of RCE I, RCE II, RCE III and PCE I, and that the consensus residue Asn is followed by Lys in the cellulose binding domains of MCE I and MCE II. These are completely novel amino acid sequences.

The enzyme of the invention may have a cellulose-binding domain consisting of the following amino acid sequence (1):

Xaa-Xaa-Xaa-Xaa-Xaa-Xaa-Gln-Cys-Gly-Gly-Xaa-Xaa-Xaa-Xaa-Gly-Xaa-Xaa-Xaa-Cys-Xaa-Xaa-Xaa-Xaa-Xaa-Xaa-Cys-Xaa-Xaa-Xaa-Xaa-Xaa-Asn-Xaa-Xaa-Tyr-Xaa-Gln-Cys-Xaa (I) (SEQ ID NO: 18)

wherein Xaa is independently any amino acid residue; Xaa's at positions 20, 21, 22, 23, 24, 30 and 31 may be independently absent; preferably, Xaa at position 24 is absent; and one of Xaa at position 11 or 33 is Lys and the other is any amino acid residue except Lys.

Preferably, the cellulose binding domain of the enzyme of the invention may consists of the following amino acid sequence (II):

Cys-Ser-Xaa-Xaa-Tyr-Xaa-Gln-Cys-Gly-Gly-Xaa-Xaa-Trp-Xaa-Gly-Pro-Thr-Cys-Cys-Xaa-Xaa-Gly-Xaa-Thr-Cys-Xaa-Xaa-Xaa-Xaa-Xaa-Asn-Xaa-Xaa-Tyr-Ser-Gln-Cys-Xaa (II) (SEQ ID NO: 19)

wherein Xaa is independently any amino acid residue; and Xaa's at positions 20, 21, 23, 29 and 30 may be independently absent.

Preferably, one of Xaa at position 11 or 32 in above amino acid sequence (II) may be Lys and the other may be any amino acid residue except Lys.

More preferably, the cellulose binding domain of the enzyme of the invention may consists of the following amino acid sequence (III):

Cys-Ser-X1-X2-Tyr-X3-Gln-Cys-Gly-Gly-X4-X5-Trp-X6-Gly-Pro-Thr-Cys-Cys-X7-X8-Gly-X9-Thr-Cys-X10-X11-X12-X13-X14-Asn-X15-X16-Tyyr-Ser-Gln-Cys-X17 (III) (SEQ ID NO: 20)
wherein:
X1 is Lys, Ser or Gin;
X2 is Leu, Ala, Val or Gly;
X3 is Gly, Tyr or Ser;
X4 is Lys or De;
X5 is Asn, Asp, Gly or Met;
X6 is Asn, Asp, Ser or Thr;
X7 is Glu, Asp or Thr;
X8 is Ser or Ala;
X9 is Ser or Phe;
X10 is Lys or Val;
X11 is Val, Asp, Ala or Gly;
X12 is Ser, Tyr, Gin or Ala;
X13 is Pro, Glu or Lys, or is absent;
X14 is Asp, Gly or Asn, or is absent;
X15 is Asp, Pro, Lys or Glu;
X16 is Tyr, Phe or Trp;
X17 is Leu, Val or Ile; and
one of X4 or X15 is Lys and the other is any amino acid residue except Lys.

The enzyme of the invention derived from the genus *Rhizopus* may have a cellulose-binding domain consisting of the following amino acid sequence (IV):

Cys-Ser-Lys-X21-Tyr-X22-Gln-Cys-Gly-Gly-Lys-X23-Trp-X24-Gly-Pro-Thr-Cys-Cys-Glu-Ser-Gly-Ser-Thr-Cys-X25-X26-X27-X28-X29-Asn-X30-X31-Tyr-Ser-Gln-Cys-X32 (IV) (SEQ ID NO: 21)
wherein:
X21 is Leu or Ala;
X22 is Gly or Tyr;
X23 is Asn or Asp;
X24 is Asn or Asp;
X25 is Lys or Val;
X26 is Val or Asp;
X27 is Ser or Tyr;
X28 is Pro, or is absent;
X29 is Asp, or is absent;
X30 is Asp or Pro;
X31 is Tyr or Phe; and
X32 is Leu or Val.

Preferably, the cellulose binding domain consisting of the amino acid sequence (IV) may consists of any one of the amino acid sequences of SEQ ID NOS: 22, 23, and 24.

The enzyme of the invention derived from the genus *Mucor* may have a cellulose-binding domain consisting of the following amino acid sequence (V):

Cys-Ser-Ser-Val-Tyr-X41-Gln-Cys-Gly-Gly-Ile-Gly-Trp-X42-Gly-Pro-Thr-Cys-Cys-X43-X44-Gly-Ser-Thr-Cys-X45-Ala-Gln-X46-X47-Asn-Lys-Tyr-Tyr-Ser-Gln-Cys-X48 (V) (SEQ ID NO: 25)
wherein:
X41 is Gly or Ser;
X42 is Ser or Thr;
X43 is Glu or Asp;
X44 is Ser or Ala;
X45 is Val or Lys;
X46 is Glu or Lys;
X47 is Gly or Asp; and
X48 is Leu or Ile.

The cellulose binding domain consisting of the amino acid sequence (V) may comprise the amino acid sequence of SEQ ID NO: 26 or 27.

The enzyme of the invention derived from the genus *Phycoinyces* may have a cellulose binding domain comprising the amino acid sequence of SEQ ID NO: 28.

(vii) Linker Region and Catalytic Domain

It is known that endoglucanases have a catalytic domain, which cleaves cellulose. The amino acid region, which binds a catalytic domain to a cellulose-binding domain, is called a linker region. Endoglucanases belonging to family 45 are confirmed to have a conserved consensus sequence (Ser or Thr or Ala)-Thr-Arg-Tyr-(Trp or Tyr or Phe)-Asp-Xaa-Xaa-Xaa-Xaa-Xaa-(Cys or Ala) (SEQ ID NO: 29) in an upstream region within their catalytic domains. The present inventors have found that deletion of a specific region upstream of this consensus sequence (i.e., a specific part of the linker region) eliminates lyocell fuzz removal activity (Example D9), and further found that a novel sequence Tyr-Xaa-Xaa-Xaa-Ser-Gly-Gly-Xaa-Ser-Gly (SEQ ID NO: 30) common in *Zygomycotina*-derived 6 endoglucanases is present within the region.

The enzyme of the invention may comprise a part of its linker region consisting of the following amino acid sequence (VI):

Tyr-Xaa-Xaa-Xaa-X51-Gly-Gly-Xaa-X52-Gly (VI) (SEQ ID NO: 31)

wherein Xaa is independently any amino acid residue; X51 and X52 are independently Ser or Thr; and preferably, both X51 and X52 are Ser.

Preferably, the part of the linker region may consist of the following amino acid sequence (VII):

Tyr-X61-Xaa-X62-X51-Gly-Gly-Xaa-X52-Gly (VII) (SEQ ID NO: 32)
wherein:
Xaa is any amino acid residue; preferably, Xaa at position 3 is Ala, Ile, Pro or Val; and Xaa at position 8 is Ala, Phe or Lys;
X51 and X52 are independently Ser or Thr; preferably, both X51 and X52 are Ser;
X61 is Lys or Ser; and
X62 is Ile or Val.

More preferably, the part of the linker region may comprise any one of the sequences as shown in SEQ ID NOS: 33, 34, 35, 36 and 37.

The enzyme according to the invention is characterized by comprising a cellulose-binding domain, a linker region and a catalytic domain located in this order in the direction from the N-terminus to the C-terminus.

The "part of the linker region" used herein means a part located within the linker region and located close to the N-terminus of the catalytic domain. Specifically, the C-terminus amino acid of this part of the linker region is located 6–14 amino acids, preferably 7–11 amino acids, and more preferably 9 amino acids upstream of the Asp residue in the consensus sequence (Ser or Thr or Ala)-Thr-Arg-Tyr-(Trp or Tyr or Phe)-Asp-Xaa-Xaa-Xaa-Xaa-Xaa-(Cys or Ala) (SEQ ID NO: 29) conserved in the catalytic domain.
(viii) Original Source The enzymes according to the invention can be obtained from Zygomycotina. Specifically, they can be obtained from microorganisms of the genus *Rhizopus* (e.g., *Rhizopus oryzae*), the genus *Mucor* (e.g., *Mucor circinelloides*) or the genus *Phycomyces* (e.g., *Phycomyces nitens*).

According to another aspect of the invention, there is provided an enzyme, which comprises a cellulose-binding domain consisting of any one of the amino acid sequences (I) to (V) and shows endoglucanase activity.

According to another aspect of the invention, there is provided an enzyme which comprises a part of its linker region consisting of the amino acid sequence (VI) or (VII) and shows endoglucanase activity.

According to another aspect of the invention, there is provided an enzyme which comprises a cellulose binding domain consisting of any one of the amino acid sequences (I) to (V) and a part of its linker region consisting of the amino acid sequence (VI) or (VII), and exhibits endoglucanase activity.

According to another aspect of the invention, there is provided an endoglucanase having the following characteristics:
 i) belonging to family 45;
 ii) being derived from a filamentous fungus; and
 iii) having a cellulose-binding domain located on its N-terminal side.

An endoglucanase "belonging to family 45" refers to an endoglucanase which has the conserved consensus sequence (Ser or Thr or Ala)-Thr-Arg-Tyr-(Trp or Tyr or Phe)-Asp-Xaa-Xaa-Xaa-Xaa-Xaa-(Cys or Ala) (SEQ ID NO: 29) in its catalytic domain (NiceSite View of PROSITE: PDOC00877 or PS01140, PROSITE Database of protein families and domains).

As an endoglucanase "derived from a filamentous fungus and belonging to family 45", enzymes such as EGV, NCE4 and egl5 (Saloheimo, A. et al., Molecular Microbiology 13:219–228, 1994) are known. In all of these enzymes, the cellulose-binding domain is located on their C-terminal side (Schulein, M., Biochemical Society Transactions 26:164–167, 1998). However, *Zygomycotina*-derived 6 endoglucanases according to the invention belong to family 45 and have a completely novel structure in which the cellulose binding domain is located on their N-terminal side.

Specific examples of endoglucanases "belonging to family 45" according to the invention include an enzyme comprising the amino acid sequence as shown in SEQ ID NO: 1, 3, 5, 7, 9 or 11 and exhibiting endoglucanase activity; a modified protein thereof exhibiting endoglucanase activity; and a homologue of the enzyme or the modified protein which still retains the conserved consensus sequence (Ser or Thr or Ala)-Thr-Arg-Tyr-(Trp or Tyr or Phe)-Asp-Xaa-Xaa-Xaa-Xaa-Xaa-(Cys or Ala) (SEQ ID NO: 29) in its catalytic domain. Specific examples of cellulose binding domains and original sources may include the cellulose binding domains and origin sources described above.

According to another aspect of the invention, there is provided a protein comprising the amino acid sequence as shown in SEQ ID NO: 1, 3, 5, 7, 9 or II as an enzyme exhibiting endoglucanase activity. Hereinafter, the proteins having the amino acid sequences of SEQ ID NOS: 1, 3, 5, 7, 9 and 11 are referred to as endoglucanases RCE I, RCE II, RCE III, MCE I, MCE II and PCE I, respectively.

The present invention encompasses not only the polypeptides having the amino acid sequence as shown in SEQ ID NO: 1, 3, 5, 7, 9 or 11 but also modified proteins thereof. In the present invention, the modified protein means a protein which comprises the amino acid sequence as shown in SEQ ID NO: 1, 3, 5, 7, 9 or 11 having modification such as addition, insertion, deletion or substitution in one or more amino acids (e.g., one to several ten amino acids; specifically, one to about 50, preferably one to about 30, more preferably one to about 9 amino acids) and which still retains endoglucanase activity.

Examples of the modified protein include a protein consisting of an amino acid sequence represented by SEQ ID NO: 1, 3, 5, 7, 9 or 11 which is modified so that asparagines (Asn)-linked oligosaccharide chains are not added thereto as described later.

Examples of the modified protein further include a protein consisting of an amino acid sequence represented by SEQ ID NO: 1, 3, 5, 7, 9 or 11 whose cellulose binding domain is modified. More specifically, examples of the modified protein include a protein consisting of an amino acid sequence represented by SEQ ID NO: 1, 3, 5, 7, 9 or 11 which is modified so that its cellulose binding domain represents one of the amino acid sequences (I) to (V) and which may have a modification(s) in regions other than the cellulose binding domain. The number of amino acids, which may be modified in the cellulose-binding domain, is one to about 28, preferably one to about 17.

Examples of the modified protein further include a protein consisting of an amino acid sequence represented by SEQ ID NO: 1, 3, 5, 7, 9 or 11 in which a part of its linker region is modified. More specifically, examples of the modified protein include a proteinconsisting of an amino acid sequence represented by SEQ ID NO: 1, 3, 5, 7, 9 or 11 which is modified so that a part of its linker region represents the amino acid sequence (VI) to (VII) and which may have a modification(s) in regions other than the part of the linker region. The number of amino acids, which may be modified in the linker region, is one to about 6, preferably one to about 4.

Examples of the modified protein further include a protein consisting of an amino acid sequence represented by SEQ ID NO: 1, 3, 5, 7, 9 or 11 in which its cellulose binding domain and a part of its linker region are modified. More specifically, examples of the modified protein include a protein consisting of an amino acid sequence represented by SEQ ID NO: 1, 3, 5, 7, 9 or 11 which is modified so that its cellulose binding domain represents one of the amino acid sequences (I) to (V) and yet modified so that a part of its linker region represents the amino acid sequence (VI) or (VII), and which may have a modification(s) in regions other than the cellulose binding domain and the part of the linker region. The number of amino acids, which may be modified in the cellulose-binding domain, is one to about 28, preferably one to about 17. The number of amino acids, which may be modified in the linker region, is one to about 6, preferably one to about 4.

Further, examples of the modified protein include a protein consisting of an amino acid sequence represented by SEQ ID NO: 1, 3, 5, 7, 9 or 11 which is modified in a region(s) other than the cellulose binding domain (CBD) and a part of the linker region. The number of amino acids which may be modified in a region(s) other than the CBD and the part of the linker region is one to about 30, preferably one to about 15. Of these, the number of amino acids, which may be modified in the catalytic domain, is one to about 20, preferably one to about 10.

Further, examples of the modified protein include a protein consisting of an amino acid sequence represented by SEQ ID NO: 1, 3, 5, 7, 9 or 11 which is modified in a region(s) other than the CBD, a part of the linker region and the catalytic domain (CAD). The number of amino acids which may be modified in a region(s) other than the CBD, the part of the linker region and the CAD is one to about 10, preferably one to about 5.

The locations (i.e., amino acid positions) of the CBD(s), the part of the linker region and the CAD in each of SEQ ID NOS: 1, 3, 5, 7, 9 and 11 are shown in the table below.

|  | CBD | Part of Linker Region | CAD |
| --- | --- | --- | --- |
| SEQ ID NO: 1 | 3~38 | 99~108 | 109~315 |
| SEQ ID NO: 3 | 3~38, 50~85 | 127~136 | 137~343 |
| SEQ ID NO: 5 | 3~40 | 122~131 | 132~337 |
| SEQ ID NO: 7 | 3~40 | 104~113 | 114~316 |
| SEQ ID NO: 9 | 3~40, 52~89 | 153~162 | 163~365 |
| SEQ ID NO: 11 | 3~40 | 115~124 | 125~327 |

Further, the present invention not only encompasses polypeptides having the amino acid sequence as shown in SEQ ID NO: 1, 3, 5, 7, 9 or 11 and modified proteins thereof, but also encompasses homologues of the polypeptides and the modified proteins. The term "homologue" used herein means a polypeptide which has an amino acid sequence encoded by a gene (nucleotide sequence) that hybridizes with a gene (nucleotide sequence) encoding the amino acid sequence of SEQ ID NO: 1, 3, 5, 7, 9 or 11 "under limited conditions", and which has endoglucanase activity. The term "limited conditions" used herein means conditions controlled to such an extent that while a probe comprising a nucleotide sequence encoding a part or all of the amino acid sequence as shown in SEQ ID NO: 1, 3, 5, 7, 9 or 11 or the modified version thereof hybridizes with a gene encoding the homologue, this probe does not hybridize with the gene of endoglucanase NCE4 disclosed in WO98/03640 nor with the gene of endoglucanase SCE3 disclosed in WO98/54332 gene (provided that equal amounts of NCE4 gene, SCE3 gene and the gene encoding the homologue are used in the hybridization). More specifically, conditions as described below may be given, for example. Briefly, the full length of the DNA sequence as shown in SEQ ID NO: 2 is labeled and provided as a probe. Then, according to the protocol of ECL direct DNA/RNA labeling detection system (Amersham), the probe is added after 1 hr pre-hybridization (at 42° C.). After 15 hr hybridization (at 42° C.), the washing with 0.4% SDS, 6 M urea-added 0.5×SSC (SSC: 15 mM trisodium citrate, 150 mM sodium chloride) at 42° C. for 20 min is repeated twice, and then the washing with 5×SSC at room temperature for 10 min is repeated twice.

The enzyme of the invention may be isolated and purified from a microorganism as described in Examples A1–3.

Alternatively, the enzyme of the invention may be obtained by expressing a nucleotide sequence encoding the enzyme in an appropriate host by recombinant gene technology and isolating/purifying the resultant protein.

The enzyme of the invention also includes a recombinant enzyme consisting of the above-described cellulose binding domain, the specific part of the linker region and any catalytic domain. Such recombinant enzymes may be produced, for example, according to the method of Tomme, P. et al., J. Bioteriol. 177:4356–4363, 1995.

Endoglucanase Genes

According to the invention, there is provided a nucleotide sequence encoding a protein comprising the amino acid sequence as shown in SEQ ID NO: 1, 3, 5, 7, 9 or 11; a modified protein thereof; or a homologue of the protein or the modified protein. If an amino acid sequence of a protein is given, DNA sequences encoding the same are easily determined. Thus, various nucleotide sequences encoding a protein comprising the amino acid sequence as shown in SEQ ID NO: 1, 3, 5, 7, 9 or 11; a modified protein thereof; or a homologues of the protein or the modified protein may be selected.

The nucleotide sequence of according to the present invention may be a naturally occurring sequence or a fully synthetic sequence. Alternatively, the nucleotide sequence may be a sequence synthesized utilizing a part of a naturally occurring sequence. Typically, the nucleotide sequence of the invention is obtained from a chromosomal or cDNA library derived from a microorganism, such as *Mucor circinelloides* or *Phycomyces nitens,* by conventional methods in the art of genetic engineering, e.g., screening with an appropriate DNA prove prepared based on information concerning a partial amino acid sequence.

Hereinbelow, endoglucanases RCE I, RCE II, RCE II, MCE I, MCE II and PCE I, and genes thereof will be described in more detail.

(1) Endoglucanase RCE I and Genes thereof

Endoglucanase RCE I of the invention is an enzyme having the amino acid sequence spanning from position 1 to position 315 of SEQ ID NO: 1 and having endoglucanase activity. The amino acid sequence spanning from position −23 to position −1 of SEQ ID NO: 1 or a part thereof may be added to the N-terminus of the above protein. The polypeptide to which this sequence is added is included within the invention as a modified peptide of endoglucanase RCE I. Since this amino acid sequence spanning from position −23 to position −1 is believed to be a signal peptide for secretion, a part of the sequence means a partial sequence retaining the signal peptide activity as well as a sequence remaining at the N-terminus as a result of some difference that occurred in the site of processing depending on the type of the host.

According to the present invention, there are provided endoglucanase RCE I genes encoding the amino acid sequence of SEQ ID NO: 1. A typical sequence of these genes comprises a part or all of the nucleotide sequence of SEQ ID NO: 2. The nucleotide sequence of SEQ ID NO: 2 contains an open reading frame staring with ATG at positions 1–3 and ending with TAA at positions 1015–1017. The nucleotide sequence of positions 70–72 corresponds to the N-terminal amino acid in the above-described mature protein consisting of 315 residues.

(2) Endoglucanase RCE II and Genes thereof

Endoglucanase RCE II of the invention is an enzyme having the amino acid sequence spanning from position 1 to position 343 of SEQ ID NO: 3 and having endoglucanase activity. The amino acid sequence spanning from position −23 to position −1 of SEQ ID NO: 3 or a part thereof may be added to the N-terminus of the above protein. The polypeptide to which this sequence is added is included within the invention as a modified peptide of endoglucanase RCE II. Since this amino acid sequence spanning from position −23 to position −1 is believed to be a signal peptide, a part of the sequence means a partial sequence retaining the signal peptide activity as well as a sequence remaining at the N-terminus as a result of some difference that occurred in the site of processing depending on the type of the host.

According to the present invention, there are provided endoglucanase RCE II genes encoding the amino acid sequence of SEQ ID NO: 3. A typical sequence of these genes comprises a part or all of the nucleotide sequence of SEQ ID NO: 4. The nucleotide sequence of SEQ ID NO: 4 contains an open reading frame staring with ATG at positions 1–3 and ending with TAA at positions 1099–1 101. The nucleotide sequence of positions 70–72 corresponds to the N-terminal amino acid in the above-described mature protein consisting of 343 residues.

(3) Endoglucanase RCE m and Genes thereof

Endoglucanase RCE III of the invention is an enzyme having the amino acid sequence spanning from position 1 to position 337 of SEQ ID NO: 5 and having endoglucanase activity. The amino acid sequence spanning from position −23 to position −1 of SEQ ID NO: 5 or a part thereof may be added to the N-terminus of the above protein. The polypeptide to which this sequence is added is included within the invention as a modified peptide of endoglucanase RCE III. Since this amino acid sequence spanning from position −23 to position −1 is believed to be a signal peptide, a part of the sequence means a partial sequence retaining the signal peptide activity as well as a sequence remaining at the N-terminus as a result of some difference that occurred in the site of processing depending on the type of the host.

According to the present invention, there are provided endoglucanase RCE III genes encoding the amino acid sequence of SEQ ID NO: 5. A typical sequence of these genes comprises a part or all of the nucleotide sequence of SEQ ID NO: 6. The nucleotide sequence of SEQ ID NO: 6 contains an open reading frame staring with ATG at positions 1–3 and ending with TAA at positions 1081–1083. The nucleotide sequence of positions 70–72 corresponds to the N-terminal amino acid in the above-described mature protein consisting of 337 residues.

(4) Endoglucanase MCE I and Genes thereof Endoglucanase MCE I of the invention is an enzyme having the amino acid sequence spanning from position 1 to position 316 of SEQ ID NO: 7 and having endoglucanase activity. The amino acid sequence spanning from position −22 to position −1 of SEQ ID NO: 7 or a part thereof may be added to the N-terminus of the above protein. The polypeptide to which this sequence is added is included within the invention as a modified peptide of endoglucanase MCE I. Since this amino acid sequence spanning from position −22 to position −1 is believed to be a signal peptide for secretion, a part of the sequence means a partial sequence retaining the signal peptide activity as well as a sequence remaining at the N-terminus as a result of some difference that occurred in the site of processing depending on the type of the host.

According to the present invention, there are provided endoglucanase MCE I genes encoding the amino acid sequence of SEQ ID NO: 7. A typical sequence of these genes comprises a part or all of the nucleotide sequence of SEQ ID NO: 8. The nucleotide sequence of SEQ ID NO: 8 contains an open reading frame staring with ATG at positions 1–3 and ending with TAA at positions 1015–1017. The nucleotide sequence of positions 6769 corresponds to the N-terminal amino acid in the above-described mature protein consisting of 316 residues.

(5) Endoglucanase MCE II and Genes thereof

Endoglucanase MCE II of the invention is an enzyme having the amino acid sequence spanning from position 1 to position 365 of SEQ ID NO: 9 and having endoglucanase activity. The amino acid sequence spanning from position −22 to position −1 of SEQ ID NO: 9 or a part thereof may be added to the N-terminus of the above protein. The polypeptide to which this sequence is added is included within the invention as a modified peptide of endoglucanase MCE II. Since this amino acid sequence spanning from position −22 to position −1 is believed to be a signal peptide, a part of the sequence means a partial sequence retaining the signal peptide activity as well as a sequence remaining at the N-terminus as a result of some difference that occurred in the site of processing depending on the type of the host.

According to the present invention, there are provided endoglucanase MCE II genes encoding the amino acid sequence of SEQ ID NO: 9. A typical sequence of these genes comprises a part or all of the nucleotide sequence of SEQ ID NO: 10. The nucleotide sequence of SEQ ID NO: 10 contains an open reading frame staring with ATG at positions 1–3 and ending with TAA at positions 1162–1164. The nucleotide sequence of positions 67–69 corresponds to the N-terminal amino acid in the above-described mature protein consisting of 365 residues.

(6) Endoglucanase PCE I and Genes thereof

Endoglucanase PCE I of the invention is an enzyme having the amino acid sequence spanning from position 1 to position 327 of SEQ ID NO: 11 and having endoglucanase activity. The amino acid sequence spanning from position −19 to position −1 of SEQ ID NO: 11 or a part thereof may be added to the N-terminus of the above protein. The polypeptide to which this sequence is added is included within the invention as a modified peptide of endoglucanase PCE I. Since this amino acid sequence spanning from position −19 to position −1 is believed to be a signal peptide, a part of the sequence means a partial sequence retaining the signal peptide activity as well as a sequence remaining at the N-terminus as a result of some difference that occurred in the site of processing depending on the type of the host.

According to the present invention, there are provided endoglucanase PCE I genes encoding the amino acid sequence of SEQ ID NO: 1. A typical sequence of these genes comprises a part or all of the nucleotide sequence of SEQ ID NO: 12. The nucleotide sequence of SEQ ID NO: 12 contains an open reading frame staring with ATG at positions 1–3 and ending with TAA at positions 1039–1041. The nucleotide sequence of positions 58–60 corresponds to the N-terminal amino acid in the above-described mature protein consisting of 327 residues.

Expression Vectors and Transformed Microorganisms

According to the invention, there is provided an expression vector replicable in a host microorganism, which comprises a nucleotide sequence encoding a protein comprising the amino acid sequence as shown in SEQ ID NO: 1, 3, 5, 7, 9 or II; a modified protein thereof, or a homologue of the protein or the modified protein operably linked thereto. This expression vector is an autonomously replicating vector and may be constructed based on, for example, a plasmid that exists as an extrachromosomal entity and replicates independently of the chromosome. Alternatively, the expression vector may be a vector, which is integrated into the genome of the microorganism host upon introduction thereinto and replicated together with the chromosome into which it has been incorporated. For the construction of the vector of the invention, conventional procedures and methods used in the field of genetic engineering may be used.

For the expression of a protein with desired activity upon introduction into the host microorganism, it is desirable that the expression vector of the invention contains DNA sequences to regulate the expression and gene markers, etc. for the selection of transformed microorganism, in addition to the DNA sequence of the invention. Examples of expression regulatory DNA sequences include promoters, terminators and DNA sequences encoding signal peptides. A promoter, which may be used in the invention, is not particularly limited as long as it shows transcription activity in the host microorganism. It may be obtained as a DNA sequence, which controls the expression of a gene encoding a protein homogeneous or heterogeneous to the host microorganism. A signal peptide, which may be used in the invention, is not particularly limited as long as it contributes to the secretion of protein in the host microorganism. It may be obtained from DNA sequences derived from a gene encoding a protein homogeneous or heterogeneous to the host microorganism. A gene marker, which may be used in the invention, may be appropriately selected depending on the method of selection of transformants. For example, genes encoding drug resistance or genes complementing auxotrophy may be used.

According to the present invention, there is further provided a microorganism transformed with the expression vector. This host-vector system is not particularly limited. Examples of useful host-vector system include a system using a microorganism such as *Escherichia coli*, actinomycetes, yeast or filamentous fungus; and a fusion protein expression system using such a microorganism.

Transformation of microorganisms with the expression vector of the invention may be performed by conventional methods in the art.

Further, the resultant transformant may be cultivated in an appropriate medium followed by isolation of the protein of the invention from the resultant cultivation broth. Thus, according to another aspect of the invention, there is provided a method of producing the novel protein of the invention. The cultivation condition of the transformant may be essentially the same as those for the microorganism used as the host. As to the method of recovering the protein of interest from the cultivation broth of the transformant, conventional methods in the art may be used.

According to a preferred aspect of the invention, there are provided yeast cells capable of expressing the endoglucanase encoded by the DNA sequence of the invention. Examples of yeast cells, which may be used in the invention, include microorganisms belonging to the genus *Saccharomyces*, the genus *Hansenula* or the genus *Pichia* (e.g., *Saccharomyces cerevisiae*).

Furthermore, according to the present invention, there is provided a method of improving an endoglucanase produced by yeast transformed with the expression vector of the invention when the endoglucanase does not exhibit an activity available to an appropriate use in the invention. Examples of activities available to appropriate uses according to the invention include the activity that can be used in the removal of fuzz from cellulose-containing fabrics.

It was reported by Van Arsdell, J. N. et al. that when a heterogeneous protein is expressed in yeast cells, sometimes, over-glycosylation (i.e., excessive addition of sugar chains) occurs (an Arsdell, J. N., 1987, Bio Technology, 5, 60–64). Therefore, in order to express a protein with a desired activity in such yeast cells, control of glycosylation addition may be necessary. As one example of such control, the present invention provides a method in which the Asparagine(Asn)-linked glycosylation site(s) of an endoglucanase is/are modified to thereby create a mutant endoglucanase to which Asn-linked oligosaccharide chains will not be added (Examples B9, C6, C10 and E4).

The modification of an endoglucanase consisting of the amino acid sequence of SEQ ID NO: 1, 3, 5, 7, 9 or 11 into a mutant endoglucanase to which Asn-linked oligosaccharide chains will not be added may be the replacement of Asn, Ser and/or Thr in the Asn-linked glycosylation site(s) represented by the sequence Asn-Xaa-Ser/Thr with other amino acid residue. Specifically, the modification may be the replacement of Asn with Asp or Gln; the replacement of Ser or Thr with Ala, Gy or Leu; or the replacement of Xaa with Pro in the glycosylation site(s).

As described in Examples C10 and C11, enzyme activity can be improved greatly by modifying even one Asn-linked glycosylation site adjacent to the cellulose-binding domain. Examples of mutant endoglucanases to which Asn-linked oligosaccharide chains will not be added include endoglucanases consisting of one of the following amino acid sequences:

A modified amino acid sequence represented by SEQ ID NO: 1 where the amino acid residue at position 45 or 47 is replaced by other amino acid residue;

A modified amino acid sequence represented by SEQ ID NO: 3 where the amino acid residue at position 45 or 47 is replaced by other amino acid residue;

A modified amino acid sequence represented by SEQ ID NO: 5 where the amino acid residue at position 44 or 46 is replaced by other amino acid residue;

A modified amino acid sequence represented by SEQ ID NO: 7 where the amino acid residue at position 50 or.52 is replaced by other amino acid residue; and A modified amino acid sequence represented by SEQ ID NO: 9 where the amino acid residue at position 99 or 101 is replaced by other amino acid residue.

Further examples of mutant endoglucanases to which Asn-linked oligosaccharide chains will not be added include endoglucanases consisting of one of the following amino acid sequences:

A modified amino acid sequence represented by SEQ ID NO: 1 where the amino acid residue at position 45 or 47 and the amino acid residue(s) at position 90 or 92 and/or 130 or 132 are replaced by other amino acid residues;

A modified amino acid sequence represented by SEQ ID NO: 3 where the amino acid residue at position 45 or 47, and the amino acid residue(s) at position 92 or 94, 119 or 121, 122 or 124 and/or 158 or 160 are replaced by other amino acid residues; and A modified amino acid sequence represented by SEQ ID NO: 5 where the amino acid residue at position 44 or 46 and the amino acid residue(s) at position 49 or 51, 121 or 123 and/or 171 or 173 are replaced by other amino acid residues.

More specifically, examples of mutant endoglucanases to which Asn-linked oligosaccharide chains will not be added include endoglucanases consisting of one of the following amino acid sequences:

A modified amino acid sequence represented by SEQ ID NO: 1 where Ser at position 47 is replaced by Ala; Ser at position 92 is replaced by Gly; and Asn at position 130 is replaced by Asp;

A modified amino acid sequence represented by SEQ ID NO: 3 where Ser at position 47 is replaced by Ala; Asn at position 92 is replaced by Gln; Ser at position 121 is replaced by Leu; Asn at position 122 is replaced by Asp; and Asn at position 158 is replaced by Asp;

A modified amino acid sequence represented by SEQ ID NO: 5 where Asn at position 44 is replaced by Asp; and Asn at position 121 is replaced by Lys;

A modified amino acid sequence represented by SEQ ID NO: 7 where Ser at position 52 is replaced by Gly; and A modified amino acid sequence represented by SEQ ID NO: 9 where Ser at position 101 is replaced by Gly.

In the control of glycosylation as described above, it is also possible to use host yeast cells of which glycosylation capacity has been limited (or even deleted) by mutagenesis techniques known in the art As a most suitable method for producing the endoglucanase of the invention, a method is provided in which the endoglucanase is expressed in filamentous fungi belonging to Deuteromycotina. When the enzyme is expressed in filamentous fungi belonging to Deuteromycotina, it is desirable to use a codon-optimized gene in which codons have been optimized in conformity with the codon usage in host filamentous fungi. In the present invention, a "codon-optimized gene" means a gene having such a DNA sequence as obtained by substituting codons in a DNA sequence encoding a protein based on information on frequently used codons in a host filamentous fungus.

Examples of most suitable codon-optimized genes in the invention include genes which do not contain intron recognition sequences or which seldom contain such sequences. The term "intron recognition sequence" used herein means a DNA sequence, which may be recognized by filamentous fungi belonging to Deuteromycotina as an intron. More specifically, the intron recognition sequence means a DNA sequence such as GTAGN, GTATN, GTAAN, GTACGN, GTGTN, GCACGN or GTTCGN. The absence of these DNA sequences leads to an improvement in the stability of MRNA that is the transcript of a gene of interest.

According to the present invention, it is possible to obtain an industrially preferable yield of the endoglucanase by totally synthesizing the above-described codon-optimized gene, integrating it into an expression vector and transforming a host filamentous fungus with the vector. The host filamentous fungus in the invention may belong to the genus *Humicola, Aspergillus, Trichoderma, Acremonium* or *Fusarium.* Preferable examples of them include *Humicola insolens, Aspergillus niger* and *Trichoderma viride.*

One example of the codon-optimized genes used in the invention is codon-optimized endoglucanase RCE I gene. This gene is a codon-optimized gene encoding endoglucanase RCE I having the amino acid sequence as shown in SEQ ID NO: 1. A typical sequence of this gene comprises a part or all of the nucleotide sequence as shown in SEQ ID NO: 13. The nucleotide sequence as shown in SEQ ID NO: 13 contains an open reading frame starting with ATG at positions 16–18 and ending with TAA at positions 1030–1032. The nucleotide sequence of positions 85–87 corresponds to the N-terminal amino acid of the above-mentioned mature protein of 315 residues.

Uses of Cellulases/Cellulase Preparations

According to another aspect of the invention, there are provided cellulase preparations comprising the endoglucanase of the invention, modified protein thereof or homologue thereof. The cellulase preparation of the invention may be prepared by mixing the endoglucanase of the invention, modified protein thereof or homologue thereof with components generally contained in cellulase preparations, such as excipients (e.g., lactose, sodium chloride, sorbitol); surfactants; and preservatives. The cellulase preparation of the invention may be prepared into an appropriate form such as powder or liquid formulation, or granules.

According to the present invention, there is further provided a method of reducing a speed at which cellulose-containing fabrics become fuzzy or reducing fuzzing in such a fabric; or a method of reducing a speed at which cellulose-containing fabrics become stiff or reducing stiffness in such a fiber. Each of these methods comprises a step of treating cellulose-containing fabrics with the endoglucanase or the cellulase preparation of the invention.

According to the present invention, there are further provided a method of color clarification of colored cellulose-containing fabrics, comprising a step of treating the colored cellulose-containing fabrics with the endoglucanase or the cellulase preparation; and a method of providing colored cellulose-containing fabrics with partial color change, i.e., a method of providing colored cellulose-containing fabrics with an appearance of stone-washed material, which method comprises a step of treating the colored cellulose-containing fabrics with the endoglucanase or the cellulase preparation of the invention.

The methods of the invention described above may be carried out by treating cellulose-containing fabrics during washing. Alternatively, on some occasions, the treatment of fabrics may be carried out during soaking or rinsing by adding the endoglucanase or the cellulase preparation of the invention into water where the fabric is soaked or to be soaked.

Conditions such as the contact temperature or the amount of endoglucanase may be appropriately decided considering other various conditions. For example, in the treatment for reducing a speed at which cellulose-containing fabrics become fuzzy or reducing fuzzing in such a fabric, the fabric can be treated with the endoglucanase at a protein concentration of 0.2–1 mg/L at about 45–55° C.

In weight loss treatment of cellulose-containing fabrics to improve its touch and appearance, the fabrics can be treated with the endoglucanase at a protein concentration of 5–100 mg/L at about 45–55° C.

Further, the fabrics can be treated with the endoglucanase at a protein concentration of 2–10 mg/L at about 45–55° C. to provide colored cellulose-containing fabrics with partial color change.

By using the endoglucanase or the cellulase preparation of the invention in detergent compositions, improvement can be made in granular soil removal, color clarification-, defuzzing, depilling and reduction of stiffness.

The detergent composition of the invention may also contain a surfactant (which may be anionic, nonionic, cationic, amphoteric or zwitterionic surfactant, or a mixture thereof). Further, the detergent composition of the invention may contain other detergent components known in the art, such as builders, bleaching agents, bleaching activators, corrosion inhibitors, sequestering agents, stain-dissociating polymers, aromatics, other enzymes, enzyme stabilizers, formulation assistants, fluorescent brightening agents, foaming promoters, etc. Examples of representative anionic surfactants include linear alkyl benzene sulfonate (LAS), alkylsulfate (AS), α-olefin sulfonate (AOS), alcohol ethoxy sulfate (AES) and alkali metal salts of natural fatty acids. Examples of nonionic surfactants include alkyl polyethylene glycol ether, nonylphenol polyethylene glycol ether, fatty acid esters of sucrose and glucose, and esters of polyethoxylated alkylglucoside.

It has been found that treating waste paper with the endoglucanase or the cellulase preparation of the invention can deink the paper. Thus, the use of the endoglucanase of the invention in the process of manufacturing recycled paper from waste paper can reduce ink-remaining fiber greatly to thereby improve the whiteness of the waste paper. Examples of waste paper which may be used in the invention include used printed paper such as used newspaper, used magazine paper and low-grade or middle-grade used printed paper containing mechanical pulp and chemical pulp; used woodfree paper composed of chemical pulp; and coated paper thereof. The term "deinking agent" used herein means those drugs commonly used in the deinking of waste paper, including alkali such as NaOH or $Na_2CO_3$ soda silicate, hydrogen peroxide, phosphates, anionic or nonionic surfactants, capturing agents such as oleic acid, pH stabilizers as aids, chelating agents, or dispersants.

According to the invention, it has also been found that treating paper pulp with the endoglucanase of the invention can significantly improve the freeness (drainage) of the pulp without remarkable reduction in its strength. Thus, the present invention provides a method of improving the freeness of paper pulp, comprising a step of treating the paper pulp with the endoglucanase or the cellulase preparation of the invention. Examples of pulp, which can be treated by the method of the invention, include waste paper pulp, recycled board pulp, kraft pulp, sulfite pulp or processed/thermally treated pulp, and other high-yield pulp.

Furthermore, the digestibility of glucans in animal feeds can be improved by using the endoglucanase of the invention in such feeds. Thus, the present invention provides a method of improving the digestibility of animal feeds, comprising a step of treating the animal feed with the endoglucanase or the cellulase preparation of the invention.

EXAMPLES

The present invention will be further described in detail by the following examples but is not limited thereto.
Endoglucanase Activity Hereinafter, endoglucanase activity means CMCase activity. Further, one unit of "CMCase activity" is defined as the amount of a cellulase enzyme which produces reducing sugars corresponding to one $\mu$mol of glucose per minute as determined by measuring amounts of the reducing sugars released from a solution of carboxymethyl cellulose (CMC, Tokyo Kasei Kogyo, Japan) after incubation with the enzyme for a certain period of time.

Example A1

Isolation and Purification of Endoglucanase Enzyme from *Rhizopus oryzae*

*Rhizopus oryzae* strain CP96001 (FERM BP-6889) was subjected to shaker cultivation in a medium (6.0% corn steep liquor, 3.0% wheat bran, 1.0% glucose, 0.5% $MgSO_4 7H_2O$, 0.15% $CaCO_3$) at 28° C. After incubation for 3 days, cells were removed out to provide a cultivation supernatant as a crude cellulase preparation.

An ammonium sulfate solution at a final concentration of 1.25 M was prepared from 80 ml of the crude cellulase preparation and applied at a flow rate of 3.4 ml/min to Macro-Prep Methyl HIC Support hydrophobic chromatography (25 ml in gel volume, BioRad Laboratories) which had been equilibrated with 1.25 M ammonium sulfate solution. It was then fractionated by eluting at a flow rate of 5.0 ml/min in a stepwise elution method in which the concentration of ammonium sulfate in deionized water was decreased by 0.25 M each from 1.25 M. Among the fractions, a portion of those fractions obtained at an ammonium sulfate concentration of 0.75 M was found to have a strong activity in the removal of fuzz from lyocell. Therefore, 50 ml of this fraction was isolated. By repeating 150 times the fractionation by Macro-Prep Methyl HIC Support hydrophobic chromatography, 12 l of the cultivation supernatant were treated to provide 7.5 l of active fractions.

An ammonium sulfate solution at a final concentration of 1.25 M was prepared from 7.5 l of the active fractions. Among them, 190 ml of the fractions were applied at a flow rate of 2.8 ml/min to Macro-Prep Methyl HIC Support hydrophobic chromatography (25 ml in gel volume, bioRad Laboratories), which had been equilibrated with 1.25 M ammonium sulfate solution. Then, 1.25 M and 1.125 M ammonium sulfate solutions were stepwise applied at a flow rate of 5.0 ml/min. The fractions then eluted with about 20 ml of deionized water were found to have a strong activity in the removal of fuzz from lyocell and therefore pooled. By repeating 40 times the fractionation by Macro-Prep Methyl HIC Support hydrophobic chromatography, 7.5 l of the active fractions obtained in the previous step were treated to provide 800 ml of active fractions.

Then, 800 ml of the active fractions were diluted 10 times with 50 mM acetate buffer (pH 4.0) to 8.0 l of a solution, 23 ml of which were applied at a flow rate of 0.9 ml/min to MonoS HR 5/5 cation chromatography (Pharmacia Biotech) that had been equilibrated with 50 mM acetate buffer (pH 4.0). It was then eluted with a linear gradient of Buffer A (50 mM acetate buffer, pH 4.0) and Buffer B (50 mM acetate buffer containing 1 M NaCl, pH 5.2) at a flow rate of 0.9 ml/min. Those fractions, which were found to have a strong activity in the removal of fuzz from lyocell were isolated. The fractionation by MonoS HR 5/5 cation chromatography was repeated 350 times to isolate a purified endoglucanase enzyme RCE I. This RCE I showed a single band in SDS-PAGE and had a molecular weight (MW) of about 40 kD. The SDS-PAGE used NPU-12.5L PAGEL (ATTO Japan) and migration and dyeing were carried out according to the specification attached to the gel. Molecular weight standards used were SDS-PAGE molecular weight standard Low range (BioRad Laboratories).

Example A2

Isolation and Purification of Endoglucanase Enzyme from *Mucor circinelloides*

*Mucor circinelloides* strain CP99001 (FERM BP-6890) was subjected to shaker cultivation in a medium (3.0% corn steep liquor, 3.0% wheat bran, 3.0% glucose, 0.5% $MgSO_4 7H_2O$, 0.15% $CaCO_3$) at 28° C. After incubation for 3 days, cells were removed out to provide a cultivation supernatant as a crude cellulase preparation.

An ammonium sulfate solution at a final concentration of 1.5 M was prepared from 120 ml of the crude cellulase preparation and applied at a flow rate of 3.0 ml/min to Macro-Prep Methyl HIC Support hydrophobic chromatography (25 ml in gel volume, BioRad Laboratories) which had been equilibrated with 1.5 M ammonium sulfate solution. It was then fractionated by eluting at a flow rate of 5.0 ml/min in a stepwise elution method in which the concentration of ammonium sulfate in deionized water was decreased by 0.3 M each from 1.5 M. Among them, those fractions obtained at an ammonium sulfate concentration of 0.6 M were found to have a strong activity in the removal of fuzz from lyocell. Therefore, 64.3 ml of this fraction was isolated. By repeating 14 times the fractionation by Macro-Prep Methyl HIC Support hydrophobic chromatography, 1710 ml of the cultivation supernatant was treated to provide 900 ml of active fractions.

An ammonium sulfate solution at a final concentration of 1.5 M was prepared from 300 ml of the active fractions and applied at a flow rate of 3.0 mil/min to Macro-Prep Methyl HIC Support hydrophobic chromatography (25 ml in gel volume, BioRad Laboratories) which had been equilibrated with 1.5 M ammonium sulfate solution. Then, 1.5 M and 0.9 M ammonium sulfate solutions were stepwise applied at a flow rate of 5.0 m/min. The fractions then eluted with about 30 ml of deionized water were found to have a strong activity in the removal of fuzz from lyocell and therefore pooled. By repeating 3 times the fractionation by Macro-Prep Methyl HIC Support hydrophobic chromatography, 900 ml of the active fractions obtained in the previous step were treated to provide 90 ml of active fractions.

Then, 90 ml of the active fractions were diluted 10 times with 50 mM acetate buffer (pH 4.0) to 900 ml of a solution, 150 ml of which were applied at a flow rate of 1.0 ml/min to MonoS HR 5/5 cation chromatography (Pharmacia Biotech) that had been equilibrated with 50 mM acetate buffer (pH 4.0). It was then eluted with a linear gradient of Buffer A (50 mM acetate buffer, pH 4.0) and Buffer B (50 mM acetate buffer containing 1 M NaCl, pH 5.2) at a flow rate of 1.0 ml/min. Those fractions, which were found to have a strong activity in the removal of fuzz from lyocell, were isolated. The fractionation by MonoS HR 5/5 cation chromatography was repeated 6 times to isolate a purified endoglucanase enzyme MCE I. This MCE I showed a single band in SDS-PAGE and had a molecular weight (MW) of about 41 kD. The SDS-PAGE used NPU-12.5L PAGEL (ATTO Japan) and migration and dyeing were carried out according to the specification attached to the gel. Molecular weight standards used were SDS-PAGE molecular weight standard Low range (BioRad Laboratories).

Example A3

Isolation and Purification of Endoglucanase Enzyme from *Phycomyces nitens*

*Phycomyces nitens* strain CP99002 (FERM BP-6891) was subjected to Jar fermentor cultivation in a medium (2.0% corn steep liquor, 3.0% wheat bran, 2.0% Sucrose, 1.0% Yeast extract, 0.05% $KH_2PO_4$, 0.03% $MgSO_4 7H_2O$, 0.15% $CaCl_2$, 0.01% Adecanol at 28° C., 220 rpm. After incubation for 3 days, the cultivation supernatant from which cells were removed out was concentrated 10 times through ultrafiltration using a membrane with a molecular weight digested of 5,000.

An ammonium sulfate solution at a final concentration of 1.5 M was prepared from. 120 ml of the ultrafiltrated concentrate and applied at a flow rate of 3.0 ml/min to Macro-Prep Methyl HIC Support hydrophobic chromatography (25 ml in gel volume, BioRad Laboratories) which had been equilibrated with 1.5 M ammonium sulfate solution. It was then fractionated by eluting at a flow rate of 5.0 ml/min in a stepwise elution method in which the concentration of ammonium sulfate in deionized water was decreased by 0.3 M each from 1.5 M. Among them, those fractions obtained at an ammonium sulfate concentration of 0.3 M were found to have a strong activity in the removal of fuzz from lyocell. Therefore, 66 ml of this fraction was isolated. By repeating 10 times the fractionation by Macro-Prep Methyl HIC Support hydrophobic chromatography, 1200 ml of the ultrafiltrated concentrate were treated to provide 660 ml of active fractions.

An ammonium sulfate solution at a final concentration of 1.5 M was prepared from 165 ml of the active fractions and applied at a flow rate of 3.0 ml/min to Macro-Prep Methyl HIC Support hydrophobic chromatography (25 ml in gel volume, BioRad Laboratories) which had been equilibrated with 1.5 M ammonium sulfate solution. Then, 1.5 M and 0.75 M ammonium sulfate solutions were stepwise applied at a flow rate of 5.0 ml/min. The fractions then eluted with about 30 ml of deionized water were found to have a strong activity in the removal of fuzz from lyocell and therefore pooled. By repeating 4 times the fractionation by Macro-Prep Methyl HIC Support hydrophobic chromatography, 660 ml of the active fractions obtained in the previous step were treated to provide 120 ml of active fractions.

Then, 120 ml of the active fractions were diluted 10 times with 50 mM acetate buffer (pH 4.0) to 1200 ml of a solution, 100 ml of which were applied at a flow rate of 1.0 m/min to MonoS HR 5/5 cation chromatography (Pharmacia Biotech) that had been equilibrated with 50 mM acetate buffer (pH 4.0). It was then eluted with a linear gradient of Buffer A (50 mM acetate buffer, pH 4.0) and Buffer B (50 mM acetate buffer containing 1 M NaCl, pH 5.2) at a flow rate of 1.0 ml/min. Those fractions, which were found to have a strong activity in the removal of fuzz from lyocell, were isolated. The fractionation by MonoS HR 5/5 cation chromatography was repeated 12 times to isolate a purified endoglucanase enzyme PCE I. This PCE I showed a single band in SDS-PAGE and had a molecular weight (MW) of about 45 kD. The SDS-PAGE used NPU-1.25L PAGEL (ATTO Japan) and migration and dyeing were carried out according to the specification attached to the gel. Molecular weight standards used were SDS-PAGE molecular weight standard Low range (BioRad Laboratories).

Example A4

Evaluation of Action of RCE I, MCE I and PCE I on Regenerated Cellulose Fabrics by Launder Meter Fuzz removal activity on lyocell, representative of regenerated cellulose fabrics, of the purified endoglucanase enzyme RCE I, MCE I and PCE I obtained in Examples A1 to A3 was evaluated in the following manner.

Dyed knitted fabric of lyocell (Toyoshima Japan) was fuzzed in a large washer containing surfactants and rubber balls. Thereafter, the fuzzy knitted fabric of lyocell (Toyoshima Japan, 9 cm×10 cm, about 2 g in weight) was cylindrically sewn and subjected to fuzz removal treatment with various enzymes under the conditions as set forth below. The protein concentrations of RCE I, MCE I and PCE I required to completely remove fuzz in the inside of the cylindrical fabric by the treatment were calculated.

The protein concentrations of various endoglucanases were calculated from the peak area at UV 280 nm of respective endoglucanase eluted with a linear gradient from 0% to 80% of acetonitrile concentration in 0.05% TFA (trifluoroacetic acid) at a flow rate of 1.0 m/min in HPLC analysis using TSK gel TMS-250 column (4.6 mm I.D.×7.5 cm, Toso Japan). The standard used was the purified NCE4 which was analyzed in HPLC under the same conditions, the protein concentration of which had been preliminarily measured by protein assay kit (BioRad Laboratories). The standard used to measure the protein concentration in the protein assay kit was albumin standard (Bovine serum albumin, fraction V, PIERCE). The purified NCE4 was isolated and purified from a cultivation broth of Humicola insolens according to the method as described in WO98/03640.

Test machine: Launder Meter L-12 (Daiei Kagaku Seiki MFG, Japan)
Reaction temperature: 55° C. for RCE I, and 50° C. for MCE I and PCE I
Time: 60 minutes
Reaction volume: 40 ml
Reaction pH: pH 5 (10 mM acetate buffer)
  pH 6 (10 mM acetate buffer)

The treating liquid contained 4 rubber balls (about 16 g each) together with the endoglucanase solution.
The results are shown in Table 1 below.

TABLE 1

| Enzyme | pH 5 | pH 6 |
| --- | --- | --- |
| RCE I | 0.5 mg/l | 0.5 mg/l |
| MCE I | 0.5 mg/l | 0.5 mg/l |
| PCE I | 1.4 mg/l | 0.9 mg/l |

Example A5

Evaluation of Action of RCE I, MCE I and PCE I on a Regenerated Cellulose Fabric at Different pH by Launder Meter Dyed fabric of lyocell (Toyoshima Japan) was fuzzed in a large washer containing surfactants and rubber balls. Thereafter, the fuzz removal treatment of lyocell was carried out with RCE I, MCE I and PCE I under the conditions as set forth below, and the protein concentrations of the various endoglucanases required to completely remove fuzz were calculated at each pH. The activity value at each pH is shown in the graph attached by its relative activity as compared with the activity value (100) in the pH region at which the highest activity was seen. As a control, the purified NCE4, which is the endoglucanase component from Humicola insolens disclosed in WO98/03640, was evaluated in a similar manner.

The protein concentrations of various endoglucanases were calculated from the peak area at UV 280 nm of respective endoglucanase eluted with a linear gradient from 0% to 80% of acetonitrile concentration in 0.05% TFA (trifluoroacetic acid) at a flow rate of 1.0 ml/min in HPLC analysis using TSK gel TMS-250 column (4.6 mm I.D.×7.5 cm, Toso Japan). The standard used was a purified NCE4 which was analyzed in HPLC under the same conditions, the protein concentration of which had been preliminarily measured by protein assay kit (BioRad Laboratories). The standard used to measure the protein concentration in the protein assay kit was albumin standard (Bovine serum albumin, fraction V, PIERCE).

Test machine: Launder Meter L-12 (Daiei Kagaku Seiki MFG. Japan)
Reaction temperature: 55° C. for NCE4 and RCE 1, and 50° C. for MCE I and PCE I
Time: 60 minutes
Reaction volume: 40 ml
Reaction pH: pH 4–6 (10 mM acetate buffer)
  pH 7–9 (10 mM Tris-HCl buffer)
  pH 9–10 (10 mM glycine-sodium hydroxide buffer)

The treating liquid contained 4 rubber balls (about 16 g each) together with the endoglucanase solution.
The results are shown in FIG. 1. As seen from the figure, the optimum pH for RCE 1, MCE I and PCE I is 5–7 and these enzymes in pH 5–8 possessed 70% or more of the activity at the optimum pH. On the other hand, the control NCE4 had an optimum pH of 5 and possessed only 30% or less of the activity at the optimum pH in the pH region of 6.2 or more. From these results, it is apparent that RCE I, MCE I and PCE I are significantly highly active in the alkaline conditions.

Example A6

Evaluation of Decoloring Activity of Denim Dyed Cellulose-containing Fiber by RCE I Twelve ounce desized blue jeans pants were subjected to decoloring treatment with the crude cellulase preparation and purified endoglucanase enzyme RCE I obtained in Example A1 under the following conditions.

Test machine: 20 kg Washer (Sanyo Denki Japan, full automatic washing machine SCW5101)
Temperature: 55° C.
Time: 60 minutes
pH: 6.2 (6.7 mM phosphate buffer)

The treating liquid contained an appropriate amount of rubber balls together with the cellulase preparation.

Decoloration was measured by using a spectrophotometer (Minolta, CM-525i). First, conditions for observation were set to be $D_{65}$ as a light source and 2° as a visual field for observation and calibration of L* value (lightness) in L*a*b* color system was effected according to the product manual. Next, the L* values in L*a*b* color system of various samples under the conditions were measured. An increase of L* value (increase in brightness) as compared with a control (untreated fiber), i.e., ΔL* value, was obtained and the degree of decoloration was evaluated by the ΔL* value. That is, ΔL* values were measured at 10 points in each test area (n=10) and an average was calculated. Then, the protein concentration of endoglucanase required to provide a ΔL* value of 7 was calculated.

The protein concentration was quantified using bovine serum albumin as a standard in protein assay kit (BioRad Laboratories).

The results are shown in Table 2 below.

TABLE 2

| Sample | Protein concentration |
| --- | --- |
| Crude cellulase preparation | 80.0 mg/l |
| RCE I | 2.0 mg/l |

Example A7

Weight Loss Processing Test of RCE I on Various Fabrics

Various cellulose-containing fabrics(15 cm×10 cm), the absolute dry weight of which had been preliminarily measured, were subjected to enzyme treatment under the following conditions.

Test machine: Launder Meter L-12 (Daiei Kagaku Seiki MFG. Japan)
Temperature: 55° C.
Time: 60 minutes
pH: 6 (10 mM acetate buffer)

The treating liquid contained an appropriate amount of stainless beads (Daiei Kagaku Seiki MFG. Japan) together with RCE I preparation (protein concentration of 8.0 mg/L). The protein concentration was quantified using bovine serum albumin as a standard in protein assay kit (BioRad Laboratories).

The absolute dry weights of fabric were measured before and after the enzyme treatment to calculate the weight loss percentage. The results are shown in Table below.

| Fabric tested | Weight reduction (%) |
| --- | --- |
| Cotion knit | 2.79 |
| Linen | 1.49 |
| Rayon | 2.83 |
| Polysonic | 11.32 |
| lyocell | 3.47 |

Example B1

Partial Amino Acid Sequences of RCE , MCE I and PCE I (1) Identification of N-terminal Amino Acid Residues In order to determine the N-terminal amino acid sequences of the purified proteins obtained in Examples A1 to A3, column chromatography (column: C8 220×2.1 mm, gradient of from 0.1% TFA, 5% acetonitrile to 0.085% TFA, 70% acetonitrile) was carried out in Model 172μ preparative HPLC system (Perkin Elmer) to further purify the target protein. It was subjected to protein sequencer Model 492 (Perkin Elmer) to determine the N-terminal amino acid sequence. The resulting sequences are as set forth below.

N-Terminal amino acid sequence of RCE I (SEQ ID NO:14):

```
Ala-Glu-(Cys)-Ser-Lys-Leu-Tyr-Gly-Gln-(Cys)-Gly-Gly-Lys-Asn-Trp-Asn-

*   *   *   *

Gly-Pro-Thr-(Cys)-(Cys)-Glu-Ser-Gly-Ser-Thr-(Cys)-Lys-Val-Ser-Asn-Asp-

*   *   *

Tyr-Tyr-Ser-Gln-(Cys)-Leu-Pro-Ser    (40 residues)
```

N-Terminal amino acid sequence of MCE I (SEQ ID NO:15):
Ala-Ser-(Cys)-Ser-Ser-Val-Tyr-Gly-Gln-(Cys)-Gly-Gly-Ile-Gly-Trp-Ser-Gly-Pro-Thr-(Cys)-(Cys)-Glu (22 residues)
N-Terminal amino acid sequence of PCE I (SEQ ID NO:16):
Ala-Glu-(Cys)-Ser-Gln-Gly-Tyr-Gly-Gln-(Cys)-Gly-Gly-Lys-Met-Trp-Thr-Gly-Pro-Thr-(Cys)-(Cys)-Thr-Ser (23 residues)

(2) Peptide Mapping

RCE I protein purified in (1) above was lyophilized and dissolved in 50 mM Tris-HCl buffer (pH 8.0). Lysyl endopeptidase (Wako Pure Chemical Japan) was added in an amount of about 1/100 mole per mole of protein and reacted at 37° C. for 48 hours. This cleavage product was subjected to column chromatography in the aforementioned HPLC system (column: C18 220×2.1 mm, gradient of from 0.1% TFA, 5% acetonitrile to 0.085% TFA, 35% acetonitrile) to isolate 5 peptides. The amino acid sequences of the resulting peptide fragments were determined by the aforementioned protein sequencer. The results are as set forth below.

LE-1: Asn-Ala-Asp-Asn-Pro-Ser-Met-Thr-Tyr-Lys (10 residues) (SEQ ID NO:38)
LE-2: Tyr-Ser-Ala-Val-Ser-Gly-Gly-Ala-Ser-Gly (10 residues) (SEQ ID NO:39)
LE-3: Ser-Ala-Ser-Asp-(Cys)-Ser-Ser-Leu-Pro-Ser-Ala-Leu-Gln-Ala-Gly-(Cys)-Lys (17 residues) (SEQ ID NO:40)
LE-4: Tyr-Gly-Gly-Ile-Ser-Ser-Ala-Ser-Asp-(Cys)-Ser-Ser-Leu-Pro-Ser-Ala-Leu-Gln (18 residues) (SEQ ID NO:4 1)
LE-5: Arg-Phe-Asn-Trp-Phe-Lys (6 residues) (SEQ ID NO:42)

Example B2

Isolation of Genomic DNA

The genomic DNAs were isolated in the following manner.

*Rhizopus oryzae* was cultivated in 30 ml of YPD liquid medium (1% yeast extract (Difco), 2% polypeptone (Wako Pure Chemical), 2% sucrose) at 30° C. for 40 hours, *Mucor circinelloides* was cultivated in 30 ml of YPD liquid medium (0.5% yeast extract (Difco), 2.4% potato dextrose broth (Difco), 2% sucrose) at 30° C. for 18 hours, and *Phycomyces nitens* was cultivated in 30 ml of YPD liquid medium (0.5% yeast extract (Difco), 2.4% potato dextrose broth (Difco), 2% sucrose) at 30° C. for 48 hours. Cells were collected from each cultivated broth through a glass filter. The resulting cells were lyophilized, finely crushed in a blender, and dissolved in 8 ml of TE (10 mM Tris-HCl (pH 8.0), 1 mM EDTA) buffer. 4 ml of TE buffer containing 10% SDS was added thereto and incubated at 60° C. for 30 minutes. Then, 12 ml of phenol-chloroform-isoamyl alcohol (25:24:1) was added and shaken vigorously. After centrifugation, the aqueous layer was transferred to another vessel, to which 1 ml of 5 M potassium acetate was added and allowed to stand in ice for one hour or more. After centrifugation, the aqueous layer was transferred to another vessel, to which 2.5 volumes of ethanol were added to precipitate DNA. The precipitate was dried, and then dissolved in 5 ml of TE buffer. Thereafter, 5 μl of 10 mg/ml ribonuclease A (RNase A) solution were added and incubated at 37° C. for one hour. Further, 50 μl of 20 mg/ml proteinase K solution were added and incubated at 37° C. for one hour. Thereafter, 3 ml of polyethylene glycol solution (20% PEG 6000, 2.5 M NaCl) were added to precipitate DNA. The precipitate was dissolved in 500 μl of TE buffer and extracted twice with phenol-chloroform-isoamyl alcohol followed by ethanol precipitation. The precipitate was washed with 70% ethanol, dried and dissolved in an appropriate amount of TE buffer to prepare a sample.

Example B3

Preparation of Long Chain Probe by PCR Method (1) Amplification of Target DNA Fragment by PCR Method As a DNA probe, a long probe was prepared which was amplified from the total DNA of Rhizopus oryzae as a template by PCR method.

As each primer, DNAs were synthesized which corresponded to the N-terminal amino acids and the amino acids of the peptide LE-5 marked by *. The prepared synthetic oligonucleotides had the following sequences:

Rh-N: AARAAYTGGAAYGGXCCNAC (20 mer) (SEQ ID NO:43)
Rh4.3a: TTRAACCARTRAANCG (17 mer) (SEQ ID NO:44)
Rh4.3b: TTRAACCARTTRAAYCT (17 mer) (SEQ ID NO:45)

wherein R is A or G; Y is C or T; N is A, G, C or T; and X is an inosine.

The PCR reaction was carried out under the following conditions: First, two sets of tubes, each of which contained 1 $\mu$M of each of Rh-N and Rh4.3a primers or 1 $\mu$M of each of Rh-N and Rh4.3b primers in addition to 1 $\mu$g of the genomic DNA of Rhizopus oryzae, were prepared and subjected to thermal denaturation at 95° C. for 2 minutes in the presence of dNTPs. Then, Taq polymerase (Recombinant Taq, Takara Shuzo) was added and the reaction conditions of 94° C. for 1 minute, 45° C. for 2 minutes and 72° C. for 3 minutes were repeated 25 times followed by incubation at 72° C. for 10 minutes. The PCR product was subjected to 0.8% agarose gel electrophoresis and the results showed that about 800 bp DNA was amplified only when Rh-N and Rh-4.3b were used as primers.

(2) Subcloning of PCR Product

The above mentioned about 800 bp DNA fragment amplified by PCR was recovered by using Sephaglas Band Prep Kit (Pharmacia Biotech) and ligated into pT7 Blue T-vector (Novagen) using DNA ligation kit (Takara Shuzo). The resulting ligation mixture was used to transform E. coli competent cells JM109 (Takara Shuzo). The resulting transformant was cultivated and plasmid DNA was recovered by the method described by ). Sambrock in "Molecular Cloning: A Laboratory Manual," 2nd Ed., ed. by Cold Spring Harbor Laboratory Press, New York, 1989, pp. 1.25–1.32. The obtained plasmid DNA was digested with plural restriction enzymes and subjected to 0.8% agarose gel electrophoresis to select those plasmid DNAs into which the about 800 bp fragment had been inserted. The plasmid into which a target PCR product was subcloned was designated as pRD05.

(3) Nucleotide Sequence Analysis of pRD05

The nucleotide sequence analysis was carried out in the following manner:

The apparatus for nucleotide sequence analysis used was A.L.F. DNA sequencer II (Pharmacia Biotech). The sequencing gel used was an acrylamide support available as Hydrolink Long Ranger (FMC). Various reagents for preparing a gel used (N,N,N',N'-tetramethyl ethylenediamine, urea, and ammonium persulfate) were reagents of A.L.F. grade (Pharmacia Biotech). Autoread Sequencing Kit (Pharmacia Biotech) was used in the nucleotide sequence reading reaction. The conditions for preparing a gel, the reaction conditions, and the electrophoretic conditions were set by referring to the details of each specification.

The template DNA, pRD05, was alkali denatured, annealed with universal and reverse primers attached to the Autoread Sequencing Kit, and subjected to elongation reaction. The reaction products were analyzed by a sequencer to reveal about 400 bp nucleotide sequences, respectively. Based on these results, FITC labeled sequencing primers described below and called RCE1-01 to 06 were prepared and reacted with pRD05 to further proceed with the sequencing. Consequently, the whole nucleotide sequence of the insert fragment of pRD05 was determined. The determined nucleotide sequence was translated into an amino acid sequence and one reading frame coincided with a portion of the partial amino acid sequence of endoglucanase RCE I described in Example B1. Thus, the insert DNA contained in the plasmid pRD05 was used as a probe for subsequent screening.

RCE-01: 5'-CAATGTCTTCCCTCTGGAAGCAG-3' (23 mer) (SEQ ID NO:46)
RCE-02: 5'-TGCCCTTAGTGACAGCAATGCCC-3' (23 mer) (SEQ ID NO:47)
RCE-03: 5'-CTTCCTTCCGCACTCCAAGCTGG-3' (23 mer) (SEQ ID NO:48)
RCE-04: 5'-CCAGCTTGGAGTGCGGAAGGAAG-3' (23 mer) (SEQ ID NO:49)
RCE-05: 5'-TCACTAAGGGCAGTGACACCATC-3' (23 mer) (SEQ ID NO:50)
RCE-06: 5'-CAGAGGGAAGACATTGAGAGTAG-3' (23 mer) (SEQ ID NO:51)

Example B4

Preparation of Genomic DNA Library (Sau3AI Library)

The Rhizopus oryzae genome DNA was digested with Sau3AI and subjected to 0.8% agarose gel electrophoresis using Agarosc LE (Nakarai Tesk Japan). After confirming that the genomic DNA was restrictedly digested in the range of 9 to 23 kbp, this DNA fragment was extracted and purified according to conventional methods. This DNA fragment was ligated into a phage vector, Lambda DASH II vector (Stratagene). After ethanol precipitation, the vector was dissolved in TE buffer and entirely packaged into the lambda head by using Giga Pack I Packaging Kit (Stratagene). Then, E. coli XLI-Blue strain MRA was infected with the resulting phage. The phage library ($5 \times 10^4$) obtained by this method was used to clone the target gene.

Example B5

Cloning of RCE I Gene (1) Screening by Plaque Hybridization

First, the plasmid pRD05 obtained in Example B3 was cleaved with BamHI and then subjected to 0.8% agarose gel electrophoresis to recover about 800 bp DNA fragments, which were in turn labeled by ECL Direct DNA/RNA labeling detection system (Amersham).

Then, the DNA genomic library (Sau3AI library) obtained according to Example B4 was transferred to a nylon membrane (Hybond N+ Nylon Transfer Membrane, Amersham). The DNA was fixed with 0.4N sodium hydroxide, washed with 5×SSC (1×SSC, 15 mM trisodium citrate, 150 mM sodium chloride), and dried to fix the DNA. According to the method of the kit, after prehybridization (42° C.) for 1 hour, the labeled probe was added and hybridization (42° C.) was carried out for 15 hours. Washing of the label was carried out according to the aforementioned specification attached to the kit. First, washing with 0.4% SDS, 0.5×SSC with 6M urea added at 42° C. for 20 minutes were repeated twice and then washing with 2×SSC at room temperature for 5 minutes were carried out twice. After washing the probe, the nylon membrane was immersed in the attached detection solution for 1 minute and then exposed to Fuji Medical X-ray film (Fuji Film) to yield two phage clones.

(2) Preparation of Phage DNA

E. coli strain XLI -Blue MRA was infected with the phage and, after 18 hours, phage particles were collected. These particles were treated with proteinase K and phenol according to the method of Grossberger (Grossberger, D., Nucleic Acids Res., 15, 6737 (1987)) and precipitated with ethanol to isolate phage DNAs.

(3) Subcloning of Target Gene

Two different phage DNAs were digested with plural restriction enzymes and subjected to 0.8% agarose gel electrophoresis. The DNAs were transferred to a nylon membrane by the method of Southern (Southern, E. M., J. Mol. Biol., 98:503–517, 1975) and hybridization was effected in the same manner as in Example B5 (1). As a result, the two phage DNAs showed a common hybridization pattern by digestion with the plural restriction enzymes. When the two phage DNAs were digested with XbaI, they were commonly hybridized with an about 3.5 kbp band. Therefore, this band was recovered and subcloned into the XbaI site of plasmid pUC119. The resulting plasmid was designated as pRCEI-Xba.

Example B6

Determination of Nucleotide Sequence of RCE I Gene

The nucleotide sequence was determined by the same method as in Example B3 (3). Thus, the reaction for analysis was carried out using the plasmid pRCEI-Xba obtained in Example B5 as the template DNA and FITC labeled sequencing primers of RCE 01 to 06 as the primers. Based on the results, the following FITC labeled sequencing primers designated as RCE1-07 to 09 were further prepared and each of them was reacted with the plasmid pRCEI-Xba to analyze and determine the whole nucleotide sequence of the endoglucanase RCE I gene.

RCE-07: 5'-ACAACATTATTTCTTCAAACATG-3' (23 mer) (SEQ ID NO:52)
RCE-08: 5'-AAATGCCGCATCAAGTTTTATTG-3' (23 mer) (SEQ ID NO:53)
RCE-09: 5'-TTCACTTCTACCTCTGTTGCTGG-3' (23 mer) (SEQ ID NO:54)

Example B7

Expression of RCE I Gene (1) Site-directed Mutagenesis of RCE I Gene

BglII site was introduced into the sites immediately upstream from the initiation codon and immediately downstream from the termination codon of RCE I gene by site-directed mutagenesis in the following manner.

First, two synthetic oligonucleotides pIN-Bgl and pIC-Bgl as set forth below as primers for mutagenesis were prepared and phosphorylated at 5' end using T4 polynucleotide kinase (Wako Pure Chemical).

Then, site-directed mutagenesis was carried out using Muta-Gene M 13 in vitro Mutagenesis Kit (BioRad Laboratory). Thus, E. coli strain CJ236 was transformed with plasmid pRCEI-Xba and infected with helper phage M13 KO7 to obtain single-stranded DNAs (ssDNAs). This pRCEI-Xba ssDNA was annealed with the phosphorylated primers pIN-Bgl and pIC-Bgl and subjected to polymerase reaction. The resulting double stranded DNA was introduced into E. coli strain JM109 to yield a mutant DNA. This mutagenized plasmid was designated as pRCEI-Bgl.

pIN-Bgl: 5'-GTAATAAACTFCATAGATCTATGTAAAA AGAATG-3' (34 mer) (SEQ ID NO:55)
pIC-Bgl: 5'-GGATGAGTATAAAAGATCTTATTTTC TTGAAC-3' (32 mer) (SEQ ID NO:56)

(2) Expression of RCE I Gene in Yeast

To express RCE I gene in yeast, the following investigations were done using the host-vector system as described in WO97/34004 specification.

Thus, the plasmid pRCEI-Bgl obtained in Example B7 (1) was digested with BglII and the RCE I gene was recovered. This gene was operably ligated into BamHI site, i.e., downstream from glyceraldehyde-3-phosphate dehydrogenase (GAP) promoter, of plasmid vector pY2831 to yield a plasmid pYRCEI. This plasmid was used to transform yeast (Saccharomyces cerevisiae) strain MS-161 (MATa, trpl, ura3) according to the abovementioned specification to yield a transformant in which the endoglucanase RCE I was capable of expression.

Example B8

Evaluation of RCE I Expressed in Yeast (1) Cultivation of Yeast Expressing RCE I The yeast transformed with the plasmid pYRCEI obtained in Example B7 was cultivated in SD liquid medium (0.67% Yeast nitrogen base w/o amino acids (Difco, 2% glucose) supplemented with 50 $\mu$g/ml uracil at 30° C. for 24 hours. The seed culture was seeded at a final concentration of 1% in SD liquid medium supplemented with 50 $\mu$g/ml uracil and 1% casamino acid and cultivated at 30° C. for 36 hours. After cultivation, yeast cells were removed by centrifugation to yield a crude enzyme solution, which was then used in various analyses.

(2) Measurement of Molecular Weight by SDS-PAGE

The crude enzyme solution obtained in Example B8 (1) was subjected to SDS-PAGE to detect a smear band having a molecular weight of about 100 to 200 kD.

(3) Evaluation of Yeast in which RCE I was Expressed (CMCase Activity)

The crude enzyme solution obtained in Example B8 (1) was used to measure CMCase activity. A cultivation broth of a strain transformed only with the vector DNA into which RCE I gene was not introduced was similarly treated and used as a control.

The results are shown in Table below.

|  | CMCase (U/ml) |
| --- | --- |
| RCE I gene recombinant | 1.270 |
| Control | 0.000 |

(4) Evaluation of Yeast in which RCE I was Expressed (Lyocell Fuzz Removal Activity)

The crude enzyme solution obtained in Example B8 (1) was dialyzed and the lyocell fuzz removal activity was measured at 55° C., pH 6 in the same manner as in Example A4. A cultivation broth of a strain transformed only with the vector DNA into which RCE I gene was not introduced was similarly treated and used as a control.

As a result, no fuzz removal activity was shown in the treatment with 0.5 ml broth/ml of the RCE I gene recombinant strain. Also, no fuzz removal activity was shown in the treatment with 0.5 ml broth/ml of the control reaction solution.

Example B9

Expression of Mutant Endoglucanase RCE I

In Example B8, the endoglucanase RCE I expressed in yeast showed CMCase activity but did not show lyocell fuzz removal activity. Further, the molecular weight measured in Example B8 (2) was higher than expected.

It has been reported by Van Arsdell et al. (Van Arsdell, J. N., 1987, Bio Technology, 5, 60–64) that overglycosylation (excessive addition of sugar chain) sometimes occurs when a foreign protein is expressed in yeast. It was believed that similar phenomenon had occurred in the expression of the endoglucanase RCE I in yeast in Example B8. Accordingly, to express endoglucanase RCE I showing lyocell fuzz removal activity in yeast, a mutant endoglucanase RCE I gene was created wherein amino acids were replaced at asparagine (Asn)-linked glycosylation sites.

(1) Site-directed Mutagenesis of RCE I Gene

It has been reported by Lehle et al. (Lehle, L. and Bause E., 1984, Biochim. Biophys. Acta., 799, 246–251) that recognition sites of Asn-linked glycosylation, Asn-X-Ser/Thr, are common between yeast and mammalian glycoproteins.

It was believed that endoglucanase RCE I gene has three such sequences and sugar chains bound to asparagine residues at 45th, 90th and 130th positions in the amino acid sequence of SEQ ID NO:1. To express a mutant endoglucanase RCE I which does not have Asn-linked glycosylation site in yeast, site-directed mutagenesis was performed in RCE I gene.

The site-directed mutagenesis was carried out according to the method of Example B7 (1). Thus, three synthetic oligonucleotides pIRI-S47A, pIRI-S92G and pIRI-N130D as set forth below were first prepared as mutagenesis primers and phosphorylated at 5' ends thereof.

Then, *E. coli* strain CJ236 was transformed with plasmid pRCEI-Bgl and a helper phage was used to obtain ssDNA. This ssDNA and primers were annealed and double-stranded through polymerase reaction using the aforementioned kit and introduced into *E. coli* strain JM109 to yield a mutant DNA, which was designated as pRCEI-NLCD.

pIRI-S47A: 5'-CACTTTCAGAAGCTTTATTGCCAC-3' (24 mer) (SEQ ID NO:57)

pIRI-S92G: 5'-GAGCTAGAGCCAGAGTTAGAAG-3' (22 mer) (SEQ ID NO:58)

pIRI-N130D: 5'-GAGAACTGACATCGGCCTTACC-3' (22 mer) (SEQ ID NO:59)

(2) Expression of Mutant Endoglucanase RCE 1 in Yeast

The mutant endoglucanase RCE I gene was expressed in yeast according to the method of Example B7 (2). Thus, the plasmid pRCEI-NLCD1 obtained in Example B9 (1) was digested with BglII and a mutant cellulase RCE I gene was recovered. This gene was operably linked to the BamHI site downstream from GAP promoter of plasmid vector pY2831 to yield a plasmid pYI-NLCD. This plasmid was used to transform yeast strain MS-161. Thus, a transformant was obtained in which the mutant endoglucanase RCE I was expressed.

Example B10

Evaluation of Mutant Endoglucanase RCE I Expressed in Yeast (1) Cultivation of Yeast Expressing Mutant RCE I The yeast transformed with the plasmid pYI-NLCD obtained in Example B9 was cultivated under the same conditions as in Example B8 (1) to yield a crude enzyme solution as a cultivation supernatant.

(2) Measurement of Molecular Weight by SDS-PAGE

The crude enzyme solution obtained in Example B10 (1) was subjected to SDS-PAGE to detect a smear band having a molecular weight of about 40 to 45 kD.

(3) Evaluation of Yeast in which Mutant RCE I was Expressed (CMCase Activity)

The crude enzyme solution obtained in Example B10 (1) was used to measure CMCase activity. A cultivation broth of a strain transformed only with the vector DNA into which the mutant RCE I gene was not introduced was similarly treated and used as a control.

The results are shown in Table below.

|  | CMCase (U/ml) |
| --- | --- |
| Mutant RCE I gene recombinant | 1.100 |
| Control | 0.000 |

(4) Evaluation of Lyocell Fuzz Removal Activity of Mutant RCE I Expressed in Yeast The crude enzyme solution obtained in Example B10 (1) was dialyzed and the lyocell fuzz removal activity was measured at 55° C., pH 6 in the same manner as in Example A4. As a control, a cultivation broth of a strain transformed only with the vector DNA into which the mutant RCE I gene was not introduced was similarly treated and evaluated.

As a result, 80% of fuzz was removed when treated with 0.1 ml broth/ml of the reaction solution obtained from the mutant RCE I gene recombinant strain. On the other hand, no fuzz was removed when treated with 0.5 ml broth/rnl of the control reaction solution.

These results showed that, in order to express RCE I in yeast while exhibiting lyocell fuzz removal activity in yeast, it is necessary to replace amino acids so that RCE I does not have Asn-linked glycosylation site. The amount of protein required to completely remove fuzz was measured by the degree of dyeing after SDS-PAGE. As a result, the mutant endoglucanase RCE I expressed in yeast was almost identical with the endoglucanase RCE I purified by the method shown in Example A1.

(5) Evaluation of Lyocell Fuzz Removal Activity at Various pHs of Mutant RCE I Expressed in Yeast The crude enzyme solution obtained in Example B10 (1) was used to measure lyocell fuzz removal activity was measured at pH 4 to 9 in the same manner as in Example A5.

The results are shown in FIG. 2. As seen from the figure, the optimum pH of the mutant RCE I was 7 to 8 and it possessed 80% or more of the activity at the optimum pH over the range of pH 5.2 to 8.6. It is clear that the mutant RCE I expressed in yeast shows similar pH properties as compared with RCE I purified from *Rhizopus oryzae*.

Example C1

Search for Homologs of RCE I Gene in *Rhizopus oryzae*

To search for homologs of endoglucanase RCE I gene in genomic DNA of *Rhizopus oryzae*, analysis was carried out by Southern hybridization.

First, about 10 μg of genomic DNA of *Rhizopus oryzae* obtained according to Example B2 was digested with plural restriction enzymes (EcoRI, BamHI, HindIII, SacI, XbaI, SalI, etc.) and subjected to 0.8% agarose gel electrophoresis. These materials were transferred to a membrane according to Example B5 (3) and hybridized under the same conditions as in the aforementioned examples. As a result, in addition to the endoglucanase RCE I gene, at least 2 homologous genes were found to be present on the genomic DNA of *Rhizopus oryzae*. These three genes including RCE I gene were detected as a single band respectively, in particular in the hybridization when the genomic DNA was digested with SacI. Accordingly, the gene detected as a band of about 3 kbp (RCE II gene) and the gene detected as a band of about 10 kbp (RCE III gene) were subjected to subsequent cloning.

Example C2

Cloning of Endoglucanase RCE II Gene
(I) Preparation of Genomic DNA Library (for Cloning RCE II Gene)

The *Rhizopus oryzae* genome DNA was digested with SacI and subjected to 0.8% agarose gel electrophoresis using Agarose LE to extract and purify DNA fragments of 2 to 4 kbp in size according to conventional methods. This DNA fragment was ligated into a phage vector, Lambda ZAP II vector (Stratagene) and packaged in the same manner as in Example B4. *E. coli* strain XLI-Blue MRF' was infected with the resulting phage. The phage library ($1 \times 10^5$) obtained by this method was used to clone RCE II gene.
(2) Cloning of RCE II Gene Screening by plaque hybridization was carried out using the library obtained in Example C2 (1) and the long chain probe obtained in Example B3. Hybridization was carried out under the same conditions as in Example B5 to yield three phage clones.

*E. coli* strain XL1-Blue MRF' was infected with the resulting phage and DNAs were prepared according to the method of Example B5 (2), digested with SacI and subjected to 0.8% agarose gel electrophoresis. The DNAs were transferred to a nylon membrane by the method of Example B5 (3) and hybridized. As a result, a common band having the same size of about 3 kbp as the genomic DNA was detected in the three phage DNAs. This band was recovered and subcloned into the SacI site of plasmid pUC118. The resulting plasmid was designated as pRCEII-Sac.

Example C3

Determination of Nucleotide Sequence of Endoglucanase RCE II Gene

The nucleotide sequence was determined by the same method as in Example B3 (3). Thus, the reaction for analysis was carried out using the plasmid pRCEII-Sac obtained in Example C2 as the template DNA and the FITC labeled sequencing primers of RCE 03, 04 and 05 prepared in Example B3 (3) as the primers. Based on the results, new FITC labeled sequencing primers were prepared and reacted with the plasmid pRCEII-Sac to further sequence. From the results, the following primers were further prepared to proceed with sequencing. Thus, the nucleotide sequence of RCE II was determined.

RCEII-01: 5'-ACAACATTATTTCTTCGAATATG-3' (23 mer) (SEQ ID NO:60)
RCEII-02: 5'-TTTAGCAGCAGAGGCCATTTCAG-3' (23 mer) (SEQ ID NO:61)
RCEII-03: 5'-TTTTCTATCCTGATACAGAGATG-3' (23 mer) (SEQ ID NO:62)
RCEII-04: 5'-GCGCTCATAAAACGACTACTACC-3' (23 mer) (SEQ ID NO:63)
RCEII-05: 5'-TGCCCTTAGTGACAGCAATGTCC-3' (23 mer) (SEQ ID NO:64)

Example C4

Expression of Endoglucanase RCE II Gene
(I) Site-directed Mutagenesis of RCE II Gene BglII site was introduced into the sites immediately upstream from the initiation codon and immediately downstream from the termination codon of RCE II gene by site-directed mutagenesis. The method of site-directed mutagenesis followed Example B7 (1).

First, a synthetic oligonucleotide pIIC-Bgl as set forth below as a primer for mutagenesis was newly prepared and phosphorylated at 5' end together with pIN-Bgl previously synthesized in Example B7 (1).

Then, the pRCEII-Sac was brought into single-strand in *E. coli* strain CJ236 and reacted with the phosphorylated primer to yield a mutant DNA. This mutagenized plasmid was designated as pRCEII-Bgl.

pIIC-Bgl:
  5'-CAAGAAAATAAGATCTTTTATACTCCTACT-3'
  (30 mer) (SEQ ID NO:65)

(2) Expression of RCE II Gene in Yeast

Expression of RCE II gene in yeast was carried out according to the method of Example B7 (2). Thus, the plasmid pRCEII-Bgl obtained in Example C4 (1) was digested with BglII and the endoglucanase RCE II gene was recovered. This gene was operably ligated into BamHI site, i.e., downstream from glyceraldehyde-3-phosphate dehydrogenase (GAP) promoter, of plasmid vector pY2831 to yield a plasmid pYRCEII. This plasmid was used to transform yeast (*Saccharomyces cerevisiae*) strain MS-161 (MATa, trp1, ura3) according to WO97/34004 specification to yield a transformant in which the endoglucanase RCE II was capable of expression.

Example C5

Evaluation of Endoglucanase RCE II Expressed in Yeast
(1) Cultivation of Yeast Expressing RCE II The yeast transformed with the plasmid pYRCEII obtained in Example C4 was cultivated under the same conditions as in Example B8 (1) to yield a crude enzyme solution as a cultivation supernatant.
(2) Measurement of Molecular Weight by SDS-PAGE The crude enzyme solution obtained in Example C4 (1) was subjected to SDS-PAGE to detect a smear band having a molecular weight of about 100 to 200 kD.
(3) Evaluation of Yeast in which RCE II was Expressed (CMCase Activity)

The crude enzyme solution obtained in Example C4 (1) was used to measure CMCase activity. A cultivation broth of a strain transformed only with the vector DNA into which RCE II gene was not introduced was similarly treated and used as a control.

| | CMCase (U/ml) |
|---|---|
| RCE II gene recombinant | 0.260 |
| Control | 0.000 |

(4) Evaluation of Lyocell Fuzz Removal Activity by Mutant RCE II Expressed in Yeast The crude enzyme solution obtained in Example C5 (1) was dialyzed and the lyocell fuzz removal activity was measured at 55° C., pH 6 in the same manner as in Example A4. A cultivation broth of a strain transformed only with the vector DNA into which RCE II gene was not introduced was similarly treated and used as a control.

As a result, no fuzz removal activity was shown in the treatment with 0.5 ml broth/ml of the reaction solution of RCE II gene recombinant strain. Also, no fuzz removal activity was shown in the treatment with 0.5 ml broth/ml of the control reaction solution.

Example C6

Expression of Mutant Endoglucanase RCE II

In Example C4, the endoglucanase RCE II expressed in yeast showed CMCase activity but did not show lyocell fuzz removal activity. Further, the molecular weight measured in Example C4 (2) was higher than expected. It was believed that these results were due to the excessive addition of Asn-linked glycosylation, like the case of RCE I. Accordingly, to express endoglucanase RCE II showing lyocell fuzz removal activity in yeast, a mutant endoglucanase RCE II gene was created wherein amino acids were replaced at asparagine-linked (Asn-type) glycosylation sites.

(1) Site-directed Mutagenesis of RCE II Gene

It was believed that RCE II gene has five recognition sites of Asn-linked glycosylation, Asn-X-SerFhr sequence, and sugar chains bound to asparagine residues at 45th, 92nd, 119th, 122nd and 158th positions in the amino acid sequence of SEQ ID NO:3. To express a mutant endoglucanase RCE II which does not have Asn-linked glycosylation in yeast, site-directed mutagenesis was performed in RCE II gene.

The site-directed mutagenesis was carried out according to the method of Example B7 (1). Thus, four synthetic oligonucleotides pIRII-S47A, pIRII-N92Q, pIRII-S121L:N122D and pIRII-N158D as set forth below were first prepared as mutagenesis primers and phosphorylated at 5' ends thereof.

Then, *E. coli* strain CJ236 was transformed with plasmid pRCEII-Bgl and a helper phage was used to obtain ssDNA. This ssDNA and primers were annealed and double-stranded through polymerase reaction using the aforementioned kit and introduced into *E. coli* strain JM109 to yield a mutant DNA, which was designated as pRCEII-AQLDD.

pIRII-S47A:
  5'-AACGGCAATAAGGCCTCTGAATGTAGC-3' (27 mer) (SEQ ID NO:66)
pIRII-N92Q:
  5'-GAAAGCAATGGCCAGAAAACTTCTGAAAG-3' (29 mer) (SEQ ID NO:67)
pIRII-S121L:N122D:
  5'-GCTTCAAACTCTCTAGACTCTAGCGGC-3' (27 mer) (SEQ ID NO:68)
pIRII-N158D: 5'-CGGTAAGGCCGACGTCAGTTCTCC-3' (24 mer) (SEQ D NO:69)

(2) Expression of Mutant Endoglucanase RCE II in Yeast

The mutant endoglucanase RCE II gene was expressed in yeast according to the method of Example B7 (2). Thus, the plasmid pRCEII-AQLDD1 obtained in Example C6 (1) was digested with BglII and a mutant endoglucanase RCE II gene was recovered. This gene was operably linked to the BamHI site downstream from GAP promoter of plasmid vector pY2831 to yield a plasmid pYII-AQLDD. This plasmid was used to transform yeast strain MS-161. Thus, a transformant was obtained in which the mutant endoglucanase RCE II was expressed.

Example C7

Evaluation of Mutant Endoglucanase RCE II Expressed in Yeast (i) Cultivation of Yeast Expressing Mutant RCE II The yeast transformed with the plasmid pYII-AQLDD obtained in Example C6 was cultivated under the same conditions as in Example B8 (1) to yield a crude enzyme solution as a cultivation supernatant.

(2) Measurement of Molecular Weight by SDS-PAGE

The crude enzyme solution obtained in Example C7 (1) was subjected to SDS-PAGE to detect a smear band having a molecular weight of about 45 kD.

(3) Evaluation of Mutant RCE II Expressed in Yeast (CMCase Activity)

The crude enzyme solution obtained in Example C7 (1) was used to measure CMCase activity. A cultivation broth of a strain transformed only with the vector DNA into which the mutant RCE II gene was not introduced was similarly treated and used as a control.

| | CMCase (U/ml) |
|---|---|
| Mutant RCE II gene recombinant | 0.210 |
| Control | 0.000 |

(4) Evaluation of Lyocell Fuzz Removal Activity by Mutant RCE II Expressed in Yeast The crude enzyme solution obtained in Example C7 (1) was used to measure the lyocell fuzz removal activity at 55° C., pH 6 in the same manner as in Example A4. A cultivation broth of a strain transformed only with the vector DNA into which the mutant RCE II gene was not introduced was similarly treated and used as a control.

As a result, 60% of fuzz was removed when treated with 0.2 ml broth/ml of the reaction solution of the mutant RCE II gene recombinant strain. On the other hand, no fuzz was removed when treated with 0.5 ml broth/ml of the control reaction solution.

From the above, it was shown that, in order to express RCE II exhibiting lyocell fuzz removal activity in yeast, it is necessary to replace amino acids so that RCEII does not have Asn-linked glycosylation site, as in the case of RCE I. Further, the amount of protein required to completely remove fuzz was measured by the degree of dyeing after SDS-PAGE. As a result, the mutant endoglucanase RCE II expressed in yeast was almost identical with the endoglucanase RCE I purified by the method shown in Example A1.

Example C8

Cloning of Endoglucanase RCE III Gene (1) Preparation of Genomic DNA Library (for Cloning RCE III Gene)

The *Rhizopus oryzae* genome DNA was digested with SacI and subjected to 0.8% agarose gel electrophoresis using Agarose LE to extract and purify DNA fragments of about 10 kbp in size according to conventional methods. This DNA fragment was ligated into Lambda DASH II vector and packaged in the same manner as in Example B4. *E. coli* strain XL1-Blue MRA was infected with the resulting phage. The phage library (1×10$^5$) obtained by this method was used to clone RCE III gene.

(2) Cloning of RCE III Gene

Screening by plaque hybridization was carried out using the library obtained in Example C8 (1) and the long chain probe obtained in Example B3. Hybridization was carried out under the same conditions as in Example B5 to yield two phage clones.

*E. coli* strain XL1-Blue MRA was infected with the resulting phage and DNAs were prepared according to the method of Example B5 (2). They were digested with plural restriction enzymes and subjected to 0.8% agarose gel electrophoresis. The DNAs were transferred to a nylon membrane according to the method of Example B5 (3) and hybridized. As a result, a common band having the same size as the genomic DNA was detected in the two phage DNAs. In particular, a single band of about 10 kbp or about 2 kbp in size was found in SacI or BamHI cleavage, respectively. Accordingly, the band of about 2 kbp obtained by BamHI cleavage was recovered and subcloned into the BamHI site of plasmid pUC118. The resulting plasmid was designated as pRCEIII-Bam.

Example C9

Determination of Nucleotide Sequence of Endoglucanase RCE III Gene

The nucleotide sequence was determined in the same manner as in Example B3 (3). Thus, the reaction for analysis was carried out using the plasmid pRCEM-Bam obtained in Example C8 as the template DNA and the reverse primer attached to the kit and FITC labeled sequencing primer RCE-06 as the primers. Based on the results, new FITC labeled sequencing primers were prepared and reacted with the plasmid pRCEIII-Bam to further sequence. By further repeating this procedure, the nucleotide sequence of RCE III was determined. The prepared FITC sequencing primers were as follows.

RCEIII-01: 5'-TACAGGAGCCAACAGGGGAGGTG-3' (23 mer) (SEQ ID NO:70)
RCEIII-02: 5'-TTCACAGCAGGTAGGTCCATTCC-3' (23 mer) (SEQ ID NO:71)
RCEIII-03: 5'-CCTACGGTTTCGCCGCTGCTTCC-3' (23 mer) (SEQ ID NO:72)
RCEIII-04: 5'-TAGATACCAACACCACCACCGGG-3' (23 mer) (SEQ ID NO:73)
RCEIII-05: 5'-TGAAGTTCCTTACCATTGCCTCC-3' (23 mer) (SEQ ID NO:74)
RCEIII-06: 5'-TGGTGAAACCACTCGCTACTGGG-3' (23 mer) (SEQ ID NO:75)
RCEIII-07: 5'-TTCTGCCTCTGACTGTTCTAACC-3' (23 mer) (SEQ ID NO:76)
RCEIII-08: 5'-AATAGAGTTACTCTATACGATAG-3' (23 mer) (SEQ ID NO:77)
RCEIII-09: 5'-CACCACCAGAGACAGCGGAGTAG-3' (23 mer) (SEQ ID NO:78)
RCEIII-10: 5'-TGCGTTGATTATCCTGACAATCC-3' (23 mer) (SEQ ID NO:79)

Example C10

Expression of Endoglucanase RCE III Gene (1) Site-directed Mutagenesis of RCE III Gene BamHI site was introduced into the sites immediately upstream from the initiation codon and immediately downstream from the termination codon of RCE III gene by PCR method in the following manner. First, synthetic oligonucleotides pIIIC-Bam1 and pIIIC-Bam2 as set forth below as primers for mutagenesis were newly prepared. PCR was carried out using the plasmid pRCEIII-Bam previously obtained in Example C8 as a template, pIIIC-Bam1 and pIIIC-Bam2 to yield a mutant DNA. This mutant DNA was digested with BamHI and the resulting DNA fragments were recovered and subcloned into BamHl site of the plasmid pUC118. The resulting mutagenized plasmid was designated as pRCEM-Bam2.

pIIIC-Bam1:
  5'-GCGGATCCATGAAGTTCCTTACCATTGCC-3' (29 mer) (SEQ ID NO:80)
pIIIC-Bam2:
  5'-GCGGATCCTTATTMCTTGAACAGCCAGA-3' (29 mer) (SEQ ID NO:81)

It was believed that RCE III gene had four recognition sites of Asn-linked glycosylation, Asn-X-Ser/Thr sequence, and sugar chains bound to asparagine residues at 44th, 49th, 121st and 171st positions in the amino acid sequence of SEQ ID NO:5. Accordingly, to express while showing the lyocell fuzz removal activity in yeast, two mutant RCE III genes were prepared, that is, one in which the amino acid at 44th Asn-linked glycosylation site was replaced so that the site was not glycosylated, and the other one in which both the amino acids at 44th and 121 st Asn-linked glycosylation sites were replaced so that the sites were not glycosylated.

The site-directed mutagenesis was carried out according to the method of Example B7 (1). Thus, two synthetic oligonucleotides pIRIII-N44D and pIRIII-N121K as set forth below were first prepared as mutagenesis primers and phosphorylated at 5' ends thereof. Then, *E. coli* strain CJ236 was transformed with the plasmid pRCEIII-Bam2 and a helper phage was used to obtain ssDNAs. These ssDNA and primers were annealed and double-stranded through polymerase reaction using the aforementioned kit and introduced into *E. coli* strain JM109 to yield mutant DNAs. The mutagenized plasmid in which only the 44th amino acid had been replaced was designated as pRCEIII-D, and the mutagenized plasmid in which both the 44th and 121st amino acids had been replaced was designated as pRCEIII-DK.

pIRIII-N44D:
  5'-GTGGAGGTGAGATCTTCATTGGGAAC-3' (26 mer) (SEQ ID NO:82)
pIRIII-N121K: 5'-CAGCGGAGTACTTTGTAGAAGCAG-3' (24 mer) (SEQ ID NO:83)

(2) Expression of Mutant Endoglucanase RCE m in Yeast

The mutant RCE III gene was expressed in yeast according to the method of Example B7 (2). Thus, the two plasmids pRCEIII-D and pRCEIII-DK obtained in (1) above were digested with BamHI and mutant RCE III genes were recovered. These genes were operably linked to the BamHI site downstream from GAP promoter of plasmid vector pY2831 to yield two plasmids pYIII-D and pYIII-DK. These plasmids were used to transform yeast strain MS-161. Thus, transformants were obtained in which the mutant endoglucanase RCE III was expressed.

Example C11

Evaluation of Mutant Endoglucanase RCE III Expressed in Yeast (1) Cultivation of Yeast Expressing Mutant RCE III The yeast transformed with each of the two plasmids pYIIII-D and pYIII-DK obtained in Example C10 was cultivated under the same conditions as in Example B8 (1) to yield a crude enzyme solution as a cultivation supernatant.

(2) Evaluation of Mutant RCE III Expressed in Yeast (CMCase Activity)

The crude enzyme solution of the yeast transformed with pYIIII-DK which was obtained in Example C11 (1) was used to measure CMCase activity. A cultivation broth of a strain transformed only with the vector DNA into which the mutant RCE III gene was not introduced was similarly treated and used as a control.

|  | CMCase (U/ml) |
| --- | --- |
| Mutant RCE III gene recombinant | 0.472 |
| Control | 0.000 |

(3) Evaluation of Lyocell Fuzz Removal Activity by Mutant RCE III Expressed in Yeast The two crude enzyme solutions of yeasts transformed with pYIII-D and pYIII-DK which were obtained in Example C11 (1) were dialyzed and then used to measure the lyocell fuzz removal activity at 55° C., pH 6 in the same manner as in Example A4. A cultivation broth of a strain transformed only with the vector DNA into which the mutant RCE III gene was not introduced was similarly treated and used as a control.

As a result, 60% of fuzz was removed by the treatment with 0.2 ml broth/ml of the reaction solution of the mutant RCE III gene recombinant strain (pYIII-D transformant), while 80% of fuzz was removed by the treatment with 0.2 ml broth/ml of the reaction solution of the mutant RCE III gene recombinant strain (pYIII-DK transformant). On the other hand, no fuzz was removed when treated with 0.5 ml broth/ml of the control reaction solution. These results suggested even those in which only amino acid(s) at the nearest Asn-linked glycosylation site(s) from the cellulose binding domain was/were replaced could exhibit lyocell fuzz removal activity.

Example D1

Expression of Endoglucanase RCE I Gene in *Humicola insolens* (I)

(1) Site-directed Mutagenesis of RCE I Gene

Mutagenesis of the sequence immediately upstream from the initiation codon of RCE I gene was conducted using PCR method so as to be suitable for expression in *Humicola insolens*. First, a synthetic oligonucleotide pRIN-Bgl as set forth below was newly prepared as a primer for mutagenesis. The PCR was effected using the plasmid pRCEI-Bgl previously obtained in Example B7 (1) as a template, pRIN-Bgl and the synthetic oligonucleotide pIC-Bgl obtained in Example B7 (1), and the amplified fragment of about 1 kB was subcloned into pT7 Blue-T vector. The resulting mutagenized plasmid was designated as pHRCEI-Bgl-11.

The sequence of the oligonucleotide primer prepared upon the mutagenesis is shown below.

pRIN-Bgl: 5'-GGGAGATCTTGGGACAAGATGAAGT TTATTA CTATTG-3' (37 mer) (SEQ ID NO:84)

(2) Preparation of Plasmid pJRID01 a) Preparation of plasmid pM21-m-A1:

The expression vector pJRID 15 of RCE I gene in *Humicola insolens* was constructed in the following manner. First, plasmid pM21 obtained according to WO98/03667 was subjected to site-directed mutagenesis using a synthetic oligonucleotide pMN-Bam. The resulting mutagenized plasmid was designated as pM21-m-A1.

The sequence of the oligonucleotide primer prepared upon mutagenesis is shown below.

pMN-Bam: 5'-GGTCAAACAAGTCTGTGCGGATCCTGGGACAA GATGGCCAAGTTCTTCCTTAC-3' (53 mer) (SEQ ID NO:85)

b) Preparation of pJD01:

First, plasmid pM21-m-A1 was digested with HindIII and BamHI and DNA fragment of about 1 kbp was recovered. Then, plasmid pMKD01 obtained according to WO98/03667 was digested with HindIII and BamHI and DNA fragment of about 7 kbp was recovered. Finally, these DNA fragments were ligated and the resulting plasmid was designated as pJD01.

c) Preparation of Plasmid pJRID01:

Plasmid pJD01 was digested with BamHI and then dephosphorylated with alkaline phosphatase (Takara Shuzo). Then, the plasmid pHRCEI-Bgl-11 obtained in (1) above was digested with BamHI and DNA fragment of about 1 kbp was recovered. And, these DNAs were operably linked and the resulting plasmid was designated as pJRID01.

(3) Transformation of *Humicola insolens* with Plasmid pJRID01

According to the method described in WO98/03667, *Humicola insolens* MN200-1 was transformed with plasmid pJRID01 and 50 strains showing hygromycin resistance were selected.

Example D2

Expression of Endoglucanase RCE I Gene in *Humicola insolens* (II)

(I) Cultivation of Transformant with Plasmid pJRID01 and evaluation by SDS-PAGE According to the method described in WO98/03667, 50 transformants with plasmid pJRID01 were cultivated in (N) medium at 37° C. for 4 days. The resulting cultivation supernatant was analyzed by SDS-PAGE but no protein band that increased as compared with the recipient strain was detected.

(2) Evaluation by Lyocell Fuzz Removal Activity of Transformants with Plasmid pJRID01

The cultivation supernatant of 50 transformants with plasmid pJRD01 obtained in (1) above was used to measure lyocell fuzz removal activity. The method followed Example A4 and measurements were done at pH 6, 55° C. As a result, any of the transformants only exhibited lyocell fuzz removal activity substantially similar to the untransformed recipient strain.

Example D3

Expression of Codon Optimized Endoglucanase RCE I Gene in *Humicola insolens* (I)

From the results of Example D2, endoglucanase RCE I gene derived from *Rhizopus oryzae* was scarcely expressed in *Humicola insolens*. It was believed to be due to a large difference in codon usage between genes derived from *Rhizopus* belonging to Zygomycetotina and those derived from *Humicola* belonging to Deuteromycotina. FIG. 3 shows the codon usage of endoglucanase RCE I gene. RCE I relatively frequently uses A and T as the third letter in codons. On the contrary, cellulase gene NCE I (as described in Japanese Patent Application Laying Open No. 8-56663), NCE 2 (as described in Japanese Patent Application Laying Open No. 8-126492) and NCE 4 (as described in WO98/03640) derived from *Humicola* frequently use G and C as the third letter in codons. Accordingly, it was believed that, in order to express RCE I gene derived from *Rhizopus* in *Humicola*, it was necessary to optimize the codon usage to *Humicola*, more particularly to replace A and T, when used as the third letter in codons, with G and C without changing amino acids encoded thereby. Further, it was believed that, in order to improve stability of mRNA, transcription product of a target gene, it was necessary to not only change the third letters in codons to G and C but also to select such a sequence that does not contain intron recognition sequence, in more particular, such DNA sequences as GTAGN, GTATN, GTAAN, GTACGN, GTGTN, GCACGN and GTTCGN. Thus, codon optimized endoglucanase RCE I gene satisfying the above conditions was designed and fully synthesized as mentioned hereinafter.

(1) Full Synthesis of Codon Optimized Endoglucanase RCE I Gene a) Preparation of Plasmid p12-B1:

First, two synthetic oligonucleotides having the following sequences were prepared.

RCE I-01: 5'-GGGGGATCCTGGGACAAGATGAAGT TCATCACTATCGCCTCCTCCGCCCTCCTTGCCCT CGCCCTTGGCACTGAGATGGCCTCCGC- CGCTGAGTGCTCCAAGCTCTACGGCCAGTGCGG CGGAAAGAACTGG-3' (132 mer) (SEQ D NO:86)

RCE I-02: 5'-GGCCGACTCGCTCGACTTGTTTCCCGA GGAGCCGCTCGGCAGGCACTGGCTGTAGTAGT CATTCGAGACCTTGCAGGTCGAGCCGCTCT CGCAGCA GGTGGGGCCGTTCCAGTTCTTTCCGC- CGCAC TGGCCGTAG-3' (136 mer) (SEQ ID NO:87)

Then, these oligonucleotides were used to carry out PCR reaction. LA PCR kit (Takara Shuzo) was used in the PCR reaction. dNTP and buffer were added to RCE I-10 and RCE I-02, each 1 μM, incubated at 94° C. for 10 minutes, and ice cooled for 5 minutes. Thereafter, LA Taq polymerase was added and the cycle reaction of 94° C. for 30 seconds, 55 C for 30 seconds and 72° C. for 1 minute and 45 seconds was repeated 20 times, followed by incubation at 72° C. for 10 minutes. The amplified DNA of about 200 bp was subcloned into pT7 Bleu T-vector according to the method described in Example B3. The resulting plasmid was designated asp p12-BI.

b) Preparation of plasmid p123-6:

First, a synthetic oligonucleotide having the following sequence was prepared.

RCE I-P335-Xho-C: 5'-GGGCTCGAGTTGGACGGA GTCAAGCCTTGGCGACGGTCGTGGTCTCTTGG CGGGAGCGGTCGTAGTCTTCTTGTGAGCGGCGG TCGTGGTCTTCTTGTGGGCAGCGGTCGTGGTCT TCTTGTGGGCCGACTCGCTCGACTTGT TCCC-3' (150 mer) (SEQ ID NO:88)

Then, PCR reaction was carried out according to the method of Example D3 (1) a). The template DNA used was 1 μg of plasmid p12-BI and the primers used were RCE I-01 and RCE I-P335-Xho-C, each 1 μM. The PCR reaction was carried out under the same conditions as in Example D3 (1) a) to amplify DNA of about 300 bp. The DNA of about 300 bp was subcloned into pT7 Bleu T-vector and the resulting plasmid was designated as p123-6.

c) Preparation of Plasmid p34-6:

First, two synthetic oligonucleotides having the following sequences were prepared.

RCE I-03: 5'-GGAAACAAGTCGAGCGAGTCGGCCC ACAAGAAGACCACGACCGCTGCCCACAAGAA GACCACGACCGCCGCTCACAAGAAGAC- TACGACCGCTCCCGCCAAGAAGACCACGACCGT CGCCAAGGCTTCGACTCCGTCCAACTCGAGC AGCTCGTCCTC-3' (158 mer) (SEQ ID NO:89)

RCE I-04: 5'-GTCCTTGTTGCAGGACTTGACAGGC GAGCTGACGTTAGCCTTGCCGGGCCACGAGCAC GAAGCCTTGCAGCAGTCCCAGTAGCGGGTAG TGACGCCGTTGCCGCTAGCGCCACCGCTGAC AGCGCTGTACTTTCCCGAGGACGAGCTGCTC GAGTTGGAC-3' (160 mer) (SEQ ID NO:90)

Then, these oligonucleotides were used to carry out PCR reaction. According to the method of Example D3 (1) a), dNTP and buffer were added to RCE I-03 and RCE I-04, each 1 μM, and the reaction was carried out under the same conditions. The amplified DNA of about 300 bp was subcloned into pT7 Bleu T-vector and the resulting plasmid was designated as p34-6.

d) Preparation of plasmid p3456-18:

First, two synthetic oligonucleotides having the following sequences were prepared.

RCE I-P34-6-Nco-C: 5'-AGCCCATGGCTGGTTGTCG TTGCACATGTAGGAGTTGCCGCCGTTGCAGCCG GACTGGGCGTTGGAGTCGCTAAGAGCGGTGACG CCGTCCTTGTTGCAGGACTTGACAGGCGA GCTGAC-3' (120 mer) (SEQ ID NO:91)

RCE I-P34-6-Sac-C: 5'-GGTGAGCTCGAAGCAGGAG CAGCACCAGCGGCTCTCGCCACCGCCGCTAATG GCAGCGGCAGCGAAACCGTAAGCAAGGT- TGTCGTTGA CAGCCCATGGCTGGTTGTCGTTG CACATG-3' (118 mer) (SEQ ID NO:92)

Then, PCR reaction was carried out according to the method of Example D3 (1) a). The template DNA used was 1 μg of plasmid p34-6 and the primers used were RCE I-03 and RCE I-P34-6-Nco-C, each 1 μM. The PCR reaction was carried out under the same conditions as in Example D3 (1) a) to amplify DNA of about 400 bp. The DNA of about 400 bp was recovered by using the aforementioned Sephaglas BandPrep kit and the PCR reaction was further carried out using this DNA fragment as a template.

Thus, using about 20 ng of the previously recovered DNA fragment of about 400 bp as a template DNA and 1 μM each of RCE I-03 and RCE I-P34-6-Sac-C as primers, the PCR reaction was carried out under the same conditions as in Example D3 (1) a) to amplify DNA of about 500 bp. The amplified DNA of about 500 bp was subcloned into pT7 Bleu T-vector and the resulting plasmid was designated as p3456-18.

e) Preparation of Plasmid p78-2:

First, two synthetic oligonucleotides having the following sequences were prepared.

RCE I-07: 5'-GTGCCCACTTCGATCTCCAGATGCCCG GCG GCG GCGTCGGCA TCTTCAACGGAT-

GCTCGTCCCAGTGGGGCGCTCCCAACGACGGC
TGGGGCTCGCGCTACGGCGGCATCAGCTCC
GCCAGCGACTGCTCGTCCCTCCCCAGCGCCCTCC
AGGC-3' (154 mer) (SEQ ID NO:93)

RCE I-08: 5'-GGGGGGATCCTGCGTTTACTTGCG
CGAGCATCCGGTCTTAGCGGTGATCTCCTTGG
GGCAGGTGACCTCCTTGTAGGTCATGGACGGG
TTGTCGGCGTTCTTGAACCAGTTGAAGC
GCCACTTGCAGCCGGCCTGGAGGGCGCTGGG
GAGGGAC-3' (154 mer) (SEQ ID NO:94)

Then, these oligonucleotides were used to carry out PCR reaction. According to the method of Example D3 (1) a), dNTP and buffer were added to RCE I-07 and RCE I-08, each 1 µM, and the reaction was carried out under the same conditions. The amplified DNA of about 300 bp was subcloned into pT7 Bleu T-vector and the resulting plasmid was designated as p78-2.

f) Preparation of Plasmid p678-8:

First, two synthetic oligonucleotides having the following sequences were prepared.

RCE I-P78-2-SacN: 5'-GGGGAGCTCACCTTCACC
TCCACCAGCGTTGCTGGCAAGAAGATGGTCGTC
CAGGTCACCAACACTGGCGGTGACCTTG-
GCAGCTCGACCG GTGCCCACTTCGATCTC
CAGATGCCC-3' (117 mer) (SEQ ID NO:95)

RCE I-H-C: 5'-GGGGGGATCCTGCGTTTACT
TGCGCGAGCATC-3' (32 mer) (SEQ ID NO:96)

Then, PCR reaction was carried out according to the method of Example D3 (1) a). The template DNA used was 1 µg of plasmid p78-2 and the primers used were RCE I-P78-2-SacN and RCE I-H-C, each 1 µM. The PCR reaction was carried out under the same conditions as in Example D3 (1) a) to amplify DNA of about 400 bp. The DNA of about 400 bp was subcloned into pT7 Bleu T-vector and the resulting plasmid was designated as p678-8.

g) Preparation of Plasmid p18-:

First, plasmid p3456-18 was digested with XhoI and SacI to recover DNA fragment of about 300 bp. Then, plasmid p678-8 was digested with SacI and KpnI to recover DNA fragment of about 400 bp. These DNA fragments were ligated using DNA ligation kit and the ligation mixture was subjected to agarose gel electrophoresis to recover DNA fragment of about 700 bp. This DNA fragment was ligated to plasmid p123-6, which had been digested with XhoI and KpnI to yield plasmid p18-1.

(2) Analysis of Nucleotide Sequence of Codon Optimized Endoglucanase RCE I Gene

The nucleotide sequence was analyzed in the same manner as in Example B3 (3). Thus, using plasmid p18-1 obtained in Example D3 (1) g) as a template DNA and newly prepared FTFC labeled sequencing primers RCE-H01 to H08 having the following sequences as primers, the reaction was carried out for analysis.

As a result, the whole nucleotide sequence of the codon optimized endoglucanase RCE I gene on the plasmid p18-1 could be analyzed. The codon optimized endoglucanase RCE I gene had the nucleotide sequence of SEQ ID NO:13 and the amino acid sequence deduced from this sequence completely coincided with the amino acid sequence of endoglucanase RCE I of SEQ ID NO:1.

RCE-H01: 5'-TCAGCGGTGGCGCTAGCGGCAAC-3' (23 mer) (SEQ ID NO:97)
RCE-H02: 5'-CTAATGGCAGCGGCAGCGAAACC-3' (23 mer) (SEQ ID NO:98)
RCE-H03: 5'-CCGGTGCCCACTTCGATCTCCAG-3' (23 mer) (SEQ ID NO:99)
RCE-H04: 5'-TCTTTCCGCCGCACTGTCCGTAG-3' (23 mer) (SEQ ID NO:100)
RCE-H05: 5'-ACGACAACCAGCCATGGGCTGTC-3' (23 mer) (SEQ ID NO:101)
RCE-H06: 5'-TCTCGAATGACTACTACAGCCAG-3' (23 mer) (SEQ ID NO:102)
RCE-H07: 5'-CCCACTGGGACGAGCATCCGTTG-3' (23 mer) (SEQ ID NO:103)
RCE-H08: 5'-CGAGCTGCTCGAGTTGGACGGAG-3' (23 mer) (SEQ ID NO:104)

(3) Preparation of Plasmid pJI4D01

Plasmid pJD01 obtained in Example D1 (1) was digested with BamHI and then dephosphorylated with alkaline phosphatase. Then, the plasmid p18-1 obtained in Example D3 (1) g) was digested with BamHI to recover DNA fragment of about 1 kbp. And, these DNAs were operably ligated and the resulting plasmid was designated as pJI4D01.

(4) Transformation of *Humicola insolens* with Plasmid pJI4D01

According to the method described in WO98/03667, *Humicola insolens* MN200-1 was transformed with plasmid pJI4D01 and 50 strains showing hygromycin resistance were selected.

Example D4

Expression of Codon Optimized Endoglucanase RCE I Gene in *Humicola insolens* (II)

(1) Cultivation of Transformant with Plasmid pJI4D01 and Evaluation by SDS-PAGE

According to the method described in WO98/03667, 50 transformants with plasmid pJI4D01 were cultivated in (N) medium at 37° C. for 4 days. The resulting cultivation supernatant was analyzed by SDS-PAGE to detect a protein band of about 40 kD in molecular weight presumed to be endoglucanase RCE I in 5 strains among the transformants with plasmid pJI4D01.

(2) Evaluation by Lyocell Fuzz Removal Activity of Transformants with Plasmid pJI4D01

Among the 5 strains showing the expression of a protein with molecular weight of about 40 kD by SDS-PAGE in (1) above, the cultivation supernatants of two strains (1-18 and 2-15 strains) which showed particularly significant expression were used to measure lyocell fuzz removal activity. The cultivation supernatant of the untransformed recipient strain was used as a control. According to the method of Example A4, the amount of the cultivation supernatant required to completely remove fuzz was measured by lyocell fuzz removal treatment with various cultivation supernatants under the reaction condition of pH 6, 55° C. The results are shown in Table 3 below.

TABLE 3

| | Amount of the cultivation supernatant required for lyocell fuzz removal (ml) |
|---|---|
| *Humicola insolens* MN200-1 (recipient) | Only 60% of fuzz were removed even by addition of 8.0 ml. |
| *Humicola insolens* pJI4D01 (1-18) | 2.0 |
| *Humicola insolens* pJI4D01 (2-15) | 0.1 |

Example D5

Expression of Codon Optimized Endoglucanase RCE I Gene in *Humicola insolens* (III)

(1) Evaluation by FPLC of Transformant with Plasmid pJI4D01

Each of the cultivation supernatants of the transformant (2-15 strain) with plasmid pJI4D01 obtained in Example D4 and the recipient strain was subjected to column chromatography using FPLC system (Pharmacia Biotech) (column: RESOURCE™ RPC 3 ml, 5 to 60% acetonitrile gradient containing 0.1% TFA). As a result, a novel peak, which was not seen in the recipient strain, was detected in the cultivation supernatant obtained from the transformant (2-15) with plasmid pJI4D01.

(2) Identification of N-terminal Amino Acid Residues of Recombinant Endoglucanase RCE I From Examples D4 and D5 above, it was believed that a recombinant endoglucanase RCE I was expressed in a large amount as the result of optimization of codons in endoglucanase RCE I gene. Accordingly, N-terminal amino acid sequence of this protein was determined in order to confirm that the abundantly expressed protein was derived from the codon-optimized endoglucanase RCE I gene.

First, according to Example D5 (1), the transformant (2-15) with plasmid pJI4D01 was subjected to FPLC system to isolate the resulting novel peak. Then, this peak was centrifuged and subjected to SDS-PAGE (using 8% gel). The protein was electrically transferred to PVDF membrane (Millipore) using MULTIFOR II electrophorelic apparatus (Pharmacia), stained with Coomassie Brilliant Blue R-250, decolored, washed with water and air-dried. Thereafter, the target band (40 kD) was digested out and subjected to Protein Sequencer Model 492 (Perkin Elmer) to determine 16 residues of N-terminal amino acid sequence. The resulting sequence is shown below.

N-terminal amino acid sequence:
Ala-Glu-(Cys)-Ser-Lys-Leu-Tyr-Gly-Gln-(Cys)-Gly-Gly-Lys-Asn-Trp-Asn (16 residues) (SEQ ID NO:105)

This N-terminal amino acid sequence coincided with the amino acid sequence of endoglucanase RCE I protein deduced from the nucleotide sequence of plasmid pJI4D01.

Therefore, it was confirmed that the recombinant endoglucanase RCE I was expressed in a large amount in *Humicola insolens* as the result of the optimization of codons in the endoglucanase RCE I gene.

Example D6

Expression of Codon Optimized Endoglucanase RCE I Gene in *Aspergillus niger* (I)

(1) Acquisition of niaD Mutant from *Aspergillus niger* Strain FERM P-5886

Spores of *Aspergillus niger* strain FERM P-5886 were smeared on the minimal agar medium (0.2% sodium glutamate, 0.1% dipotassium hydrogenphosphate, 0.05% magnesium sulfate, 0.05% potassium chloride, 0.001% iron sulfate, 3% sucrose, 1.5% agar, pH 5.5) containing 6% chlorate and incubated at 30° C. After cultivation for about 5 days, those forming colonies were taken as chlorate resistant strains. These resistant strains were inoculated in the minimal medium containing glutamate, nitrate or nitrite, respectively, as a single nitrogen source to investigate nitrogen requirements. As a result, there was present chlorate resistant strains which could grow in the minimal medium containing sodium glutamate or nitrite as a single nitrogen source but could not grow in nitrate. These strains were taken as candidates for niaD mutant.

With 3 strains among the niaD mutant candidates, the nitrate reductase (nitrate reducing enzyme, which is a niaD gene product) activity in the cells was measured. These three strains were shaker cultivated in a liquid medium (0.25% sodium glutamate, 0.1% dipotassium hydrogenphosphate, 0.05% magnesium sulfate, 0.05% potassium chloride, 0.001% iron sulfate, 3% sucrose) at 30° C. for 60 hours. The resulting wet cells (0.2 g) were suspended in 2 ml of 50 mM sodium phosphate buffer (pH 7.5) and crushed by an ultrasonic homogenizer. After insoluble fractions were removed by centrifugation, the cultivation supernatant was taken as a sample. To 50 μl of the sample solution, 1000 μl of distilled water, 750 μl of 0.2 M sodium phosphate solution (pH 7.5), 100 μl of 0.04 mg/ml FAD, 100 μl of 2 mg/ml NADPH, and 1000 μl of 22.5 mg/ml sodium nitrate were added, followed by reacting at 37° C. After the reaction, 500 μl of 1% sulfanilamide (dissolved by 3N hydrochloric acid) and 500 μl of 0.02% N-1-naphthyl-ethylenediamine were added to the sample for color formation and A540 was measured to detect the nitrate reductase activity. However, no nitrate reductase activity was detected in there three strains. Therefore, it was concluded that these three strains were niaD mutant strains and one of them was designated as NIA5292 strain, which was subjected to subsequent experiments.

(2) Acquisition of niaD Gene from *Aspergillus niger* Strain FERM P-5886 a) Preparation of Probe:

*Aspergillus niger* strain NRRL4337 was cultivated in YPD liquid medium (1% yeast extract, 2% polypeptone, 2% glucose). DNA was amplified by PCR method using the total DNA extracted from the resulting cells by the known method (Japanese Patent Application Laying Open No. 8-53522) as a template and synthetic DNA primers of SEQ ID NOs:106 and 107 prepared based on the nucleotide sequence of *Aspergillus niger* niaD gene described in Unkles, S. E., et al., Gene, 111, 149–155 (1992) as primers. The reaction solution contained 0.5 μg chromosome DNA, 100 pmol each primer and 2.5 U Taq DNA polymerase (Nippon Gene) per 100 μl. The reaction was carried out 25 cycles under the temperature conditions of 94° C. for 1 minute, 50° C. for 2 minutes and 72° C. for 2 minutes to specifically amplify DNA fragment of about 800 bp. The nucleotide sequence of this DNA fragment was determined and completely (100%) coincided with the nucleotide sequence of *Aspergillus niger* niaD gene already reported. Thus, it was clarified that this DNA fragment was derived from niaD gene. Accordingly, this DNA fragment of about 800 bp was taken as a probe for use.

NIA-CN: 5'- GACTGACCGGTGTTCATCC-3' (19 mer) (SEQ ID NO:106)
NIA-CC: 5'- CTCGGTrGTCATAGATGTGG-3' (20 mer) (SEQ ID NO:107)

b) Southern analysis of chromosome DNA of *Aspergillus niger*:

*Aspergillus niger* strain FERM P-5886 was cultured in YPD liquid medium (1% yeast extract, 2% polypeptone, 2% glucose). Total DNA extracted from the resulting cells by the known method (Japanese Patent Application Laying Open No. 8-53522) was completely digested with restriction enzymes (Hindm, EcoRI, BamHI, SacI, SalI, XbaI), fractionated by agarose gel electrophoresis, and blotted on nylon membrane (Hybond-N+, Amersham) according to the method described in Molecular Cloning (Cold Spring Harbour, 1982). Southern hybridization was effected to the nylon membrane using the aforementioned 800 bp DNA fragment as a probe. For labeling probes and detecting signals, Ecl DirectI DNA Labeling-Detection System (Amersham) was used under the conditions following the manual attached. As a result, signals were detected at positions of about 6.5 kbp upon digestion with SalI.

c) Isolation of niaD Gene:

Total DNA of *Aspergillus niger* strain FERM P-5886 was partially cleaved with restriction enzyme MboI, and fractionated by agarose gel electrophoresis. DNA fragments near 9–23 kbp were extracted and recovered by conventional methods. The recovered DNA fragment was ligated into BamHI site of λ DASHII and packaged by GIGAPACK II Gold (Stratagene). *E. coli* was infected with the phage to prepare a library.

Plaque hybridization was carried out using the aforementioned 800 bp DNA fragment as a probe and Ecl DirectI DNA Labeling-Detection System (Amersham), to obtain positive clones. The resulting positive clones were subjected to secondary screening to purify the positive clones.

Phage DNA was prepared from the positive clones to confirm the insertion of about 6.5 kbp SalI fragment. This DNA was subjected to Southern analysis to find a smaller DNA fragment of about 4.8 kbp SacI fragment. The restriction enzyme map of this fragment was made. Further, this Sac fragment was subcloned into plasmid pUC118. The resulting plasmid was designated as pniaD-Sac. This SacI fragment was further digested with suitable restriction enzyme(s) and then subcloned into pUC118. This was used as a template to determine the nucleotide sequence and the position of niaD gene in the isolated DNA fragment was identified.

(3) Transformation of *Aspergillus niger* Strain NIA5292

*Aspergillus niger* strain NIA5292 was shaker cultivated in a liquid medium (2% soluble starch, 1% polypeptone, 0.2% yeast extract, 0.5% sodium dihydrogenphosphate, 0.05% magnesium sulfate) at 28° C. for 24 hours. Cells were collected by a glass filter, suspended into an enzyme solution (1 mg/ml β-glucuronidase (Sigma), 5 mg/ml Novozyme 234 (Novo Nordisk), 10 mM sodium phosphate (pH 5.8), 0.8 M potassium chloride), and gently heated at 30° C. for 1.5 hours. Protoplasts were filtered through a glass filter and the passed fraction was centrifuged to collect cells, which were washed twice with STC buffer (10 mM Tris (pH 7.5), 10 mM potassium chloride, 1.2 M sorbitol) and suspended into STC buffer. Subsequently, the protoplast and plasmid DNA were mixed and allowed to stand on ice for 20 minutes. Further, PEG solution (10 mM Tris (pH 7.5), 10 mM potassium chloride, 60% polyethylene glycol 4000) was added and allowed for stand on ice for another 20 minutes to introduce the DNA into the protoplast. The protoplast was washed several times with STC buffer, suspended in Czapek medium (0.2% sodium nitrate, 0.1% dipotassium hydrogenphosphate, 0.05% magnesium sulfate, 0.05% potassium chloride, 0.001% ferric sulfate, 3% sucrose) containing 1.2 M sorbitol and 0.8% agar, layered on Czapek agar medium containing 1.2 M sorbitol and 1.5% agar, and cultivated at 30° C. After cultivation for about 5 days, those forming colonies were selected as transformants.

Example D7

Expression of Codon Optimized Endoglucanase RCE I Gene in *Aspergillus niger* (II)

(1) Preparation of Plasmid pSAEX11

An expression vector having an amylase promoter operable in Aspergillus niger was constructed in the following manner.

a) Preparation of plasmid pAMYI:

First, plasmid pAMY obtained according to WO97/00944 was digested with restriction enzymes EcoRI and SalI and the resulting DNA fragment of about 0.75 kb was ligated to pUC119 also digested with EcoRI and SalI. The resulting plasmid was designated as pAMYI.

b) Site-directed Mutagenesis of Plasmid pAMYI:

BamHI site was introduced into a site immediately upstream from the initiation codon of amylase gene by site-directed mutagenesis. The method of site-directed mutagenesis followed Example B7 (1).

First, a synthetic oligonucleotide pAMBM as set forth below as a primer for mutagenesis was newly prepared and phosphorylated at 5' end. Then, the plasmid pAMYI was brought into single-strand in *E. coli* strain CJ236 and reacted with the phosphorylated primer to yield a mutant DNA. This mutagenized plasmid was designated as pAMY-Bam.
pAMBM: 5'-CCCACAGAAGGGATCCATGATGGTCGC-3' (27 mer) (SEQ ID NO:108)

c) Preparation of Plasmid pSAEX11:

First, plasmid pAMY-Bam was digested with restriction enzymes EcoRI and BamHI and the resulting DNA fragment of about 0.6 kb was recovered. Then, plasmid pDH25 obtained according to Cullen et al. report (Cullen, D., Gene, 57, 21–26, 1987) was digested with EcoRI and BamHI and the resulting DNA fragment of about 4.7 kb was recovered. The both were ligated and the resulting plasmid was designated as pSAEX11.

(2) Preparation of Plasmids pANR22 and pANH42

In order to express the endoglucanase RCE I gene derived from *Rhizopus* and the codon optimized endoglucanase RCE I gene prepared by full synthesis in *Aspergillus niger*, expression vectors pANR22 and pANH42 were constructed.

a) Preparation of Plasmids pANR21 and pANH41:

First, plasmid pHRCEI-Bgl-11 was digested with restriction enzyme BglII and the resulting DNA fragment of about 1 kb was recovered as the endoglucanase RCE I gene fragment derived from *Rhizopus*. Also, plasmid pJI4D01 was digested with BamHI and the resulting DNA fragment of about 1 kb was recovered as the codon optimized endoglucanase RCE I gene fragment.

Then, plasmid pSAEX11 was digested with BamHI and ligated to each of the BglII fragment of the endoglucanase RCE I gene and the BamHI fragment of the codon optimized endoglucanase RCE I gene. The resulting plasmids were designated as pANR21 and pANH41, respectively.

b) Preparation of Plasmids pANR22 and pANH42:

First, plasmids pANR21 and pANH41 were digested with restriction enzyme XbaI. Then, plasmid pniaD-Sac described in Example D6 was digested with restriction enzyme XbaI to yield a fragment of about 4.8 Kbp. This fragment contained from the restriction enzyme XbaI recognition site present immediately after the restriction enzyme SacI recognition site in the upstream region of niaD gene to the restriction enzyme XbaI recognition site derived from pUC118 present immediately after the restriction enzyme SacI recognition site in the downstream region of niaD gene. This 4.8 kbp fragment was inserted into XbaI site of plasmids pANR21 and pANH41. The resulting plasmids were designated as pANR22 and pANH42.

Example D8

Expression of Codon Optimized Endoglucanase RCE I Gene in *Aspergillus niger* (III)

(1) Transformation of *Aspergillus niger* Strain NIA5292 with Plasmids pANR22 and pANH42

According to the method described in Example D6, *Aspergillus niger* strain NIA5292 was transformed with plasmids pANR22 and pANH42, as well as the vector only as a control. About 50 strains each of the transformants on Czapek agar medium were cultivated in SMPN liquid medium (3% soluble starch, 0.7% malt extract, 1% polypeptone, 0.3% NaCl) at 28° C. for 3 days. After the cultivation supernatant was dialyzed, lyocell fuzz was removed under the reaction condition of pH 6, 55° C. according to Example A4 to investigate the degree of fuzz removal. The results are shown in Table 4. The cultivation broth of the transformant with plasmid pANH42 showed activity in the removal of fuzz from lyocell, while the cultivation broth of strains transformed with the vector only or with plasmid pANR22 showed no lyocell fuzz removal activity.

TABLE 4

| | Degree of lyocell fuzz removal |
|---|---|
| Aspergillus niger (vector only) | No fuzz was removed. |
| Aspergillus niger pANR22 | No fuzz was removed. |
| Aspergillus niger pANH42 | 80% of fuzz were removed. |

Example D9

Expression of Codon Optimized Endoglucanase RCE I Gene from which a Part of the Linker Region was Deleted in *Humicola insolens*

(1) A part of the Linker Region in RCE I Gene in the Plasmid pJI4D01 (from the 331st Base G to the 405th Base C in SEQ ID NO:13) was Deleted Using PCR and this Plasmid was Designated as pJI4D10.
(2) Cultivation of Transformant with Plasmid pJI4D01 and Evaluation by SDS-PAGE According to the method described in WO98/03667, 30 transformants with plasmid pJI4D10 were cultivated in (N) medium at 37° C. for 4 days. The resulting cultivation supernatant was analyzed by SDS-PAGE to detect a protein band of about 30–35 kD in molecular weight presumed to be a deleted RCE I in 5 strains among the transformants with plasmid pJI4D10.
(3) Evaluation of Lyocell Fuzz Removal Activity of Transformants with Plasmid pJI4D10

Among the 5 strains showing the expression of a protein with molecular weight of about 30–35 kD by SDS-PAGE in (2) above, the cultivation supernatant of one strain (3-13 strain) which showed particularly significant expression was used to measure lyocell fuzz removal activity. The cultivation supernatant of 2-15 strain from which a portion of linker region of RCE I was not deleted was used as a control. According to the method of Example A4, the degree of fuzz removal was investigated by lyocell fuzz removal treatment with various cultivation supernatants (each 0.1 ml) under the reaction condition of pH 6, 55° C. The results are shown in Table 5 below.

TABLE 5

| | Degree of lyocell fuzz removal |
|---|---|
| Humicola insolens pJI4D01 (2-15) | Fuzz was removed completely. |
| Humicola insolens pJI4D10 (3-13) | No fuzz was removed. |

Example E1:

Search for Homologs of RCE I Gene in *Mucor circinelloides*

To search for homologs of endoglucanase RCE I gene in genomic DNA of *Mucor circinelloides*, analysis was carried out by Southern hybridization.

First, about 10 μg of genomic DNA of *Mucor circinelloides* obtained according to Example B2 was digested with plural restriction enzymes (EcoRI, BamHI, HindIII, SacI, XbaI, SalI, etc.) and subjected to 0.8% agarose gel electrophoresis. These materials were transferred to a membrane according to Example B5 (3) and hybridized using RCE I gene as a probe under the same conditions as in the aforementioned examples. As a result, it was found that at least one homologous gene was present on the genomic DNA of *Mucor circinelloides*. This gene was detected as a single band, particularly in the hybridization when the genomic DNA was digested with EcoRI. Accordingly, the gene detected as a band of about 4.5 kbp was designated as MCE I and subjected to subsequent cloning.

Example E2

Cloning of Endoglucanase MCE I Gene
(1) Preparation of Genomic DNA Library (for Cloning MCE I Gene)

The genome DNA of *Mucor circinelloides* was digested with EcoRI and subjected to 0.8% agarose gel electrophoresis using Seakem LE agarose to extract and purify DNA fragments of about 3 to 6.5 kbp in size according to conventional methods. These DNA fragments were ligated into a phage vector, Lambda gt10 vector (Stratagene) and packaged in the same manner as in Example B4. *E. coli* strain NM514 was infected with the resulting phage. The phage library ($1 \times 10^4$) obtained by this method was used to clone MCE I gene.
(2) Cloning of MCE I Gene from Genomic DNA Screening by plaque hybridization was carried out using the library obtained in Example E2 (1) and RCE I gene probe. Hybridization was carried out under the same conditions as in Example B5 to yield 6 phage clones.

*E. coli* strain NM514 was infected with the resulting phage and DNAs were prepared according to the method of Example B5 (2), digested with EcoRI and subjected to 0.8% agarose gel electrophoresis. The DNAs were transferred to a nylon membrane according to the method of Example B5 (3) and hybridized. As a result, a common band having the same size of about 4.5 kbp as the genomic DNA was detected in the 6 phage DNAs. This band was recovered and subcloned into the EcoR site of plasmid pUC119. The resulting plasmid was designated as pMCEI-Eco. The nucleotide sequence of this about 4.5 kbp was determined in the same manner as in Example B3 (3). The elucidated nucleotide sequence was translated into an amino acid sequence. A reading frame coincided with the N-terminal amino acid sequence of endoglucanase MCE I as shown in Example B1. However, it was presumed that this sequence contained introns and, therefore, cDNA of MCE I gene was isolated by RT-PCR.
(3) Isolation of cDNA of MCE I Gene by RT-PCR and Determination of Nucleotide Sequence

*Mucor circinelloides* was cultivated in 30 ml of liquid medium (3.0% corn steep liquor, 0.5% yeast extract (Difco), 2.4% potato dextrose broth (Difco), 2% sucrose) at 30 C for 18 hours and the cells were collected by a glass filter. The resulting cells were lyophilized and finely crushed by a spatula. Total RNA was isolated using Isogen (Wako Pure Chemical Industry). First, 5 ml of Isogen was added to the cell powder, vortexed for 30 seconds and incubated at 50° C. for 10 minutes, followed by allowing to stand at room temperature for 5 minutes. Then, 0.8 ml of chloroform was added and vigorously shaken. After centrifugation, the aqueous layer was transferred to another vessel, to which 2 ml of 4 M LiCl was added and mixed, followed by allowing to stand at −70° C. for 15 minutes. Thereafter, the material was centrifuged and the supernatant was removed. The precipitate was dissolved in 1.6 nl of water and 1.6 ml of isopropanol was added and mixed, followed by allowing to stand at 4° C. for 30 minutes. After centrifugation, the supernatant was removed and the precipitate was washed with 75% ethanol. The precipitate was dissolved in 1.6 ml of water. This solution was precipitated with ethanol and the precipitate was washed with 75% ethanol, dried and dissolved in 0.4 ml of water to yield total RNA.

Then, mRNA was prepared using mRNA Isolation Kit (Stratagene). First, 10 ml of Elution Buffer was added to 0.2 ml of total RNA prepared above, and 5 ml of oligo dT solution was further added. After removing the supernatant, the oligo dT was washed three times with High Salt Buffer and twice with Low Salt Buffer and then eluted with Elution Buffer heated to 68° C. This solution was precipitated with ethanol and the precipitate was washed with 75% ethanol, dried and dissolved in 15 µl of water to yield mRNA fraction.

Then, cDNA of MCE I gene was prepared from the mRNA by RT-PCR using Takara RNA PCR Kit (AMV) Ver. 2.1. Thus, oligonucleotide primers having the following sequences were prepared as primers for N- and C-terminals deduced from the genomic MCE I gene sequence determined above and only cDNA of MCE I gene was amplified by PCR method using 1 µl of mRNA prepared above as a template.

MCEI-CN:
   5'-GCGAATTCATGAAGTTCACCGTTGCTATT-3 (29 mer) (SEQ ID NO:109)

MCEI-CC:
   5'-GCGAATTCTTACTTTCTTTCGCAACCTG-3 (28 mer) (SEQ ID NO:110)

The RT-PCR reaction was effected under the following conditions. First, the C-terminal primer was added to the reaction mixture and reacted with reverse transcriptase. Then, Taq polymerase (recombinant Taq, Takara Shuzo) and the N-terminal primer were added and the reaction conditions of 94° C. for 1 minute, 50° C. for 2 minutes and 72° C. for 2 minutes were repeated 30 times to amplify. As a result of agarose gel electrophoresis, the amplified fragments were two fragments of about 1.1 kbp and 1.0 kbp. These fragments were subcloned into EcoRI site of pUC118 and the nucleotide sequences of the respective fragments were determined according to the method of Example B3 (3). This nucleotide sequence was compared with the genomic nucleotide sequence to determine introns. As a result of this analysis, it was found that in *Mucor circinelloides,* two endoglucanases were expressed wherein the gene sequences were identical with each other in a portion of N- and C-terminals. Accordingly, the endoglucanases encoded by the shorter (about 1.0 kbp) and longer (about 1.1 kbp) nucleotide sequences were designated as MCE I and MCE II, respectively.

Example E3

Expression of Endoglucanase MCE I Gene (1) Site-directed Mutagenesis of MCE I Gene The cDNA of MCE I gene prepared by RT-PCR had a mutation. This mutation was restored by site-directed mutagenesis. This MCE I plasmid subcloned into EcoRI site of pUC118 was designated as pMCEI-EcoRI. Further, MCE I gene had one Asn-linked glycosylation site, Asn-X-Ser/Thr sequence, and it was believed that an oligosaccharide chain bound to the asparagine residue at 50th position in the amino acid sequence of SEQ ID NO:7. Since it was believed that lyocell fuzz removal activity would be inhibited by excessive glycosylation in the Asn-linked glycosylation sites like RCE I, a mutant endoglucanase MCE I gene in which the amino acid at the Asn-linked glycosylation site was replaced was created by site-directed mutagenesis.

The site-directed mutagenesis was carried out according to the method of Example B7 (1). Thus, a synthetic oligonucleotide pIMI-S52G as set forth below was prepared as a mutagenesis primer and phosphorylated at 5' end thereof. Then, *E. coli* strain CJ236 was transformed with plasmid pMCEI-EcoRI and a helper phage was used to obtain ssDNA. This ssDNA and primer were annealed and double-stranded through polymerase reaction using the aforementioned kit and introduced into *E. coli* strain JM109 to yield a mutant DNA, which was designated as pMCEI-G.

PIMI-S52G: 5'-CTTGGTGCTGCCAGCGTTACCAG-3' (23 mer) (SEQ ID NO:111)

(2) Expression of Mutant MCE I Gene in Yeast

The mutant RCE I gene was expressed in yeast according to the method of Example B7 (2). Thus, the plasmid pMCEI-G obtained in Example E3 (1) was digested with EcoRI and a mutant MCE I gene was recovered. This gene was operably linked to the EcoRI site downstream from glyceraldehyde-3-phosphate dehydrogenase (GAP) promoter of plasmid vector pY2831 to yield a plasmid pYM-CEI. This plasmid was used to transform yeast (*Saccharomyces cerevisiae*) strain MS-161 (MATa, trpl, ura3) according to WO97/34004 specification. Thus, a transformant was obtained in which the endoglucanase MCE I could be expressed.

Example E4

Evaluation of Mutant Endoglucanase MCE I Expressed in Yeast (1) Cultivation of Yeast Expressing Mutant MCE I The yeast transformed with the plasmid pYMCEI obtained in Example E3 was cultivated under the same conditions as in Example B8 (1) to yield a crude enzyme solution as a cultivation supernatant.

(2) Measurement of Molecular Weight by SDS-PAGE

The crude enzyme solution obtained in Example E4 (1) was subjected to SDS-PAGE to detect a smear band having a molecular weight of about 45 kD.

(3) Evaluation of Yeast in which Mutant MCE I was Expressed (CMCase Activity)

The crude enzyme solution obtained in Example E4 (1) was used to measure CMCase activity. A cultivation broth of a strain transformed only with the vector DNA into which the mutant MCE I gene was not introduced was similarly treated and used as a control.

|  | CMCase (U/ml) |
| --- | --- |
| Mutant MCE I gene recombinant | 0.337 |
| Control | 0.000 |

(4) Purification of Mutant MCE I Expressed in Yeast

An ammonium sulfate solution at a final concentration of 1.5 M was prepared from 500 ml of the crude enzyme solution obtained in Example E4 (1) and applied at a flow rate of 3.0 ml/min to Macro-Prep Methyl HIC Support hydrophobic chromatography (25 ml in gel volume, BioRad Laboratories) which had been equilibrated with 1.5 M ammonium sulfate solution. It was then fractionated by eluting at a flow rate of 5.0 ml/min in a stepwise elution method in which the concentration of ammonium sulfate in deionized water was decreased by 0.3 M each from 1.5 M. Among the fractions, the fraction obtained at an ammonium sulfate concentration of 0.6 M was found to have a strong lyocell fuzz removal activity. Therefore, 50 ml of this fraction was isolated. By repeating twice the fractionation by Macro-Prep Methyl HIC Support hydrophobic chromatography, 1000 ml of the cultivation supernatant were treated to provide 100 ml of active fractions.

An ammonium sulfate solution at a final concentration of 1.5 M was prepared from 100 ml of the active fractions and applied to Econo-Pac Methyl HIC Cartridge hydrophobic chromatography (5 ml in gel volume, BioRad Laboratories) which had been equilibrated with 1.5 M ammonium sulfate solution. Then, 1.5 M ammonium sulfate solution was applied. Deionized water was then applied and 1 ml each and the fractions, which were found to have a strong lyocell fuzz removal activity were pooled, fractionated the eluted fractions. This fraction showed an almost single smear band in SDS-PAGE and had a molecular weight (MW) of about 45 kD. The SDS-PAGE used NPU-12.5L PAGEL (ATTO Japan) and migration and dyeing were carried out according to the specification attached to the gel. Molecular weight standards used were SDS-PAGE molecular weight standard Low range (BioRad Laboratories).

(5) Evaluation of Lyocell Fuzz Removal by Purified Mutant MCE I (Specific Activity in the Removal of Fuzz from Lyocell)

The purified enzyme solution of mutant MCE I obtained in Example E4 (4) was used to evaluate lyocell fuzz removal activity under the conditions as set forth below in the same manner as in Example A4. Thus, a knitted fabric of lyocell (Toyoshima Japan, 9 cm×10 cm, about 2 g in weight) fuzzed by the method of Example A4 was subjected to lyocell fuzz removal treatment under the conditions as set forth below, whereby the protein concentration of mutant MCE I required to completely remove fuzz formed was calculated.

The protein concentrations of mutant MCE I were calculated from the peak area at UV 280 nm of various endoglucanases eluted with a linear gradient from 0% to 80% of acetonitrile concentration in 0.05% TFA (trifluoroacetic acid) at a flow rate of 1.0 ml/min in HPLC analysis using TSK gel TMS-250 column (4.6 mm×7.5 cm, Toso Japan). The standard used was a purified NCE4 which was analyzed in HPLC under the same conditions, the protein concentration of which had been preliminarily measured by Protein Assay Kit (BioRad Laboratories). The standard used to measure the protein concentration in the protein assay kit was Albumin Standard (Bovine serum albumin, fraction V, PIERCE).

Test machine: Launder Meter L-12 (Daiei Kagaku Seiki MFG., Japan)
Temperature: 50° C.
Time: 60 minutes
Reaction volume: 40 ml
Reaction pH: pH 5 (10 mM acetate buffer)
  pH 6 (10 mM acetate buffer)

The treating liquid contained 4 rubber balls (about 16 g each) together with the endoglucanase solution.

The results are as shown in Table 6 below. The mutant endoglucanase MCE I expressed in yeast had an almost identical lyocell fuzz removal activity per enzyme concentration with the endoglucanase MCE I purified by the method as shown in Example A2.

TABLE 6

| Enzyme | pH 5 | pH 6 |
| --- | --- | --- |
| MCE I | 0.5 mg/l | 0.5 mg/l |

(6) Evaluation of Lyocell Fuzz Removal by Mutant MCE I Expressed in Yeast at Different pHs (pH Profile Lyocell Fuzz Removal Activity of MCE I)

The crude MCE I enzyme solution obtained in Example E4 (1) was used to evaluate lyocell fuzz removal activity at a pH of 4 to 10 under the condition of 50° C. according to the method of Example A5.

The results are shown in FIG. 2. As seen from the figure, the optimum pH for MCE I was 5–6 and 60% or more of the activity at the optimum pH was maintained in the range of pH 5 to 8. It is apparent that, like MCE I purified from *Mucor circinelloides* in Example A2, the mutant MCE I expressed in yeast is significantly highly active in the alkaline conditions as compared with the purified NCE4.

Example F1

Search for Homologs of RCE I Gene in *Phycomyces nitens*

To search for homologs of endoglucanase RCE I gene in genomic DNA of *Phycomyces nitens*, analysis was carried out by Southern hybridization.

First, about 10 μg of genomic DNA of *Phycomyces nitens* obtained according to Example B2 was digested with plural restriction enzymes (EcoRI, BamHI, HindIII, SacI, XbaI, SalI, etc.) and subjected to 0.8% agarose gel electrophoresis. These materials were transferred to a membrane according to Example B5 (3) and hybridized using RCE I gene and codon optimized RCE I gene as probes under the same conditions as in the aforementioned examples. As a result, it was found that at least one gene homologous with the codon optimized RCE I gene was present on the genomic DNA of *Phycomyces nitens*.

This gene was detected as a single band, particularly in the hybridization when the genomic DNA was digested with BamHI. Accordingly, the gene detected as a band of about 15 to 19 kbp was designated as PCE I and subjected to subsequent cloning.

Example F2

Cloning of Endoglucanase PCE I Gene
(1) Preparation of Genomic DNA Library (for Cloning PCE I Gene)

The genome DNA of *Phycomyces nitens* was digested with BamHI and subjected to 0.8% agarose gel electrophoresis using Seakem LE agarose to extract and purify DNA fragments of about 9 to 23 kbp in size according to conventional methods. These DNA fragments were ligated into a phage vector, Lambda DASH II vector (Stratagene) and packaged in the same manner as in Example B4. *E. coli* strain XL1-Blue MRA was infected with the resulting phage. The phage library (1.6×10[4]) obtained by this method was used to clone PCE I gene.
(2) Cloning of PCE I Gene from Genomic DNA Screening by plaque hybridization was carried out using the library obtained in Example F2 (1) and codon optimized RCE I gene probe. Hybridization was carried out under the same conditions as in Example B5 to yield 6 phage clones. *E. coli* strain XL1-Blue MRA was infected with the resulting phage and DNAs were prepared according to the method of Example B5 (2), digested with XbaI and subjected to 0.8% agarose gel electrophoresis. The DNAs were transferred to a nylon membrane according to the method of Example B5 (3) and hybridized. As a result, a common band of about 2.3 kbp was detected in the 6 phage DNAs. This band was recovered and subcloned into the XbaI site of plasmid pUC119. The resulting plasmid was designated as pPCEI-Xba. The nucleotide sequence of this about 2.3 kbp was determined in the same manner as in Example B3 (3). The elucidated nucleotide sequence was translated into an amino acid sequence. A reading frame coincided with the N-terminal amino acid sequence of endoglucanase PCE I as shown in Example B 1. However, it was presumed that this sequence contained introns and, therefore, cDNA of PCE I gene was isolated by RT-PCR.

(3) Isolation of cDNA of PCE I Gene by RT-PCR and Determination of Nucleotide Sequence

*Phycomyces nitens* was cultivated in 30 ml of liquid medium (3.0% corn steep liquor, 0.5% yeast extract (Difco), 2.4% potato dextrose broth (Difco), 2% sucrose) at 30° C. for 48 hours and the cells were collected by a glass filter. The resulting cells were lyophilized and finely crushed by a spatula. Total RNA was isolated using Isogen (Wako Pure Chemical Industry). First, 5 ml of Isogen was added to the cell powder, vortexed for 30 seconds and incubated at 50° C. for 10 minutes, followed by allowing to stand at room temperature for 5 minutes. Then, 0.8 ml of chloroform was added and vigorously shaken. After centrifugation, the aqueous layer was transferred to another vessel, to which 2 ml of 4 M LiCl was added and mixed, followed by allowing to stand at −70° C. for 15 minutes. Thereafter, the material was centrifuged and the supernatant was removed. The precipitate was dissolved in 1.6 ml of water and 1.6 ml of isopropanol was added and mixed, followed by allowing to stand at 4° C. for 30 minutes. After centrifugation, the supernatant was removed and the precipitate was washed with 75% ethanol. The precipitate was dissolved in 1.6 ml of water. This solution was precipitated with ethanol and the precipitate was washed with 75% ethanol, dried and dissolved in 0.4 ml of water to yield total RNA.

Then, mRNA was prepared using mRNA Isolation Kit (Stratagene). First, 10 ml of Elution Buffer was added to 0.2 ml of total RNA prepared above, and 5 ml of oligo dT solution was further added. After removing the supernatant, the oligo dT was washed three times with High Salt Buffer and twice with Low Salt Buffer and then eluted with Elution Buffer heated to 68° C. This solution was precipitated with ethanol and the precipitate was washed with 75% ethanol, dried and dissolved in 15 μl of water to yield mRNA fraction.

Then, cDNA of PCE I gene was prepared from the mRNA by RT-PCR using Takara RNA PCR Kit (AMV) Ver. 2.1. Thus, oligonucleotide primers having the following sequences were prepared as primers for N- and C-terminals deduced from the genomic PCE I gene sequence determined above and only cDNA of PCE I gene was amplified by PCR method using 1 μl of mRNA prepared above as a template.

PCEI-CN: 5'-GCGGATCCATGAAGTTCTCCATCATCG-3' (27 mer) (SEQIDNO:112)
PCEI-CC: 5'-GCGGATCCTTACTTGCGCTCGCAACCA-3' (27 mer) (SEQ ID NO:113)

The RT-PCR reaction was effected under the following conditions. First, the C-terminal primer was added to the reaction mixture and reacted with reverse transcriptase. Then, Taq polymerase (recombinant Taq, Takara Shuzo) and the N-terminal primer were added and the reaction conditions of 94° C. for 1 minute, 50° C. for 2 minutes and 72° C. for 2 minutes were repeated.30 times to amplify. As a result of agarose gel electrophoresis, the amplified fragment was of about 1.0 kbp. The fragment was subcloned into BamHI site of pUC118 and the nucleotide sequence of the fragment was determined according to the method of Example B3 (3). This nucleotide sequence was compared with the genomic nucleotide sequence to determine introns. As a result of this analysis, the entire nucleotide sequence of cDNA of Phycomyces nitens PCE I gene was determined.

Example G1

Evaluation of Fuzz Removal Action of Endoglucanase RCE I Expressed in *Humicola insolens* when Formulated as Detergent The cellulose containing fabric fuzz removal activity of the endoglucanase RCE I expressed in *Humicola insolens* obtained in Example D4 was evaluated in the following manner. Thus, the cultivation supernatant of the codon optimized endoglucanase RCE I expressed in *Humicola insolens* prepared in Example D4 was used in the fuzz removal treatment of a knitted cotton fabric (6 cm×8 cm) napped in a large washer containing a surfactant and rubber balls under the conditions as set forth below. The amount of cultivation supernatant required to completely remove the fuzz formed was determined. A cultivation supernatant derived from the untransformed recipient strain was used as a control.

Test machine: Launder Meter L-12 (Daiei Kagaku Seiki MPG., Japan)
Temperature: 40° C.
Time: 60 minutes
Reaction volume: 40 ml
Reaction pH: pH 8.5 (10 mM Tris buffer)

(Nonionic Surfactant)
Nonipol 100 (Sanyo Kasei Kogyo) 0.15 g/l
(Anionic Surfactant)
Shabondama Baby powder soap (Shabondama Soap Japan) 0.55 g/l The treating liquid contained an appropriate amount of rubber balls together with the endoglucanase solution. The results are shown in Table 7 below.

TABLE 7

| | Amount of the cultivation supernatant required to remove fuzz of cotton fabric (ml) |
|---|---|
| *Humicola insolens* MN200-1 (recipient) | Only about 60% of fuzz were removed even by addition of 2 ml. |
| *Humicola insolens* pJI4C01 (2-15) | 0.1 |

Example G2

Evaluation of Waste Paper Deinking by Endoglucanase RCE I Expressed in *Humicola insolens*

The centrifuged supernatant of a cultivation broth of codon optimized endoglucanase RCE I expressed in *Humicola insolens* prepared in Example D4 was further subjected to precise filtration (0.45 microns) and the whole amount was lyophilized to yield a crude enzyme powder. This crude enzyme powder had an HEC activity of 1920 units/g. To evaluate the enzymatic deinking power of this crude enzyme, the following enzymatic deinking test was carried out. Newspaper was digested in a shredder and 50 mM phosphate buffer (pH 6.0) was added at 50° C. as a concentration of 5% by weight. The newspaper was immersed for 10 minutes to swell. Thereafter, the newspaper was disintegrated by stirring 30,000 times in a JIS standard disintegrator heated at 50° C. To the disintegrated material, the enzyme solution corresponding to 3 mg (100 nkat) and 9 mg (300 nkat) of crude enzyme powder per g of disintegrated material was added. The mixture was thoroughly stirred and incubated at 60° C. for 120 minutes.

Thereafter, the enzymatically reacted disintegrated material was stirred 1000 times in a standard disintegrator to yield a homogeneously disintegrated material. One volume of the resulting disintegrated material was diluted with 4 volumes of tap water. A deinking agent (Raisapon 104.1 g/L) and potassium chloride (200 mg/L) were added and subjected to voith flotation cell. Flotation was carried out at 50 deg. for 5 minutes while floated ink was removed out.

Thereafter, a hand made sheet was prepared and dried. ISO brightness of the resulting waste paper was measured by a whiteness meter and the area of remaining ink was measured by Quick Scan 35 (Minolta). The analysis results of the three samples, one non-treated zone and two enzymatically treated experimental zones (100 nka/g, 300 nkat/g) by the above procedure are shown in Table 8. From the results, the effectiveness of RCE I on deinking of waste paper was confirmed since the brightness of waste paper obtained from the enzyme experimental zones was superior to the brightness of non-treated waste paper.

TABLE 8

| Concentration of enzyme added | Brightness | Area of remaining ink % |
| --- | --- | --- |
| None | 46.9 | 1.19 |
| 100 nkat/g | 47.6 | |
| 300 nkat/g | 48.5 | 1.06 |

What is claimed is:

1. An isolated endoglucanase comprising the amino acid sequence as shown in SEQ ID NO: 1, 3, 5, 7, 9 or 11.

2. An isolated polynucleotide comprising a nucleotide sequence encoding the endoglucanase according to claim 1.

3. The polynucleotide according to claim 1, wherein said polynucleotide comprises the DNA sequence as shown in SEQ ID NO: 2, 4, 6, 8, 10 or 12.

4. The polynucleotide according to claim 1, wherein said polynucleotide comprises a nucleotide sequence in which codons have been optimized for a host by selecting those codons frequently used by the host.

5. The polynucleotide according to claim 4, wherein said nucleotide sequence in which codons have been optimized is the DNA sequence as shown in SEQ ID NO: 13.

6. An expression vector comprising the polynucleotide according to claim 2.

7. A host cell transformed with the polynucleotide according to claim 2.

8. The host cell according to claim 7, wherein said host cell is a yeast or filamentous fungus.

9. The host cell according to claim 8, wherein the yeast belongs to the genus *Saccharomyces,* the genus *Hansenula* or the genus *Pichia.*

10. The host cell according to claim 8, wherein the yeast is *Saccharomyces cerevisiae.*

11. The host cell according to claim 8, wherein the filamentous fungus belongs to the genus *Humicola,* the genus *Aspergillus,* the genus *Trichoderma,* the genus *Acremonium* or the genus *Fusarium.*

12. The host cell according to claim 8, wherein the filamentous fungus is *Humicola insolens, Aspergillus niger* or *Trichoderma viride.*

13. A method for producing the endoglucanase, comprising cultivating the host cell according to claim 7 and recovering the endoglucanase from said host cell and/or the resultant cultivation broth.

14. An endoglucanase produced by the method according to claim 13.

15. A cellulase preparation comprising the endoglucanase according to claim 1.

16. A method of treating cellulose-containing fabrics, comprising a step of contacting the cellulose-containing fabrics with the endoglucanase according to claim 1.

17. A method of reducing the rate at which cellulose-containing fabrics become fuzzy or for reducing fuzzing in cellulose-containing fabrics, comprising a step of contacting the cellulose-containing fabrics with the endoglucanase according to claim 1.

18. A method of weight loss treatment for cellulose-containing fabrics to improve its touch and appearance, comprising a step of contacting the cellulose-containing fabrics with the endoglucanase according to claim 1.

19. A method of providing color clarification of colored cellulose-containing fabrics, comprising a step of treating the colored cellulose-containing fabrics with the endoglucanase according to claim 1.

20. A method of providing a localized variation in color of colored cellulose-containing fabrics, comprising a step of treating the colored cellulose-containing fabrics with the endoglucanase according to claim 1.

21. A method of reducing the rate at which cellulose-containing fabrics become stiff or reducing stiffness in cellulose-containing fabrics, comprising a step of treating the cellulose-containing fabrics with the endoglucanase according to claim 1.

22. The method according to claim 16, wherein the treatment of the fabrics is performed through soaking, washing or rinsing the fabrics.

23. An additive to detergent comprising the endoglucanase according to claim 1 in a non-scattering granular form or a stabilized liquid form.

24. A detergent composition comprising the endoglucanase according to claim 1.

25. A method of improving the freeness of a paper pulp, comprising a step of treating the paper pulp with the endoglucanase according to claim 1.

26. A method of deinking a waste paper, comprising a step of treating the waste paper with the endoglucanase according to claim 1 in the presence of a deinking agent.

27. A method of improving the digestibility of an animal feed, comprising a step of treating a cellulose-containing feed with the endoglucanase according to claim 1.

28. An isolated endoglucanase comprising the amino acid sequence as shown in SEQ ID NO: 1, 3, 5, 7, 9 or 11, the endoglucanase exhibiting endoglucanase activity at a pH of about 6.5 to about 9.5.

* * * * *

SEQUENCE LISTING

<160> NUMBER OF SEQ ID NOS: 113

<210> SEQ ID NO 1
<211> LENGTH: 338
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(315)

<400> SEQUENCE: 1

```
Met Lys Phe Ile Thr Ile Ala Ser Ser Ala Leu Leu Ala Leu Ala Leu
            -20                 -15                 -10

Gly Thr Glu Met Ala Ser Ala Ala Glu Cys Ser Lys Leu Tyr Gly Gln
         -5                   1               5

Cys Gly Gly Lys Asn Trp Asn Gly Pro Thr Cys Cys Glu Ser Gly Ser
 10                  15                  20                  25

Thr Cys Lys Val Ser Asn Asp Tyr Tyr Ser Gln Cys Leu Pro Ser Gly
                 30                  35                  40

Ser Ser Gly Asn Lys Ser Ser Glu Ser Ala His Lys Lys Thr Thr Thr
             45                  50                  55

Ala Ala His Lys Lys Thr Thr Ala Ala His Lys Lys Thr Thr Thr
             60                  65                  70

Ala Pro Ala Lys Lys Thr Thr Val Ala Lys Ala Ser Thr Pro Ser
         75                  80                  85

Asn Ser Ser Ser Ser Ser Ser Gly Lys Tyr Ser Ala Val Ser Gly Gly
 90                  95                 100                 105

Ala Ser Gly Asn Gly Val Thr Thr Arg Tyr Trp Asp Cys Cys Lys Ala
                110                 115                 120

Ser Cys Ser Trp Pro Gly Lys Ala Asn Val Ser Ser Pro Val Lys Ser
                125                 130                 135

Cys Asn Lys Asp Gly Val Thr Ala Leu Ser Asp Ser Asn Ala Gln Ser
                140                 145                 150
```

-continued

```
Gly Cys Asn Gly Gly Asn Ser Tyr Met Cys Asn Asp Asn Gln Pro Trp
155                 160                 165

Ala Val Asn Asp Asn Leu Ala Tyr Gly Phe Ala Ala Ala Ile Ser
170                 175                 180                 185

Gly Gly Gly Glu Ser Arg Trp Cys Cys Ser Cys Phe Glu Leu Thr Phe
                190                 195                 200

Thr Ser Thr Ser Val Ala Gly Lys Lys Met Val Val Gln Val Thr Asn
            205                 210                 215

Thr Gly Gly Asp Leu Gly Ser Ser Thr Gly Ala His Phe Asp Leu Gln
        220                 225                 230

Met Pro Gly Gly Val Gly Ile Phe Asn Gly Cys Ser Ser Gln Trp
    235                 240                 245

Gly Ala Pro Asn Asp Gly Trp Gly Ser Arg Tyr Gly Gly Ile Ser Ser
250                 255                 260                 265

Ala Ser Asp Cys Ser Ser Leu Pro Ser Ala Leu Gln Ala Gly Cys Lys
                270                 275                 280

Trp Arg Phe Asn Trp Phe Lys Asn Ala Asp Asn Pro Ser Met Thr Tyr
            285                 290                 295

Lys Glu Val Thr Cys Pro Lys Glu Ile Thr Ala Lys Thr Gly Cys Ser
        300                 305                 310

Arg Lys
    315

<210> SEQ ID NO 2
<211> LENGTH: 1017
<212> TYPE: DNA
<213> ORGANISM: Rhizopus oryzae CP96001
<220> FEATURE:
<221> NAME/KEY: sig_peptide
<222> LOCATION: (1)..(69)
<220> FEATURE:
<221> NAME/KEY: mat_peptide
<222> LOCATION: (70)..(1017)

<400> SEQUENCE: 2 atg aag ttt att act att gcc tct tcc gct ctc ttg gct ctc gcc ctc      48
Met Lys Phe Ile Thr Ile Ala Ser Ser Ala Leu Leu Ala Leu Ala Leu
            -20                 -15                 -10 ggt act gaa atg gcc tct gct gct gaa tgt agc aaa ttg tat ggt caa      96
Gly Thr Glu Met Ala Ser Ala Ala Glu Cys Ser Lys Leu Tyr Gly Gln
        -5                   1               5 tgt ggt ggt aag aac tgg aat ggc cct act tgt tgt gaa tct gga tcc     144
Cys Gly Gly Lys Asn Trp Asn Gly Pro Thr Cys Cys Glu Ser Gly Ser
 10                  15                  20                  25 acc tgt aaa gta agc aac gat tac tac tct caa tgt ctt ccc tct gga     192
Thr Cys Lys Val Ser Asn Asp Tyr Tyr Ser Gln Cys Leu Pro Ser Gly
                 30                  35                  40 agc agt ggc aat aaa tct tct gaa agt gct cac aag aag act acc act     240
Ser Ser Gly Asn Lys Ser Ser Glu Ser Ala His Lys Lys Thr Thr Thr
             45                  50                  55 gct gct cac aag aag act act acc gct gct cat aaa aag act acc act     288
Ala Ala His Lys Lys Thr Thr Thr Ala Ala His Lys Lys Thr Thr Thr
         60                  65                  70 gct cct gct aag aag act aca act gtt gcc aaa gct tcc acc cct tct     336
Ala Pro Ala Lys Lys Thr Thr Thr Val Ala Lys Ala Ser Thr Pro Ser
     75                  80                  85 aac tct agc tct agc tcc agc ggc aaa tat tcc gct gtc tct ggt ggt     384
Asn Ser Ser Ser Ser Ser Gly Lys Tyr Ser Ala Val Ser Gly Gly
 90                  95                 100                 105
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gcc | tct | ggt | aac | ggt | gtc | act | act | cgt | tat | tgg | gat | tgc | tgt | aag | gcc | 432 |
| Ala | Ser | Gly | Asn | Gly | Val | Thr | Thr | Arg | Tyr | Trp | Asp | Cys | Cys | Lys | Ala | |
|     |     |     |     | 110 |     |     |     |     | 115 |     |     |     |     | 120 |     |     |
| tcc | tgt | agc | tgg | ccc | ggt | aag | gcc | aat | gtc | agt | tct | cct | gtc | aag | tcc | 480 |
| Ser | Cys | Ser | Trp | Pro | Gly | Lys | Ala | Asn | Val | Ser | Ser | Pro | Val | Lys | Ser | |
|     |     | 125 |     |     |     |     | 130 |     |     |     |     | 135 |     |     |     |     |
| tgt | aac | aaa | gat | ggt | gtc | act | gcc | ctt | agt | gac | agc | aat | gcc | caa | agt | 528 |
| Cys | Asn | Lys | Asp | Gly | Val | Thr | Ala | Leu | Ser | Asp | Ser | Asn | Ala | Gln | Ser | |
|     | 140 |     |     |     |     | 145 |     |     |     |     | 150 |     |     |     |     |     |
| ggc | tgt | aac | ggt | ggt | aac | agt | tac | atg | tgt | aac | gac | aac | caa | cct | tgg | 576 |
| Gly | Cys | Asn | Gly | Gly | Asn | Ser | Tyr | Met | Cys | Asn | Asp | Asn | Gln | Pro | Trp | |
| 155 |     |     |     |     | 160 |     |     |     |     | 165 |     |     |     |     |     |     |
| gct | gta | aac | gac | aac | ctt | gcc | tat | ggt | ttc | gct | gct | gct | gcc | atc | agt | 624 |
| Ala | Val | Asn | Asp | Asn | Leu | Ala | Tyr | Gly | Phe | Ala | Ala | Ala | Ala | Ile | Ser | |
| 170 |     |     |     |     | 175 |     |     |     |     | 180 |     |     |     |     | 185 |     |
| ggt | ggt | ggt | gaa | tct | cgc | tgg | tgc | tgt | tct | tgt | ttc | gaa | ctt | act | ttc | 672 |
| Gly | Gly | Gly | Glu | Ser | Arg | Trp | Cys | Cys | Ser | Cys | Phe | Glu | Leu | Thr | Phe | |
|     |     |     |     | 190 |     |     |     |     | 195 |     |     |     |     | 200 |     |     |
| act | tct | acc | tct | gtt | gct | ggt | aag | aag | atg | gtt | gtc | caa | gtc | act | aac | 720 |
| Thr | Ser | Thr | Ser | Val | Ala | Gly | Lys | Lys | Met | Val | Val | Gln | Val | Thr | Asn | |
|     |     |     | 205 |     |     |     |     | 210 |     |     |     |     | 215 |     |     |     |
| act | ggt | ggt | gat | ctt | ggc | tcc | tct | act | ggt | gct | cac | ttt | gac | ttg | caa | 768 |
| Thr | Gly | Gly | Asp | Leu | Gly | Ser | Ser | Thr | Gly | Ala | His | Phe | Asp | Leu | Gln | |
|     |     | 220 |     |     |     |     | 225 |     |     |     |     | 230 |     |     |     |     |
| atg | ccc | ggt | ggt | ggt | gtt | ggt | att | ttc | aat | ggt | tgt | tcc | agc | caa | tgg | 816 |
| Met | Pro | Gly | Gly | Gly | Val | Gly | Ile | Phe | Asn | Gly | Cys | Ser | Ser | Gln | Trp | |
| 235 |     |     |     |     | 240 |     |     |     |     | 245 |     |     |     |     |     |     |
| ggt | gct | ccc | aat | gac | ggt | tgg | ggc | tca | aga | tac | ggt | ggt | att | tct | tct | 864 |
| Gly | Ala | Pro | Asn | Asp | Gly | Trp | Gly | Ser | Arg | Tyr | Gly | Gly | Ile | Ser | Ser | |
| 250 |     |     |     |     | 255 |     |     |     |     | 260 |     |     |     |     | 265 |     |
| gca | tct | gac | tgc | tct | agt | ctt | cct | tcc | gca | ctc | caa | gct | ggt | tgt | aaa | 912 |
| Ala | Ser | Asp | Cys | Ser | Ser | Leu | Pro | Ser | Ala | Leu | Gln | Ala | Gly | Cys | Lys | |
|     |     |     |     | 270 |     |     |     |     | 275 |     |     |     |     | 280 |     |     |
| tgg | aga | ttc | aac | tgg | ttc | aag | aac | gct | gat | aac | cca | agc | atg | act | tac | 960 |
| Trp | Arg | Phe | Asn | Trp | Phe | Lys | Asn | Ala | Asp | Asn | Pro | Ser | Met | Thr | Tyr | |
|     |     | 285 |     |     |     |     | 290 |     |     |     |     | 295 |     |     |     |     |
| aag | gaa | gtt | acc | tgt | cct | aag | gaa | atc | acc | gcc | aag | aca | ggt | tgt | tca | 1008 |
| Lys | Glu | Val | Thr | Cys | Pro | Lys | Glu | Ile | Thr | Ala | Lys | Thr | Gly | Cys | Ser | |
|     | 300 |     |     |     |     | 305 |     |     |     |     | 310 |     |     |     |     |     |
| aga | aaa | taa |     |     |     |     |     |     |     |     |     |     |     |     |     | 1017 |
| Arg | Lys |     |     |     |     |     |     |     |     |     |     |     |     |     |     |     |
| 315 |     |     |     |     |     |     |     |     |     |     |     |     |     |     |     |     |

<210> SEQ ID NO 3
<211> LENGTH: 366
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(343)

<400> SEQUENCE: 3

Met Lys Phe Ile Thr Ile Thr Ser Ser Ala Leu Leu Ala Leu Ala Leu
            -20                 -15                 -10

Gly Thr Glu Met Ala Ser Ala Ala Lys Cys Ser Lys Leu Tyr Gly Gln
        -5                   1               5

Cys Gly Gly Lys Asp Trp Asn Gly Pro Thr Cys Cys Glu Ser Gly Ser
 10                  15                  20                  25

```
Thr Cys Lys Val Ser Asn Asp Tyr Tyr Ser Gln Cys Leu Ala Pro Glu
            30                  35                  40

Ser Asn Gly Asn Lys Ser Ser Glu Cys Ser Lys Leu Tyr Gly Gln Cys
                45                  50                  55

Gly Gly Lys Asp Trp Asn Gly Pro Thr Cys Cys Glu Ser Gly Ser Thr
            60                  65                  70

Cys Lys Val Ser Asn Asp Tyr Tyr Ser Gln Cys Leu Ala Pro Glu Ser
        75                  80                  85

Asn Gly Asn Lys Thr Ser Glu Ser Ala His Lys Thr Thr Thr Thr Thr
 90                  95                 100                 105

Ala Pro Ala Lys Glu Ile Thr Thr Ala Lys Ala Ser Asn Ser Ser
                110                 115                 120

Asn Ser Ser Gly Lys Tyr Ser Ile Val Ser Gly Ala Ser Gly Asn
                125                 130                 135

Gly Val Thr Thr Arg Tyr Trp Asp Cys Cys Lys Ala Ser Cys Ser Trp
170         140                 145                 150

Pro Gly Lys Ala Asn Val Ser Ser Pro Val Lys Ser Cys Asn Lys Asp
        155                 160                 165

Gly Val Thr Ala Leu Ser Asp Ser Asn Val Gln Ser Gly Cys Asn Gly
170                 175                 180                 185

Gly Asn Ser Tyr Met Cys Asn Asp Asn Gln Pro Trp Ala Val Asn Asp
                190                 195                 200

Asn Leu Ala Tyr Gly Phe Ala Ala Ala Ile Ser Gly Gly Gly Glu
                205                 210                 215

Ser Arg Trp Cys Cys Ser Cys Phe Glu Leu Thr Phe Thr Ser Thr Ser
        220                 225                 230

Val Ala Gly Lys Lys Met Val Ile Gln Val Thr Asn Thr Gly Gly Asp
        235                 240                 245

Leu Gly Ser Ser Thr Gly Ala His Phe Asp Leu Gln Met Pro Gly Gly
250                 255                 260                 265

Gly Val Gly Ile Phe Asn Gly Cys Ser Lys Gln Trp Gly Ala Pro Asn
                270                 275                 280

Asp Gly Trp Gly Ser Arg Tyr Gly Gly Ile Ser Ser Ala Ser Asp Cys
            285                 290                 295

Ser Ser Leu Pro Ser Ala Leu Gln Ala Gly Cys Lys Trp Arg Phe Asn
            300                 305                 310

Trp Phe Lys Asn Ala Asp Asn Pro Ser Met Thr Tyr Lys Glu Val Thr
        315                 320                 325

Cys Pro Lys Glu Ile Thr Ala Lys Thr Gly Cys Ser Arg Lys
330                 335                 340

<210> SEQ ID NO 4
<211> LENGTH: 1101
<212> TYPE: DNA
<213> ORGANISM: Rhizopus oryzae CP96001
<220> FEATURE:
<221> NAME/KEY: sig_peptide
<222> LOCATION: (1)..(69)
<220> FEATURE:
<221> NAME/KEY: mat_peptide
<222> LOCATION: (70)..(1101)

<400> SEQUENCE: 4 atg aag ttt att act att acc tct tcc gct ctc ttg gct ctc gcc ctt    48
Met Lys Phe Ile Thr Ile Thr Ser Ser Ala Leu Leu Ala Leu Ala Leu
            -20                 -15                 -10
```

-continued

| | |
|---|---|
| ggt act gaa atg gcc tct gct gct aaa tgt agc aag ctg tat ggt caa<br>Gly Thr Glu Met Ala Ser Ala Ala Lys Cys Ser Lys Leu Tyr Gly Gln<br>       -5                        1                   5 | 96 |
| tgt ggt ggt aag gac tgg aat ggc cct act tgt tgc gaa tct gga tcc<br>Cys Gly Gly Lys Asp Trp Asn Gly Pro Thr Cys Cys Glu Ser Gly Ser<br>10                   15                     20                    25 | 144 |
| acc tgt aaa gta agc aac gat tac tac tct caa tgt ctt gcc cct gaa<br>Thr Cys Lys Val Ser Asn Asp Tyr Tyr Ser Gln Cys Leu Ala Pro Glu<br>                 30                        35                      40 | 192 |
| agc aac ggc aat aag tct tct gaa tgt agc aag ttg tat ggt caa tgt<br>Ser Asn Gly Asn Lys Ser Ser Glu Cys Ser Lys Leu Tyr Gly Gln Cys<br>                 45                        50                      55 | 240 |
| ggt ggt aag gac tgg aat ggc cct act tgt tgc gaa tct gga tcc acc<br>Gly Gly Lys Asp Trp Asn Gly Pro Thr Cys Cys Glu Ser Gly Ser Thr<br>                 60                        65                      70 | 288 |
| tgt aaa gta agc aac gat tac tac tct caa tgt ctt gcc cct gaa agc<br>Cys Lys Val Ser Asn Asp Tyr Tyr Ser Gln Cys Leu Ala Pro Glu Ser<br>75                   80                     85 | 336 |
| aat ggc aat aaa act tct gaa agc gct cat aaa acg act act acc act<br>Asn Gly Asn Lys Thr Ser Glu Ser Ala His Lys Thr Thr Thr Thr Thr<br>90                   95                     100                  105 | 384 |
| gct ccc gct aag gaa att aca act act gcc aaa gct tca aac tct tct<br>Ala Pro Ala Lys Glu Ile Thr Thr Thr Ala Lys Ala Ser Asn Ser Ser<br>                    110                        115                  120 | 432 |
| aac tct agc ggc aaa tac tcc att gtc tct ggt ggt gcc tct ggt aac<br>Asn Ser Ser Gly Lys Tyr Ser Ile Val Ser Gly Gly Ala Ser Gly Asn<br>             125                        130                      135 | 480 |
| ggt gtc act act cgt tat tgg gat tgc tgt aag gcc tcc tgt agc tgg<br>Gly Val Thr Thr Arg Tyr Trp Asp Cys Cys Lys Ala Ser Cys Ser Trp<br>                 140                        145                      150 | 528 |
| ccc ggt aag gcc aat gtc agt tct cct gtc aag tcc tgt aac aaa gat<br>Pro Gly Lys Ala Asn Val Ser Ser Pro Val Lys Ser Cys Asn Lys Asp<br>155                   160                     165 | 576 |
| ggt gtc act gcc ctt agt gac agc aat gtc caa agt ggc tgt aac ggt<br>Gly Val Thr Ala Leu Ser Asp Ser Asn Val Gln Ser Gly Cys Asn Gly<br>170                   175                     180                  185 | 624 |
| ggt aac agt tac atg tgt aac gac aac cag cct tgg gct gta aac gat<br>Gly Asn Ser Tyr Met Cys Asn Asp Asn Gln Pro Trp Ala Val Asn Asp<br>                    190                        195                  200 | 672 |
| aat ctt gcc tat ggt ttc gct gct gct gcc atc agt ggt ggt ggt gaa<br>Asn Leu Ala Tyr Gly Phe Ala Ala Ala Ala Ile Ser Gly Gly Gly Glu<br>             205                        210                      215 | 720 |
| tct cgc tgg tgc tgt tct tgt ttc gaa ctt act ttc act tct acc tct<br>Ser Arg Trp Cys Cys Ser Cys Phe Glu Leu Thr Phe Thr Ser Thr Ser<br>             220                        225                      230 | 768 |
| gtt gct ggt aag aag atg gtt atc caa gtc act aac act ggt ggt gat<br>Val Ala Gly Lys Lys Met Val Ile Gln Val Thr Asn Thr Gly Gly Asp<br>235                   240                     245 | 816 |
| ctt ggc tcc tct act ggt gct cac ttt gac ttg caa atg ccc ggt ggt<br>Leu Gly Ser Ser Thr Gly Ala His Phe Asp Leu Gln Met Pro Gly Gly<br>250                   255                     260                  265 | 864 |
| ggt gtt ggt att ttc aat ggt tgc tcc aag caa tgg ggt gct ccc aat<br>Gly Val Gly Ile Phe Asn Gly Cys Ser Lys Gln Trp Gly Ala Pro Asn<br>             270                        275                      280 | 912 |
| gac ggt tgg ggc tcg aga tac ggt ggt att tct tct gca tct gac tgc<br>Asp Gly Trp Gly Ser Arg Tyr Gly Gly Ile Ser Ser Ala Ser Asp Cys<br>                 285                        290                      295 | 960 |
| tct agt ctt cct tcc gca ctc caa gct ggt tgt aaa tgg aga ttc aac<br>Ser Ser Leu Pro Ser Ala Leu Gln Ala Gly Cys Lys Trp Arg Phe Asn<br>             300                        305                      310 | 1008 |

-continued

```
tgg ttc aag aac gct gat aac cca agc atg act tac aag gaa gtt acc    1056
Trp Phe Lys Asn Ala Asp Asn Pro Ser Met Thr Tyr Lys Glu Val Thr
315                 320                 325 tgt ccc aag gaa atc acc gcc aag aca ggt tgt tca aga aaa taa        1101
Cys Pro Lys Glu Ile Thr Ala Lys Thr Gly Cys Ser Arg Lys
330                 335                 340
```

<210> SEQ ID NO 5
<211> LENGTH: 360
<212> TYPE: PRT
<213> ORGANISM: Rhizopus oryzae CP96001
<220> FEATURE:
<221> NAME/KEY: sig_peptide
<222> LOCATION: (-23)..(-1)
<220> FEATURE:
<221> NAME/KEY: mat_peptide
<222> LOCATION: (1)..(337)

<400> SEQUENCE: 5

```
Met Lys Phe Leu Thr Ile Ala Ser Ser Ala Ile Leu Ala Leu Ala Val
            -20                 -15                 -10

Gly Thr Glu Met Ala His Ala Ala Glu Cys Ser Lys Ala Tyr Tyr Gln
         -5                   1               5

Cys Gly Gly Lys Asn Trp Asp Gly Pro Thr Cys Cys Glu Ser Gly Ser
 10                  15                  20                  25

Thr Cys Val Asp Tyr Pro Asp Asn Pro Phe Tyr Ser Gln Cys Val Pro
                 30                  35                  40

Asn Glu Asn Leu Thr Ser Thr Asn Lys Ser Ser His Lys Thr Thr Thr
             45                  50                  55

Thr Glu Ser Ala Lys Lys Thr Thr Thr Lys Gly Ser Lys Lys Thr
         60                  65                  70

Thr Thr Thr Glu Ala Ser Lys Lys Thr Thr Thr Glu Ala Ser Lys
 75                  80                  85

Lys Thr Thr Thr Thr Glu Ala Ser Lys Lys Thr Thr Thr Thr Lys
 90                  95                 100                 105

Lys Ala Ser Thr Ser Thr Ser Ser Ser Ser Ser Ala Ser Thr Asn
                110                 115                 120

Tyr Ser Ala Val Ser Gly Gly Ala Ser Gly Asn Gly Glu Thr Thr Arg
                125                 130                 135

Tyr Trp Asp Cys Cys Lys Pro Ser Cys Ser Trp Pro Gly Lys Ala Asp
         140                 145                 150

Val Thr Ser Pro Val Gly Ser Cys Asn Lys Asp Gly Lys Thr Leu Ala
 155                 160                 165

Asp Asn Thr Gln Asn Gly Cys Val Gly Gly Ser Ser Tyr Thr Cys
170                 175                 180                 185

Asn Asp Asn Gln Pro Trp Val Val Ser Asp Leu Ala Tyr Gly Phe
                190                 195                 200

Ala Ala Ala Ser Ile Ser Gly Ser Glu Ala Thr Trp Cys Cys Ala
             205                 210                 215

Cys Phe Glu Leu Thr Phe Thr Ser Thr Ala Val Lys Gly Lys Met
         220                 225                 230

Val Val Gln Val Thr Asn Thr Gly Ser Asp Leu Gly Ser Asn Thr Gly
 235                 240                 245

Ala His Phe Asp Leu Gln Met Pro Gly Gly Gly Val Gly Ile Tyr Asn
250                 255                 260                 265

Gly Cys Ala Thr Gln Trp Gly Ala Pro Thr Asp Gly Trp Gly Ala Arg
                270                 275                 280
```

```
Tyr Gly Gly Val Ser Ser Ala Ser Asp Cys Ser Asn Leu Pro Ser Ala
            285                 290                 295

Leu Gln Ala Gly Cys Lys Trp Arg Phe Gly Trp Phe Lys Asn Ala Asp
        300                 305                 310

Asn Pro Thr Met Thr Tyr Lys Gln Val Thr Cys Pro Lys Ala Ile Thr
        315                 320                 325

Ala Lys Ser Gly Cys Ser Arg Lys
330                 335

<210> SEQ ID NO 6
<211> LENGTH: 1083
<212> TYPE: DNA
<213> ORGANISM: Rhizopus oryzae CP96001
<220> FEATURE:
<221> NAME/KEY: sig_peptide
<222> LOCATION: (1)..(69)
<220> FEATURE:
<221> NAME/KEY: mat_peptide
<222> LOCATION: (70)..(1083)

<400> SEQUENCE: 6 atg aag ttc ctt acc att gcc tcc tcc gct atc ttg gca ctt gcc gtc      48
Met Lys Phe Leu Thr Ile Ala Ser Ser Ala Ile Leu Ala Leu Ala Val
            -20                 -15                 -10 ggt act gaa atg gcc cat gct gct gaa tgt agc aag gct tac tac caa      96
Gly Thr Glu Met Ala His Ala Ala Glu Cys Ser Lys Ala Tyr Tyr Gln
        -5                   1               5 tgt ggt ggt aag aac tgg gat gga cct acc tgc tgt gaa tct ggc tct     144
Cys Gly Gly Lys Asn Trp Asp Gly Pro Thr Cys Cys Glu Ser Gly Ser
 10                  15                  20                  25 act tgc gtt gat tat cct gac aat cct ttc tac tcc caa tgt gtt ccc     192
Thr Cys Val Asp Tyr Pro Asp Asn Pro Phe Tyr Ser Gln Cys Val Pro
             30                  35                  40 aat gaa aac ctc acc tcc act aac aaa tct tct cac aaa acc acc act     240
Asn Glu Asn Leu Thr Ser Thr Asn Lys Ser Ser His Lys Thr Thr Thr
             45                  50                  55 act gag agt gcc aag aag act acc act act aaa ggt tcc aag aag acc     288
Thr Glu Ser Ala Lys Lys Thr Thr Thr Thr Lys Gly Ser Lys Lys Thr
         60                  65                  70 acc act act gaa gcc tct aag aag acc acc act act gaa gct tcc aag     336
Thr Thr Thr Glu Ala Ser Lys Lys Thr Thr Thr Thr Glu Ala Ser Lys
     75                  80                  85 aag acc acc act act gaa gcc tct aag aag acc acc act act act aag     384
Lys Thr Thr Thr Thr Glu Ala Ser Lys Lys Thr Thr Thr Thr Thr Lys
 90                  95                 100                 105 aag gct tct acc tcc act tcc tct tcc tct tct gct tct aca aac         432
Lys Ala Ser Thr Ser Thr Ser Ser Ser Ser Ser Ala Ser Thr Asn
                110                 115                 120 tac tcc gct gtc tct ggt ggt gcc tcc ggt aat ggt gaa acc act cgc     480
Tyr Ser Ala Val Ser Gly Gly Ala Ser Gly Asn Gly Glu Thr Thr Arg
            125                 130                 135 tac tgg gat tgt tgt aag cct tct tgc agt tgg ccc ggt aag gct gat     528
Tyr Trp Asp Cys Cys Lys Pro Ser Cys Ser Trp Pro Gly Lys Ala Asp
        140                 145                 150 gtc acc tcc cct gtt ggc tcc tgt aac aag gat ggt aag act ctt gct     576
Val Thr Ser Pro Val Gly Ser Cys Asn Lys Asp Gly Lys Thr Leu Ala
        155                 160                 165 gat aac aac act caa aac ggc tgt gtt ggt ggt agc agc tac acc tgt     624
Asp Asn Asn Thr Gln Asn Gly Cys Val Gly Gly Ser Ser Tyr Thr Cys
170                 175                 180                 185
```

| | | |
|---|---|---|
| aat gac aat caa cct tgg gtt gtt agc gac gac ctt gcc tac ggt ttc<br>Asn Asp Asn Gln Pro Trp Val Val Ser Asp Asp Leu Ala Tyr Gly Phe<br>190                  195                  200 | | 672 |
| gcc gct gct tcc att tct ggt ggt agc gaa gct act tgg tgt tgt gcc<br>Ala Ala Ala Ser Ile Ser Gly Gly Ser Glu Ala Thr Trp Cys Cys Ala<br>        205                  210                  215 | | 720 |
| tgt ttc gaa ctc aca ttc acc tct act gcc gtc aag ggt aag aag atg<br>Cys Phe Glu Leu Thr Phe Thr Ser Thr Ala Val Lys Gly Lys Lys Met<br>220                  225                  230 | | 768 |
| gtt gtt caa gta acc aac act ggt tct gac ctt ggc tct aac act ggt<br>Val Val Gln Val Thr Asn Thr Gly Ser Asp Leu Gly Ser Asn Thr Gly<br>        235                  240                  245 | | 816 |
| gct cac ttt gac ttg caa atg ccc ggt ggt ggt gtt ggt atc tac aat<br>Ala His Phe Asp Leu Gln Met Pro Gly Gly Gly Val Gly Ile Tyr Asn<br>250                  255                  260                  265 | | 864 |
| ggt tgt gcc act caa tgg ggt gct ccc acc gat ggt tgg ggt gca aga<br>Gly Cys Ala Thr Gln Trp Gly Ala Pro Thr Asp Gly Trp Gly Ala Arg<br>        270                  275                  280 | | 912 |
| tac ggc ggt gtt tct tct gcc tct gac tgt tct aac ctt cct tct gcc<br>Tyr Gly Gly Val Ser Ser Ala Ser Asp Cys Ser Asn Leu Pro Ser Ala<br>285                  290                  295 | | 960 |
| ctt caa gct ggt tgt aag tgg aga ttc ggc tgg ttc aaa aac gct gat<br>Leu Gln Ala Gly Cys Lys Trp Arg Phe Gly Trp Phe Lys Asn Ala Asp<br>        300                  305                  310 | | 1008 |
| aac cca acc atg acc tac aaa caa gtt acc tgt ccc aag gct atc act<br>Asn Pro Thr Met Thr Tyr Lys Gln Val Thr Cys Pro Lys Ala Ile Thr<br>315                  320                  325 | | 1056 |
| gcc aag tct ggc tgt tca aga aaa taa<br>Ala Lys Ser Gly Cys Ser Arg Lys<br>330                  335 | | 1083 |

<210> SEQ ID NO 7
<211> LENGTH: 338
<212> TYPE: PRT
<213> ORGANISM: Mucor circinelloides CP99001
<220> FEATURE:
<221> NAME/KEY: sig_peptide
<222> LOCATION: (-22)..(-1)
<220> FEATURE:
<221> NAME/KEY: mat_peptide
<222> LOCATION: (1)..(316)

<400> SEQUENCE: 7

Met Lys Phe Thr Val Ala Ile Thr Ser Ile Ala Val Ala Leu Ala Leu
        -20                  -15                      -10

Ser Ser Ser Ala Glu Ala Ala Ser Cys Ser Ser Val Tyr Gly Gln Cys
    -5                      1                  5                      10

Gly Gly Ile Gly Trp Ser Gly Pro Thr Cys Cys Glu Ser Gly Ser Thr
                15                  20                  25

Cys Val Ala Gln Glu Gly Asn Lys Tyr Tyr Ser Gln Cys Leu Pro Gly
        30                  35                  40

Ser His Ser Asn Asn Ala Gly Asn Ala Ser Ser Thr Lys Lys Thr Ser
                45                  50                  55

Thr Lys Thr Ser Thr Thr Thr Ala Lys Ala Thr Ala Thr Val Thr Thr
        60                  65                  70

Lys Thr Val Thr Lys Thr Thr Lys Thr Thr Lys Thr Ser Thr
    75                  80                  85                  90

Thr Ala Ala Ala Ser Thr Ser Thr Ser Ser Ala Gly Tyr Lys Val
                95                  100                 105

Ile Ser Gly Gly Lys Ser Gly Ser Gly Ser Thr Thr Arg Tyr Trp Asp

-continued

```
                    110                 115                 120
Cys Cys Lys Ala Ser Cys Ser Trp Pro Gly Lys Ala Ser Val Thr Gly
            125                 130                 135
Pro Val Asp Thr Cys Ala Ser Asn Gly Ile Ser Leu Leu Asp Ala Asn
        140                 145                 150
Ala Gln Ser Gly Cys Asn Gly Gly Asn Gly Phe Met Cys Asn Asn Asn
155                 160                 165                 170
Gln Pro Trp Ala Val Asn Asp Glu Leu Ala Tyr Gly Phe Ala Ala Ala
                175                 180                 185
Ser Ile Ala Gly Ser Asn Glu Ala Gly Trp Cys Cys Gly Cys Tyr Glu
            190                 195                 200
Leu Thr Phe Thr Ser Gly Ala Ala Ser Gly Lys Lys Met Val Val Gln
        205                 210                 215
Val Thr Asn Thr Gly Gly Asp Leu Gly Ser Asn His Phe Asp Leu Gln
    220                 225                 230
Met Pro Gly Gly Val Gly Ile Phe Asn Gly Cys Ala Ala Gln Trp
235                 240                 245                 250
Gly Ala Pro Asn Asp Gly Trp Gly Ala Arg Tyr Gly Gly Val Ser Ser
                255                 260                 265
Val Ser Asp Cys Ala Ser Leu Pro Ser Ala Leu Gln Ala Gly Cys Lys
            270                 275                 280
Trp Arg Phe Asn Trp Phe Lys Asn Ser Asp Asn Pro Thr Met Thr Phe
        285                 290                 295
Lys Glu Val Thr Cys Pro Ala Glu Leu Thr Thr Arg Ser Gly Cys Glu
300                 305                 310
Arg Lys
315

<210> SEQ ID NO 8
<211> LENGTH: 1017
<212> TYPE: DNA
<213> ORGANISM: Mucor circinelloides CP99001
<220> FEATURE:
<221> NAME/KEY: sig_peptide
<222> LOCATION: (1)..(66)
<220> FEATURE:
<221> NAME/KEY: mat_peptide
<222> LOCATION: (67)..(1017)

<400> SEQUENCE: 8 atg aag ttc acc gtt gct att act tca atc gct gtt gca ctc gct ctc      48
Met Lys Phe Thr Val Ala Ile Thr Ser Ile Ala Val Ala Leu Ala Leu
        -20                 -15                 -10 agc tct tct gct gaa gct gct tct tgc agc tct gtc tat ggt caa tgt      96
Ser Ser Ser Ala Glu Ala Ala Ser Cys Ser Ser Val Tyr Gly Gln Cys
        -5                   1                   5              10 ggt ggc att gga tgg agt gga cct acc tgt tgt gaa agt ggc tct act     144
Gly Gly Ile Gly Trp Ser Gly Pro Thr Cys Cys Glu Ser Gly Ser Thr
                 15                  20                  25 tgc gtt gct caa gaa ggc aac aaa tac tac tct caa tgt ctt ccc gga     192
Cys Val Ala Gln Glu Gly Asn Lys Tyr Tyr Ser Gln Cys Leu Pro Gly
         30                  35                  40 tcc cac agt aac aat gct ggt aac gct agc agc acc aag aag aca tct     240
Ser His Ser Asn Asn Ala Gly Asn Ala Ser Ser Thr Lys Lys Thr Ser
     45                  50                  55 acc aag aca tct act acc acc gcc aag gct act gct act gtc acc acc     288
Thr Lys Thr Ser Thr Thr Thr Ala Lys Ala Thr Ala Thr Val Thr Thr
 60                  65                  70
```

```
aag aca gta acc aag aca act acc aag aca act acc aag act agc act      336
Lys Thr Val Thr Lys Thr Thr Thr Lys Thr Thr Thr Lys Thr Ser Thr
 75              80                  85                  90 act gcc gct gct tct act tcc acc tct tct tct gct ggt tac aag gtc      384
Thr Ala Ala Ala Ser Thr Ser Thr Ser Ser Ser Ala Gly Tyr Lys Val
                 95                 100                 105 atc tct ggc ggt aaa tct ggc agt ggt tcc aca act cgt tat tgg gat      432
Ile Ser Gly Gly Lys Ser Gly Ser Gly Ser Thr Thr Arg Tyr Trp Asp
             110                 115                 120 tgt tgt aaa gct tct tgc agc tgg cct gga aaa gct tct gtc act ggt      480
Cys Cys Lys Ala Ser Cys Ser Trp Pro Gly Lys Ala Ser Val Thr Gly
         125                 130                 135 cct gtt gac acc tgt gcc tcc aat ggt atc tct tta tta gat gcc aat      528
Pro Val Asp Thr Cys Ala Ser Asn Gly Ile Ser Leu Leu Asp Ala Asn
     140                 145                 150 gct caa agt ggt tgt aac ggt ggt aat ggt ttc atg tgt aac aac aac      576
Ala Gln Ser Gly Cys Asn Gly Gly Asn Gly Phe Met Cys Asn Asn Asn
155                 160                 165                 170 caa cct tgg gct gtc aat gat gag ctc gct tac ggt ttc gct gct gcc      624
Gln Pro Trp Ala Val Asn Asp Glu Leu Ala Tyr Gly Phe Ala Ala Ala
                 175                 180                 185 tct att gct ggc tcc aac gaa gct gga tgg tgt tgt ggc tgt tat gaa      672
Ser Ile Ala Gly Ser Asn Glu Ala Gly Trp Cys Cys Gly Cys Tyr Glu
             190                 195                 200 ttg acc ttc act tct ggc gct gct tct gga aag aag atg gtt gtt caa      720
Leu Thr Phe Thr Ser Gly Ala Ala Ser Gly Lys Lys Met Val Val Gln
         205                 210                 215 gtt acc aac acc ggt ggc gat tta ggc tct aac cac ttt gat ttg caa      768
Val Thr Asn Thr Gly Gly Asp Leu Gly Ser Asn His Phe Asp Leu Gln
     220                 225                 230 atg ccc ggt ggt ggc gtt ggt atc ttc aat ggc tgt gct gct caa tgg      816
Met Pro Gly Gly Gly Val Gly Ile Phe Asn Gly Cys Ala Ala Gln Trp
235                 240                 245                 250 ggc gct ccc aat gat ggc tgg gga gct aga tat ggt ggt gtc agc tct      864
Gly Ala Pro Asn Asp Gly Trp Gly Ala Arg Tyr Gly Gly Val Ser Ser
                 255                 260                 265 gtc tct gac tgt gcc tct ctt ccc tct gct ctt caa gct ggt tgt aaa      912
Val Ser Asp Cys Ala Ser Leu Pro Ser Ala Leu Gln Ala Gly Cys Lys
             270                 275                 280 tgg aga ttc aac tgg ttc aag aac tct gat aac cct acc atg acc ttc      960
Trp Arg Phe Asn Trp Phe Lys Asn Ser Asp Asn Pro Thr Met Thr Phe
         285                 290                 295 aag gaa gtt acc tgt cct gct gaa tta act act cgc tca ggt tgc gaa     1008
Lys Glu Val Thr Cys Pro Ala Glu Leu Thr Thr Arg Ser Gly Cys Glu
     300                 305                 310 aga aag taa                                                         1017
Arg Lys
315
```

<210> SEQ ID NO 9
<211> LENGTH: 387
<212> TYPE: PRT
<213> ORGANISM: Mucor circinelloides CP99001
<220> FEATURE:
<221> NAME/KEY: sig_peptide
<222> LOCATION: (-22)..(-1)
<220> FEATURE:
<221> NAME/KEY: mat_peptide
<222> LOCATION: (1)..(365)

<400> SEQUENCE: 9

Met Lys Phe Thr Val Ala Ile Thr Ser Ile Ala Val Ala Leu Ala Leu

-continued

```
                -20              -15              -10
Ser Ser Ser Ala Glu Ala Ala Ser Cys Ser Ser Val Tyr Gly Gln Cys
         -5                   1               5                  10

Gly Gly Ile Gly Trp Thr Gly Pro Thr Cys Cys Asp Ala Gly Ser Thr
             15                  20                  25

Cys Lys Ala Gln Lys Asp Asn Lys Tyr Tyr Ser Gln Cys Ile Pro Lys
         30                  35                  40

Pro Lys Gly Ser Ser Ser Ser Ser Cys Ser Ser Val Tyr Ser Gln
         45                  50                  55

Cys Gly Gly Ile Gly Trp Ser Gly Pro Thr Cys Cys Glu Ser Gly Ser
     60                  65                  70

Thr Cys Val Ala Gln Glu Gly Asn Lys Tyr Tyr Ser Gln Cys Leu Pro
 75                  80                  85                  90

Gly Ser His Ser Asn Asn Ala Gly Asn Ala Ser Ser Thr Lys Lys Thr
                 95                 100                 105

Ser Thr Lys Thr Ser Thr Thr Thr Ala Lys Ala Thr Ala Thr Val Thr
             110                 115                 120

Thr Lys Thr Val Thr Lys Thr Thr Thr Lys Thr Thr Thr Lys Thr Ser
         125                 130                 135

Thr Thr Ala Ala Ala Ser Thr Ser Thr Ser Ser Ala Gly Tyr Lys
 140                 145                 150

Val Ile Ser Gly Gly Lys Ser Gly Ser Gly Ser Thr Thr Arg Tyr Trp
155                 160                 165                 170

Asp Cys Cys Lys Ala Ser Cys Ser Trp Pro Gly Lys Ala Ser Val Thr
                 175                 180                 185

Gly Pro Val Asp Thr Cys Ala Ser Asn Gly Ile Ser Leu Leu Asp Ala
             190                 195                 200

Asn Ala Gln Ser Gly Cys Asn Gly Gly Asn Gly Phe Met Cys Asn Asn
         205                 210                 215

Asn Gln Pro Trp Ala Val Asn Asp Glu Leu Ala Tyr Gly Phe Ala Ala
         220                 225                 230

Ala Ser Ile Ala Gly Ser Asn Glu Ala Gly Trp Cys Cys Gly Cys Tyr
235                 240                 245                 250

Glu Leu Thr Phe Thr Ser Gly Ala Ala Ser Gly Lys Lys Met Val Val
                 255                 260                 265

Gln Val Thr Asn Thr Gly Gly Asp Leu Gly Ser Asn His Phe Asp Leu
             270                 275                 280

Gln Met Pro Gly Gly Gly Val Gly Ile Phe Asn Gly Cys Ala Ala Gln
         285                 290                 295

Trp Gly Ala Pro Asn Asp Gly Trp Gly Ala Arg Tyr Gly Gly Val Ser
     300                 305                 310

Ser Val Ser Asp Cys Ala Ser Leu Pro Ser Ala Leu Gln Ala Gly Cys
315                 320                 325                 330

Lys Trp Arg Phe Asn Trp Phe Lys Asn Ser Asp Asn Pro Thr Met Thr
                 335                 340                 345

Phe Lys Glu Val Thr Cys Pro Ala Glu Leu Thr Thr Arg Ser Gly Cys
             350                 355                 360

Glu Arg Lys
         365

<210> SEQ ID NO 10
<211> LENGTH: 1164
<212> TYPE: DNA
<213> ORGANISM: Mucor circinelloides CP99001
```

-continued

```
<220> FEATURE:
<221> NAME/KEY: sig_peptide
<222> LOCATION: (1)..(66)
<220> FEATURE:
<221> NAME/KEY: mat_peptide
<222> LOCATION: (67)..(1164)

<400> SEQUENCE: 10 atg aag ttc acc gtt gct att act tca atc gct gtt gca ctc gct ctc      48
Met Lys Phe Thr Val Ala Ile Thr Ser Ile Ala Val Ala Leu Ala Leu
        -20             -15                 -10 agc tct tct gct gaa gct gct tct tgc agc tct gtc tat ggt caa tgt      96
Ser Ser Ser Ala Glu Ala Ala Ser Cys Ser Ser Val Tyr Gly Gln Cys
    -5               1               5                    10 ggt ggc att ggc tgg act ggt cct aca tgt tgt gat gct gga tcg acc     144
Gly Gly Ile Gly Trp Thr Gly Pro Thr Cys Cys Asp Ala Gly Ser Thr
            15              20                  25 tgt aaa gct caa aag gat aac aaa tat tat tct caa tgt att ccc aaa     192
Cys Lys Ala Gln Lys Asp Asn Lys Tyr Tyr Ser Gln Cys Ile Pro Lys
        30                  35                  40 ccc aag ggt tcc tcc tca tca tca tgt agt tcc gtc tat agt caa        240
Pro Lys Gly Ser Ser Ser Ser Ser Cys Ser Ser Val Tyr Ser Gln
            45                  50                  55 tgc ggt ggc att gga tgg agt gga cct acc tgt tgt gaa agt ggc tct     288
Cys Gly Gly Ile Gly Trp Ser Gly Pro Thr Cys Cys Glu Ser Gly Ser
        60                  65                  70 act tgc gtt gct caa gaa ggc aac aaa tac tac tct caa tgt ctt ccc     336
Thr Cys Val Ala Gln Glu Gly Asn Lys Tyr Tyr Ser Gln Cys Leu Pro
 75                  80                  85                  90 gga tcc cac agt aac aat gct ggt aac gct agc agc acc aag aag aca     384
Gly Ser His Ser Asn Asn Ala Gly Asn Ala Ser Ser Thr Lys Lys Thr
                95                  100                 105 tct acc aag aca tct act acc acc gcc aag gct act gct act gtc acc     432
Ser Thr Lys Thr Ser Thr Thr Thr Ala Lys Ala Thr Ala Thr Val Thr
            110                 115                 120 acc aag aca gta acc aag aca act acc aag aca act acc aag act agc     480
Thr Lys Thr Val Thr Lys Thr Thr Thr Lys Thr Thr Thr Lys Thr Ser
        125                 130                 135 act act gcc gct gct tct act tcc acc tct tct tct gct ggt tac aag     528
Thr Thr Ala Ala Ala Ser Thr Ser Thr Ser Ser Ser Ala Gly Tyr Lys
    140                 145                 150 gtc atc tct ggc ggt aaa tct ggc agt ggt tcc aca act cgt tat tgg     576
Val Ile Ser Gly Gly Lys Ser Gly Ser Gly Ser Thr Thr Arg Tyr Trp
155                 160                 165                 170 gat tgt tgt aaa gct tct tgc agc tgg cct gga aaa gct tct gtc act     624
Asp Cys Cys Lys Ala Ser Cys Ser Trp Pro Gly Lys Ala Ser Val Thr
                175                 180                 185 ggt cct gtt gac acc tgt gcc tcc aat ggt atc tct tta tta gat gcc     672
Gly Pro Val Asp Thr Cys Ala Ser Asn Gly Ile Ser Leu Leu Asp Ala
            190                 195                 200 aat gct caa agt ggt tgt aac ggt ggt aat ggt ttc atg tgt aac aac     720
Asn Ala Gln Ser Gly Cys Asn Gly Gly Asn Gly Phe Met Cys Asn Asn
        205                 210                 215 aac caa cct tgg gct gtc aat gat gag ctc gct tac ggt ttc gct gct     768
Asn Gln Pro Trp Ala Val Asn Asp Glu Leu Ala Tyr Gly Phe Ala Ala
    220                 225                 230 gcc tct att gct ggc tcc aac gaa gct gga tgg tgt tgt gct tgt tat     816
Ala Ser Ile Ala Gly Ser Asn Glu Ala Gly Trp Cys Cys Gly Cys Tyr
235                 240                 245                 250 gaa ttg acc ttc act tct ggc gct gct tct gga aag aag atg gtt gtt     864
Glu Leu Thr Phe Thr Ser Gly Ala Ala Ser Gly Lys Lys Met Val Val
```

-continued

```
                       255                 260                 265
caa gtt acc aac acc ggt ggc gat tta ggc tct aac cac ttt gat ttg        912
Gln Val Thr Asn Thr Gly Gly Asp Leu Gly Ser Asn His Phe Asp Leu
                270                 275                 280 caa atg ccc ggt ggt ggc gtt ggt atc ttc aat ggc tgt gct gct caa        960
Gln Met Pro Gly Gly Gly Val Gly Ile Phe Asn Gly Cys Ala Ala Gln
            285                 290                 295 tgg ggc gct ccc aat gat ggc tgg gga gct aga tat ggt ggt gtc agc       1008
Trp Gly Ala Pro Asn Asp Gly Trp Gly Ala Arg Tyr Gly Gly Val Ser
        300                 305                 310 tct gtc tct gac tgt gcc tct ctt ccc tct gct ctt caa gct ggt tgt       1056
Ser Val Ser Asp Cys Ala Ser Leu Pro Ser Ala Leu Gln Ala Gly Cys
    315                 320                 325                 330 aaa tgg aga ttc aac tgg ttc aag aac tct gat aac cct acc atg acc       1104
Lys Trp Arg Phe Asn Trp Phe Lys Asn Ser Asp Asn Pro Thr Met Thr
                335                 340                 345 ttc aag gaa gtt acc tgt cct gct gaa tta act act cgc tca ggt tgc       1152
Phe Lys Glu Val Thr Cys Pro Ala Glu Leu Thr Thr Arg Ser Gly Cys
            350                 355                 360 gaa aga aag taa                                                        1164
Glu Arg Lys
        365

<210> SEQ ID NO 11
<211> LENGTH: 346
<212> TYPE: PRT
<213> ORGANISM: Phycomyces nitens CP99002
<220> FEATURE:
<221> NAME/KEY: sig_peptide
<222> LOCATION: (-19)..(-1)
<220> FEATURE:
<221> NAME/KEY: mat_peptide
<222> LOCATION: (1)..(327)

<400> SEQUENCE: 11

Met Lys Phe Ser Ile Ile Ala Ser Ala Leu Leu Ala Ala Ser Ser
                -15                 -10                 -5

Thr Tyr Ala Ala Glu Cys Ser Gln Gly Tyr Gly Gln Cys Gly Gly Lys
            1               5                   10

Met Trp Thr Gly Pro Thr Cys Cys Thr Ser Gly Phe Thr Cys Val Gly
        15                  20                  25

Ala Glu Asn Asn Glu Trp Tyr Ser Gln Cys Ile Pro Asn Asp Gln Val
    30                  35                  40                  45

Gln Gly Asn Pro Lys Thr Thr Thr Thr Thr Thr Lys Ala Ala Thr
                50                  55                  60

Thr Thr Lys Ala Pro Val Thr Thr Thr Lys Ala Thr Thr Thr Thr
            65                  70                  75

Thr Lys Ala Pro Val Thr Thr Thr Lys Ala Thr Thr Thr Thr Thr
        80                  85                  90

Lys Thr Thr Lys Thr Thr Thr Lys Ala Ala Thr Thr Thr Ser
    95                  100                 105

Ser Ser Asn Thr Gly Tyr Ser Pro Ile Ser Gly Gly Phe Ser Gly Asn
110                 115                 120                 125

Gly Arg Thr Thr Arg Tyr Trp Asp Cys Cys Lys Pro Ser Cys Ala Trp
                130                 135                 140

Asp Gly Lys Ala Ser Val Thr Lys Pro Val Leu Thr Cys Ala Lys Asp
            145                 150                 155

Gly Val Ser Arg Leu Gly Ser Asp Val Gln Ser Gly Cys Val Gly Gly
        160                 165                 170
```

```
Gln Ala Tyr Met Cys Asn Asp Asn Gln Pro Trp Val Val Asn Asp Asp
    175                 180                 185

Leu Ala Tyr Gly Phe Ala Ala Ser Leu Gly Ser Ala Gly Ala Ser
190                 195                 200                 205

Ala Phe Cys Cys Gly Cys Tyr Glu Leu Thr Phe Thr Asn Thr Ala Val
                210                 215                 220

Ala Gly Lys Lys Phe Val Val Gln Val Thr Asn Thr Gly Asp Asp Leu
            225                 230                 235

Ser Thr Asn His Phe Asp Leu Gln Met Pro Gly Gly Val Gly Tyr
        240                 245                 250

Phe Asn Gly Cys Gln Ser Gln Trp Asn Thr Asn Thr Asp Gly Trp Gly
    255                 260                 265

Ala Arg Tyr Gly Gly Ile Ser Ser Ile Ser Glu Cys Asp Lys Leu Pro
270                 275                 280                 285

Thr Gln Leu Gln Ala Gly Cys Lys Trp Arg Phe Gly Trp Phe Lys Asn
                290                 295                 300

Ala Asp Asn Pro Glu Val Thr Phe Lys Ala Val Thr Cys Pro Ala Glu
            305                 310                 315

Ile Ile Ala Lys Thr Gly Cys Glu Arg Lys
320                 325

<210> SEQ ID NO 12
<211> LENGTH: 1041
<212> TYPE: DNA
<213> ORGANISM: Phycomyces nitens CP99002
<220> FEATURE:
<221> NAME/KEY: sig_peptide
<222> LOCATION: (1)..(57)
<220> FEATURE:
<221> NAME/KEY: mat_peptide
<222> LOCATION: (58)..(1041)

<400> SEQUENCE: 12 atg aag ttc tcc atc atc gct tcc gcc ctt ctc ctc gct gcc agc tcc      48
Met Lys Phe Ser Ile Ile Ala Ser Ala Leu Leu Leu Ala Ala Ser Ser
                -15                 -10                 -5 act tac gct gct gaa tgc agc caa ggc tat ggc cag tgt ggt ggc aag      96
Thr Tyr Ala Ala Glu Cys Ser Gln Gly Tyr Gly Gln Cys Gly Gly Lys
                1               5                   10 atg tgg act ggt ccc acc tgc tgc acc tcc ggc ttc acc tgt gta ggt     144
Met Trp Thr Gly Pro Thr Cys Cys Thr Ser Gly Phe Thr Cys Val Gly
        15                  20                  25 gcc gaa aac aac gag tgg tac tct cag tgt atc ccc aac gat caa gtc     192
Ala Glu Asn Asn Glu Trp Tyr Ser Gln Cys Ile Pro Asn Asp Gln Val
30                  35                  40                  45 cag ggt aac ccc aag acc acc acc acc acc acc aag gct gcc act         240
Gln Gly Asn Pro Lys Thr Thr Thr Thr Thr Thr Lys Ala Ala Thr
                50                  55                  60 acc acc aag gct cct gtc acc acc acc aag gcc acc acc acc acc         288
Thr Thr Lys Ala Pro Val Thr Thr Thr Lys Ala Thr Thr Thr Thr
            65                  70                  75 acc aag gcc cct gtc acc acc acc aag gcc act act act acc acc acc     336
Thr Lys Ala Pro Val Thr Thr Thr Lys Ala Thr Thr Thr Thr Thr Thr
        80                  85                  90 aag acc acc acc aag acc acc acc acc aag gct gcc acc acc acc tcc     384
Lys Thr Thr Thr Lys Thr Thr Thr Thr Lys Ala Ala Thr Thr Thr Ser
    95                  100                 105 tct tcc aac act ggc tac agc ccc att tct ggt ggc ttc tct gga aac     432
Ser Ser Asn Thr Gly Tyr Ser Pro Ile Ser Gly Gly Phe Ser Gly Asn
```

```
                 110                 115                 120                 125
ggt cgc act acc cgc tac tgg gat tgc tgc aag ccc tct tgc gcc tgg       480
Gly Arg Thr Thr Arg Tyr Trp Asp Cys Cys Lys Pro Ser Cys Ala Trp
                 130                 135                 140 gac gga aag gct tct gta act aag cct gta ctc acc tgt gcc aag gat       528
Asp Gly Lys Ala Ser Val Thr Lys Pro Val Leu Thr Cys Ala Lys Asp
             145                 150                 155 ggt gtc agc cgt ctc ggt tcc gat gtc cag agc ggt tgc gtc ggc ggc       576
Gly Val Ser Arg Leu Gly Ser Asp Val Gln Ser Gly Cys Val Gly Gly
         160                 165                 170 cag gcc tac atg tgc aat gac aac cag ccc tgg gtt gtc aat gac gac       624
Gln Ala Tyr Met Cys Asn Asp Asn Gln Pro Trp Val Val Asn Asp Asp
     175                 180                 185 ctt gcc tac ggt ttc gct gct gcc agt ctc ggt agc gcc ggt gcc tct       672
Leu Ala Tyr Gly Phe Ala Ala Ala Ser Leu Gly Ser Ala Gly Ala Ser
190                 195                 200                 205 gca ttc tgc tgc ggc tgt tac gag ctt acc ttc acc aac act gct gtc       720
Ala Phe Cys Cys Gly Cys Tyr Glu Leu Thr Phe Thr Asn Thr Ala Val
                 210                 215                 220 gct ggc aag aag ttt gtc gtc cag gtc acc aac acc ggt gat gat ctc       768
Ala Gly Lys Lys Phe Val Val Gln Val Thr Asn Thr Gly Asp Asp Leu
                 225                 230                 235 agc acc aac cac ttt gat ttg cag atg ccc ggc ggt ggt gtc ggc tac       816
Ser Thr Asn His Phe Asp Leu Gln Met Pro Gly Gly Gly Val Gly Tyr
                 240                 245                 250 ttc aac ggc tgc cag tcc cag tgg aac acc aac acc gat ggc tgg ggt       864
Phe Asn Gly Cys Gln Ser Gln Trp Asn Thr Asn Thr Asp Gly Trp Gly
             255                 260                 265 gct cgc tat ggc ggt att agc tct att tca gag tgc gac aag ctt cct       912
Ala Arg Tyr Gly Gly Ile Ser Ser Ile Ser Glu Cys Asp Lys Leu Pro
270                 275                 280                 285 acc cag ttg cag gct ggt tgc aag tgg aga ttc gga tgg ttc aag aac       960
Thr Gln Leu Gln Ala Gly Cys Lys Trp Arg Phe Gly Trp Phe Lys Asn
                 290                 295                 300 gct gac aac cca gag gtc acc ttc aag gct gtt act tgc cct gcc gag      1008
Ala Asp Asn Pro Glu Val Thr Phe Lys Ala Val Thr Cys Pro Ala Glu
             305                 310                 315 atc att gcc aag act ggt tgc gag cgc aag taa                          1041
Ile Ile Ala Lys Thr Gly Cys Glu Arg Lys
         320                 325

<210> SEQ ID NO 13
<211> LENGTH: 1043
<212> TYPE: DNA
<213> ORGANISM: Artificial Sequence
<220> FEATURE:
<221> NAME/KEY: sig_peptide
<222> LOCATION: (16)..(84)
<220> FEATURE:
<221> NAME/KEY: mat_peptide
<222> LOCATION: (84)..(1043)
<223> OTHER INFORMATION: Codon-optimized sequence corresponding to RCE I
      protein (SEQ. ID NO:2)

<400> SEQUENCE: 13
ggatcctggg acaag atg aag ttc atc act atc gcc tcc tcc gcc ctc ctt      51
            Met Lys Phe Ile Thr Ile Ala Ser Ser Ala Leu Leu
                            -20                 -15 gcc ctc gcc ctt ggc act gag atg gcc tcc gcc gct gag tgc tcc aag       99
Ala Leu Ala Leu Gly Thr Glu Met Ala Ser Ala Ala Glu Cys Ser Lys
    -10                  -5                  1               5 ctc tac gga cag tgc ggc gga aag aac tgg aac ggc ccc acc tgc tgc      147
```

-continued

```
              Leu Tyr Gly Gln Cys Gly Gly Lys Asn Trp Asn Gly Pro Thr Cys Cys
                               10                  15                  20 gag agc ggc tcg acc tgc aag gtc tcg aat gac tac tac agc cag tgc            195
Glu Ser Gly Ser Thr Cys Lys Val Ser Asn Asp Tyr Tyr Ser Gln Cys
                25                  30                  35 ctg ccg agc ggc tcc tcg gga aac aag tcg agc gag tcg gcc cac aag            243
Leu Pro Ser Gly Ser Ser Gly Asn Lys Ser Ser Glu Ser Ala His Lys
            40                  45                  50 aag acc acg acc gct gcc cac aag aag acc acg acc gcc gct cac aag            291
Lys Thr Thr Thr Ala Ala His Lys Lys Thr Thr Thr Ala Ala His Lys
        55                  60                  65 aag act acg acc gct ccc gcc aag aag acc acg acc gtc gcc aag gct            339
Lys Thr Thr Thr Ala Pro Ala Lys Lys Thr Thr Thr Val Ala Lys Ala
    70                  75                  80                  85 tcg act ccg tcc aac tcg agc agc tcg tct tcg gga aag tac agc gct            387
Ser Thr Pro Ser Asn Ser Ser Ser Ser Ser Gly Lys Tyr Ser Ala
                90                  95                 100 gtc agc ggt ggc gct agc ggc aac ggc gtc act acc cgc tac tgg gac            435
Val Ser Gly Gly Ala Ser Gly Asn Gly Val Thr Thr Arg Tyr Trp Asp
            105                 110                 115 tgc tgc aag gct tcg tgc tcg tgg ccc ggc aag gct aac gtc agc tcg            483
Cys Cys Lys Ala Ser Cys Ser Trp Pro Gly Lys Ala Asn Val Ser Ser
        120                 125                 130 cct gtc aag tcc tgc aac aag gac ggc gtc acc gct ctt agc gac tcc            531
Pro Val Lys Ser Cys Asn Lys Asp Gly Val Thr Ala Leu Ser Asp Ser
    135                 140                 145 aac gcc cag tcc ggc tgc aac ggc ggc aac tcc tac atg tgc aac gac            579
Asn Ala Gln Ser Gly Cys Asn Gly Gly Asn Ser Tyr Met Cys Asn Asp
150                 155                 160                 165 aac cag cca tgg gct gtc aac gac aac ctt gct tac ggt ttc gct gcc            627
Asn Gln Pro Trp Ala Val Asn Asp Asn Leu Ala Tyr Gly Phe Ala Ala
                170                 175                 180 gct gcc att agc ggc ggt ggc gag agc cgc tgg tgc tgc tcc tgc ttc            675
Ala Ala Ile Ser Gly Gly Gly Glu Ser Arg Trp Cys Cys Ser Cys Phe
            185                 190                 195 gag ctc acc ttc acc tcc acc agc gtt gct ggc aag aag atg gtc gtc            723
Glu Leu Thr Phe Thr Ser Thr Ser Val Ala Gly Lys Lys Met Val Val
        200                 205                 210 cag gtc acc aac act ggc ggt gac ctt ggc agc tcg acc ggt gcc cac            771
Gln Val Thr Asn Thr Gly Gly Asp Leu Gly Ser Ser Thr Gly Ala His
    215                 220                 225 ttc gat ctc cag atg ccc ggc ggc ggc gtc ggc atc ttc aac gga tgc            819
Phe Asp Leu Gln Met Pro Gly Gly Gly Val Gly Ile Phe Asn Gly Cys
230                 235                 240                 245 tcg tcc cag tgg ggc gct ccc aac gac ggc tgg ggc tcg cgc tac ggc            867
Ser Ser Gln Trp Gly Ala Pro Asn Asp Gly Trp Gly Ser Arg Tyr Gly
                250                 255                 260 ggc atc agc tcc gcc agc gac tgc tcg tcc ctc ccc agc gcc ctc cag            915
Gly Ile Ser Ser Ala Ser Asp Cys Ser Ser Leu Pro Ser Ala Leu Gln
            265                 270                 275 gcc ggc tgc aag tgg cgc ttc aac tgg ttc aag aac gcc gac aac ccg            963
Ala Gly Cys Lys Trp Arg Phe Asn Trp Phe Lys Asn Ala Asp Asn Pro
        280                 285                 290 tcc atg acc tac aag gag gtc acc tgc ccc aag gag atc acc gct aag           1011
Ser Met Thr Tyr Lys Glu Val Thr Cys Pro Lys Glu Ile Thr Ala Lys
    295                 300                 305 acc gga tgc tcg cgc aag taaacgcagg atcc                                    1043
Thr Gly Cys Ser Arg Lys
310                 315
```

<210> SEQ ID NO 14
<211> LENGTH: 40
<212> TYPE: PRT
<213> ORGANISM: Rhizopus oryzae CP96001

<400> SEQUENCE: 14

Ala Glu Cys Ser Lys Leu Tyr Gly Gln Cys Gly Gly Lys Asn Trp Asn
 1               5                  10                  15

Gly Pro Thr Cys Cys Glu Ser Gly Ser Thr Cys Lys Val Ser Asn Asp
            20                  25                  30

Tyr Tyr Ser Gln Cys Leu Pro Ser
        35                  40

<210> SEQ ID NO 15
<211> LENGTH: 22
<212> TYPE: PRT
<213> ORGANISM: Mucor circinelloides CP99001

<400> SEQUENCE: 15

Ala Ser Cys Ser Ser Val Tyr Gly Gln Cys Gly Gly Ile Gly Trp Ser
 1               5                  10                  15

Gly Pro Thr Cys Cys Glu
            20

<210> SEQ ID NO 16
<211> LENGTH: 23
<212> TYPE: PRT
<213> ORGANISM: Phycomyces nitens CP99002

<400> SEQUENCE: 16

Ala Glu Cys Ser Gln Gly Tyr Gly Gln Cys Gly Gly Lys Met Trp Thr
 1               5                  10                  15

Gly Pro Thr Cys Cys Thr Ser
            20

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence:consensus
      sequence
<220> FEATURE:
<221> NAME/KEY: MISC_FEATURE
<222> LOCATION: (1)..(6)
<223> OTHER INFORMATION: any amino acid
<220> FEATURE:
<221> NAME/KEY: MISC_FEATURE
<222> LOCATION: (11)..(14)
<223> OTHER INFORMATION: any amino acid
<220> FEATURE:
<221> NAME/KEY: MISC_FEATURE
<222> LOCATION: (16)..(18)
<223> OTHER INFORMATION: any amino acid
<220> FEATURE:
<221> NAME/KEY: MISC_FEATURE
<222> LOCATION: (20)..(24)
<223> OTHER INFORMATION: any amino acid or empty
<220> FEATURE:
<221> NAME/KEY: MISC_FEATURE
<222> LOCATION: (25)
<223> OTHER INFORMATION: any amino acid
<220> FEATURE:
<221> NAME/KEY: MISC_FEATURE
<222> LOCATION: (27)..(29)
<223> OTHER INFORMATION: any amino acid
<220> FEATURE:
<221> NAME/KEY: MISC_FEATURE

```
<222> LOCATION: (30)..(31)
<223> OTHER INFORMATION: any amino acid or empty
<220> FEATURE:
<221> NAME/KEY: MISC_FEATURE
<222> LOCATION: (33)..(34)
<223> OTHER INFORMATION: any amino acid
<220> FEATURE:
<221> NAME/KEY: MISC_FEATURE
<222> LOCATION: (36)
<223> OTHER INFORMATION: any amino acid
<220> FEATURE:
<221> NAME/KEY: MISC_FEATURE
<222> LOCATION: (39)
<223> OTHER INFORMATION: any amino acid

<400> SEQUENCE: 17

Xaa Xaa Xaa Xaa Xaa Xaa Gln Cys Gly Gly Xaa Xaa Xaa Xaa Gly Xaa
 1               5                  10                  15

Xaa Xaa Cys Xaa Xaa Xaa Xaa Xaa Xaa Cys Xaa Xaa Xaa Xaa Xaa Asn
             20                  25                  30

Xaa Xaa Tyr Xaa Gln Cys Xaa
         35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence:consensus
      sequence (CBD)
<220> FEATURE:
<221> NAME/KEY: MISC_FEATURE
<222> LOCATION: (1)..(6)
<223> OTHER INFORMATION: any amino acid
<220> FEATURE:
<221> NAME/KEY: MISC_FEATURE
<222> LOCATION: (11)..(14)
<223> OTHER INFORMATION: any amino acid
<220> FEATURE:
<221> NAME/KEY: MISC_FEATURE
<222> LOCATION: (16)..(18)
<223> OTHER INFORMATION: any amino acid
<220> FEATURE:
<221> NAME/KEY: MISC_FEATURE
<222> LOCATION: (20)..(24)
<223> OTHER INFORMATION: any amino acid or empty
<220> FEATURE:
<221> NAME/KEY: MISC_FEATURE
<222> LOCATION: (25)
<223> OTHER INFORMATION: any amino acid
<220> FEATURE:
<221> NAME/KEY: MISC_FEATURE
<222> LOCATION: (27)..(29)
<223> OTHER INFORMATION: any amino acid
<220> FEATURE:
<221> NAME/KEY: MISC_FEATURE
<222> LOCATION: (30)..(31)
<223> OTHER INFORMATION: any amino acid or empty
<220> FEATURE:
<221> NAME/KEY: MISC_FEATURE
<222> LOCATION: (33)..(34)
<223> OTHER INFORMATION: any amino acid
<220> FEATURE:
<221> NAME/KEY: MISC_FEATURE
<222> LOCATION: (36)
<223> OTHER INFORMATION: any amino acid
<220> FEATURE:
<221> NAME/KEY: MISC_FEATURE
<222> LOCATION: (39)
<223> OTHER INFORMATION: any amino acid

<400> SEQUENCE: 18

Xaa Xaa Xaa Xaa Xaa Xaa Gln Cys Gly Gly Xaa Xaa Xaa Xaa Gly Xaa
 1               5                  10                  15
```

```
Xaa Xaa Cys Xaa Xaa Xaa Xaa Xaa Xaa Cys Xaa Xaa Xaa Xaa Xaa Asn
            20                  25                  30

Xaa Xaa Tyr Xaa Gln Cys Xaa
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence:consensus
      sequence (CBD)
<220> FEATURE:
<221> NAME/KEY: MISC_FEATURE
<222> LOCATION: (3)..(4)
<223> OTHER INFORMATION: any amino acid
<220> FEATURE:
<221> NAME/KEY: MISC_FEATURE
<222> LOCATION: (6)
<223> OTHER INFORMATION: any amino acid
<220> FEATURE:
<221> NAME/KEY: MISC_FEATURE
<222> LOCATION: (11)..(12)
<223> OTHER INFORMATION: any amino acid
<220> FEATURE:
<221> NAME/KEY: MISC_FEATURE
<222> LOCATION: (14)
<223> OTHER INFORMATION: any amino acid
<220> FEATURE:
<221> NAME/KEY: MISC_FEATURE
<222> LOCATION: (20)..(21)
<223> OTHER INFORMATION: any amino acid or empty
<220> FEATURE:
<221> NAME/KEY: MISC_FEATURE
<222> LOCATION: (23)
<223> OTHER INFORMATION: any amino acid or empty
<220> FEATURE:
<221> NAME/KEY: MISC_FEATURE
<222> LOCATION: (26)..(28)
<223> OTHER INFORMATION: any amino acid
<220> FEATURE:
<221> NAME/KEY: MISC_FEATURE
<222> LOCATION: (29)..(30)
<223> OTHER INFORMATION: any amino acid or empty
<220> FEATURE:
<221> NAME/KEY: MISC_FEATURE
<222> LOCATION: (32)..(33)
<223> OTHER INFORMATION: any amino acid
<220> FEATURE:
<221> NAME/KEY: MISC_FEATURE
<222> LOCATION: (38)
<223> OTHER INFORMATION: any amino acid

<400> SEQUENCE: 19

Cys Ser Xaa Xaa Tyr Xaa Gln Cys Gly Gly Xaa Xaa Trp Xaa Gly Pro
  1               5                  10                  15

Thr Cys Cys Xaa Xaa Gly Xaa Thr Cys Xaa Xaa Xaa Xaa Asn Xaa
            20                  25                  30

Xaa Tyr Ser Gln Cys Xaa
        35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence:consensus
      sequence (CBD)
<220> FEATURE:
<221> NAME/KEY: MISC_FEATURE
<222> LOCATION: (3)
<223> OTHER INFORMATION: Lys, Ser or Gln
```

```
<220> FEATURE:
<221> NAME/KEY: MISC_FEATURE
<222> LOCATION: (4)
<223> OTHER INFORMATION: Leu, Ala, Val or Gly
<220> FEATURE:
<221> NAME/KEY: MISC_FEATURE
<222> LOCATION: (6)
<223> OTHER INFORMATION: Gly, Tyr or Ser
<220> FEATURE:
<221> NAME/KEY: MISC_FEATURE
<222> LOCATION: (11)
<223> OTHER INFORMATION: Lys or Ile
<220> FEATURE:
<221> NAME/KEY: MISC_FEATURE
<222> LOCATION: (12)
<223> OTHER INFORMATION: Asn, Asp, Gly or Met
<220> FEATURE:
<221> NAME/KEY: MISC_FEATURE
<222> LOCATION: (14)
<223> OTHER INFORMATION: Asn, Asp, Ser or Thr
<220> FEATURE:
<221> NAME/KEY: MISC_FEATURE
<222> LOCATION: (20)
<223> OTHER INFORMATION: Glu, Asp or Thr
<220> FEATURE:
<221> NAME/KEY: MISC_FEATURE
<222> LOCATION: (21)
<223> OTHER INFORMATION: Ser or Ala
<220> FEATURE:
<221> NAME/KEY: MISC_FEATURE
<222> LOCATION: (23)
<223> OTHER INFORMATION: Ser or Phe
<220> FEATURE:
<221> NAME/KEY: MISC_FEATURE
<222> LOCATION: (26)
<223> OTHER INFORMATION: Lys or Val
<220> FEATURE:
<221> NAME/KEY: MISC_FEATURE
<222> LOCATION: (27)
<223> OTHER INFORMATION: Val, Asp, Ala or Gly
<220> FEATURE:
<221> NAME/KEY: MISC_FEATURE
<222> LOCATION: (28)
<223> OTHER INFORMATION: Ser, Tyr, Gln or Ala
<220> FEATURE:
<221> NAME/KEY: MISC_FEATURE
<222> LOCATION: (29)
<223> OTHER INFORMATION: Pro, Glu, Lys or absent
<220> FEATURE:
<221> NAME/KEY: MISC_FEATURE
<222> LOCATION: (30)
<223> OTHER INFORMATION: Asp, Gly, Asn or absent
<220> FEATURE:
<221> NAME/KEY: MISC_FEATURE
<222> LOCATION: (32)
<223> OTHER INFORMATION: Asp, Pro, Lys or Glu
<220> FEATURE:
<221> NAME/KEY: MISC_FEATURE
<222> LOCATION: (33)
<223> OTHER INFORMATION: Tyr, Phe or Trp
<220> FEATURE:
<221> NAME/KEY: MISC_FEATURE
<222> LOCATION: (38)
<223> OTHER INFORMATION: Leu, Val or Ile

<400> SEQUENCE: 20

Cys Ser Xaa Xaa Tyr Xaa Gln Cys Gly Gly Xaa Xaa Trp Xaa Gly Pro
 1               5                  10                  15

Thr Cys Cys Xaa Xaa Gly Xaa Thr Cys Xaa Xaa Xaa Xaa Xaa Asn Xaa
                20                  25                  30

Xaa Tyr Ser Gln Cys Xaa
            35

<210> SEQ ID NO 21
<211> LENGTH: 38
```

```
<212> TYPE: PRT
<213> ORGANISM: Artificial Sequence
<220> FEATURE:
<223> OTHER INFORMATION: Description of Artificial Sequence:consensus
      sequence (CBD)
<220> FEATURE:
<221> NAME/KEY: MISC_FEATURE
<222> LOCATION: (4)
<223> OTHER INFORMATION: Leu or Ala
<220> FEATURE:
<221> NAME/KEY: MISC_FEATURE
<222> LOCATION: (6)
<223> OTHER INFORMATION: Gly or Tyr
<220> FEATURE:
<221> NAME/KEY: MISC_FEATURE
<222> LOCATION: (12)
<223> OTHER INFORMATION: Asn or Asp
<220> FEATURE:
<221> NAME/KEY: MISC_FEATURE
<222> LOCATION: (14)
<223> OTHER INFORMATION: Asn or Asp
<220> FEATURE:
<221> NAME/KEY: MISC_FEATURE
<222> LOCATION: (26)
<223> OTHER INFORMATION: Lys or Val
<220> FEATURE:
<221> NAME/KEY: MISC_FEATURE
<222> LOCATION: (27)
<223> OTHER INFORMATION: Val or Asp
<220> FEATURE:
<221> NAME/KEY: MISC_FEATURE
<222> LOCATION: (28)
<223> OTHER INFORMATION: Ser or Tyr
<220> FEATURE:
<221> NAME/KEY: MISC_FEATURE
<222> LOCATION: (29)
<223> OTHER INFORMATION: Pro or absent
<220> FEATURE:
<221> NAME/KEY: MISC_FEATURE
<222> LOCATION: (30)
<223> OTHER INFORMATION: Asp or absent
<220> FEATURE:
<221> NAME/KEY: MISC_FEATURE
<222> LOCATION: (32)
<223> OTHER INFORMATION: Asp or Pro
<220> FEATURE:
<221> NAME/KEY: MISC_FEATURE
<222> LOCATION: (33)
<223> OTHER INFORMATION: Tyr or Phe
<220> FEATURE:
<221> NAME/KEY: MISC_FEATURE
<222> LOCATION: (38)
<223> OTHER INFORMATION: Leu or Val

<400> SEQUENCE: 21

Cys Ser Lys Xaa Tyr Xaa Gln Cys Gly Gly Lys Xaa Trp Xaa Gly Pro
  1               5                  10                  15

Thr Cys Cys Glu Ser Gly Ser Thr Cys Xaa Xaa Xaa Xaa Xaa Asn Xaa
                 20                  25                  30

Xaa Tyr Ser Gln Cys Xaa
             35

<210> SEQ ID NO 22
<211> LENGTH: 36
<212> TYPE: PRT
<213> ORGANISM: Rhizopus oryzae CP96001

<400> SEQUENCE: 22

Cys Ser Lys Leu Tyr Gly Gln Cys Gly Gly Lys Asn Trp Asn Gly Pro
  1               5                  10                  15

Thr Cys Cys Glu Ser Gly Ser Thr Cys Lys Val Ser Asn Asp Tyr Tyr
                 20                  25                  30
```

Ser Gln Cys Leu
        35

<210> SEQ ID NO 23
<211> LENGTH: 36
<212> TYPE: PRT
<213> ORGANISM: Rhizopus oryzae CP96001

<400> SEQUENCE: 23

Cys Ser Lys Leu Tyr Gly Gln Cys Gly Gly Lys Asp Trp Asn Gly Pro
 1               5                  10                  15

Thr Cys Cys Glu Ser Gly Ser Thr Cys Lys Val Ser Asn Asp Tyr Tyr
             20                  25                  30

Ser Gln Cys Leu
        35

<210> SEQ ID NO 24
<211> LENGTH: 38
<212> TYPE: PRT
<213> ORGANISM: Rhizopus oryzae CP96001

<400> SEQUENCE: 24

Cys Ser Lys Ala Tyr Tyr Gln Cys Gly Gly Lys Asn Trp Asp Gly Pro
 1               5                  10                  15

Thr Cys Cys Glu Ser Gly Ser Thr Cys Val Asp Tyr Pro Asp Asn Pro
             20                  25                  30

Phe Tyr Ser Gln Cys Val
        35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence:consensus
      sequence (CBD)
<220> FEATURE:
<221> NAME/KEY: MISC_FEATURE
<222> LOCATION: (6)
<223> OTHER INFORMATION: Gly or Ser
<220> FEATURE:
<221> NAME/KEY: MISC_FEATURE
<222> LOCATION: (14)
<223> OTHER INFORMATION: Ser or Thr
<220> FEATURE:
<221> NAME/KEY: MISC_FEATURE
<222> LOCATION: (20)
<223> OTHER INFORMATION: Glu or Asp
<220> FEATURE:
<221> NAME/KEY: MISC_FEATURE
<222> LOCATION: (21)
<223> OTHER INFORMATION: Ser or Ala
<220> FEATURE:
<221> NAME/KEY: MISC_FEATURE
<222> LOCATION: (26)
<223> OTHER INFORMATION: Val or Lys
<220> FEATURE:
<221> NAME/KEY: MISC_FEATURE
<222> LOCATION: (29)
<223> OTHER INFORMATION: Glu or Lys
<220> FEATURE:
<221> NAME/KEY: MISC_FEATURE
<222> LOCATION: (30)
<223> OTHER INFORMATION: Gly or Asp
<220> FEATURE:
<221> NAME/KEY: MISC_FEATURE
<222> LOCATION: (38)
<223> OTHER INFORMATION: Leu or Ile

<400> SEQUENCE: 25

```
Cys Ser Ser Val Tyr Xaa Gln Cys Gly Ile Gly Trp Xaa Gly Pro
1               5                   10                  15

Thr Cys Cys Xaa Xaa Gly Ser Thr Cys Xaa Ala Gln Xaa Xaa Asn Lys
                20                  25                  30

Tyr Tyr Ser Gln Cys Xaa
            35
```

<210> SEQ ID NO 26
<211> LENGTH: 38
<212> TYPE: PRT
<213> ORGANISM: Mucor circinelloides CP99001

<400> SEQUENCE: 26

```
Cys Ser Ser Val Tyr Gly Gln Cys Gly Ile Gly Trp Ser Gly Pro
1               5                   10                  15

Thr Cys Cys Glu Ser Gly Ser Thr Cys Val Ala Gln Glu Gly Asn Lys
                20                  25                  30

Tyr Tyr Ser Gln Cys Leu
            35
```

<210> SEQ ID NO 27
<211> LENGTH: 38
<212> TYPE: PRT
<213> ORGANISM: Mucor circinelloides CP99001

<400> SEQUENCE: 27

```
Cys Ser Ser Val Tyr Gly Gln Cys Gly Gly Ile Gly Trp Thr Gly Pro
1               5                   10                  15

Thr Cys Cys Asp Ala Gly Ser Thr Cys Lys Ala Gln Lys Asp Asn Lys
                20                  25                  30

Tyr Tyr Ser Gln Cys Ile
            35
```

<210> SEQ ID NO 28
<211> LENGTH: 38
<212> TYPE: PRT
<213> ORGANISM: Phycomyces nitens CP99002

<400> SEQUENCE: 28

```
Cys Ser Gln Gly Tyr Gly Gln Cys Gly Gly Lys Met Trp Thr Gly Pro
1               5                   10                  15

Thr Cys Cys Thr Ser Gly Phe Thr Cys Val Gly Ala Glu Asn Asn Glu
                20                  25                  30

Trp Tyr Ser Gln Cys Ile
            35
```

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:consensus
      sequence (linker)
<220> FEATURE:
<221> NAME/KEY: MISC_FEATURE
<222> LOCATION: (1)
<223> OTHER INFORMATION: Ser, Thr or Ala
<220> FEATURE:
<221> NAME/KEY: MISC_FEATURE
<222> LOCATION: (5)
<223> OTHER INFORMATION: Trp, Tyr or Phe
<220> FEATURE:
<221> NAME/KEY: MISC_FEATURE

```
<222> LOCATION: (7)..(12)
<223> OTHER INFORMATION: any amino acid

<400> SEQUENCE: 29

Xaa Thr Arg Tyr Xaa Asp Xaa Xaa Xaa Xaa Xaa Xaa
  1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:consensus
      sequence (linker)
<220> FEATURE:
<221> NAME/KEY: MISC_FEATURE
<222> LOCATION: (2)..(4)
<223> OTHER INFORMATION: any amino acid
<220> FEATURE:
<221> NAME/KEY: MISC_FEATURE
<222> LOCATION: (8)
<223> OTHER INFORMATION: any amino acid

<400> SEQUENCE: 30

Tyr Xaa Xaa Xaa Ser Gly Gly Xaa Ser Gly
  1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:consensus
      sequence (linker)
<220> FEATURE:
<221> NAME/KEY: MISC_FEATURE
<222> LOCATION: (2)..(4)
<223> OTHER INFORMATION: any amino acid
<220> FEATURE:
<221> NAME/KEY: MISC_FEATURE
<222> LOCATION: (5)
<223> OTHER INFORMATION: Ser or Thr
<220> FEATURE:
<221> NAME/KEY: MISC_FEATURE
<222> LOCATION: (8)
<223> OTHER INFORMATION: any amino acid
<220> FEATURE:
<221> NAME/KEY: MISC_FEATURE
<222> LOCATION: (9)
<223> OTHER INFORMATION: Ser or Thr

<400> SEQUENCE: 31

Tyr Xaa Xaa Xaa Xaa Gly Gly Xaa Xaa Gly
  1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:consensus
      sequence (linker)
<220> FEATURE:
<221> NAME/KEY: MISC_FEATURE
<222> LOCATION: (2)
<223> OTHER INFORMATION: Lys or Ser
<220> FEATURE:
<221> NAME/KEY: MISC_FEATURE
<222> LOCATION: (3)
<223> OTHER INFORMATION: any amino acid
<220> FEATURE:
<221> NAME/KEY: MISC_FEATURE
<222> LOCATION: (4)
```

```
<223> OTHER INFORMATION: Ile or Val
<220> FEATURE:
<221> NAME/KEY: MISC_FEATURE
<222> LOCATION: (5)
<223> OTHER INFORMATION: Ser or Thr
<220> FEATURE:
<221> NAME/KEY: MISC_FEATURE
<222> LOCATION: (8)
<223> OTHER INFORMATION: any amino acid
<220> FEATURE:
<221> NAME/KEY: MISC_FEATURE
<222> LOCATION: (9)
<223> OTHER INFORMATION: Ser or Thr

<400> SEQUENCE: 32

Tyr Xaa Xaa Xaa Xaa Gly Gly Xaa Xaa Gly
 1               5                  10

<210> SEQ ID NO 33
<211> LENGTH: 10
<212> TYPE: PRT
<213> ORGANISM: Rhizopus oryzae CP96001

<400> SEQUENCE: 33

Tyr Ser Ala Val Ser Gly Gly Ala Ser Gly
 1               5                  10

<210> SEQ ID NO 34
<211> LENGTH: 10
<212> TYPE: PRT
<213> ORGANISM: Rhizopus oryzae CP96001

<400> SEQUENCE: 34

Tyr Ser Ile Val Ser Gly Gly Ala Ser Gly
 1               5                  10

<210> SEQ ID NO 35
<211> LENGTH: 10
<212> TYPE: PRT
<213> ORGANISM: Mucor circinelloides CP99001

<400> SEQUENCE: 35

Tyr Lys Val Ile Ser Gly Gly Lys Ser Gly
 1               5                  10

<210> SEQ ID NO 36
<211> LENGTH: 10
<212> TYPE: PRT
<213> ORGANISM: Phycomyces nitens CP99002

<400> SEQUENCE: 36

Tyr Ser Pro Ile Ser Gly Gly Phe Ser Gly
 1               5                  10

<210> SEQ ID NO 37
<211> LENGTH: 26
<212> TYPE: PRT
<213> ORGANISM: Rhizopus oryzae CP96001

<400> SEQUENCE: 37

Ala Lys Ala Ser Thr Pro Ser Asn Ser Ser Ser Ser Ser Gly Lys
 1               5                  10                  15

Tyr Ser Ala Val Ser Gly Gly Ala Ser Gly
            20                  25

<210> SEQ ID NO 38
```

```
<211> LENGTH: 10
<212> TYPE: PRT
<213> ORGANISM: Rhizopus oryzae CP96001

<400> SEQUENCE: 38

Asn Ala Asp Asn Pro Ser Met Thr Tyr Lys
 1               5                  10

<210> SEQ ID NO 39
<211> LENGTH: 10
<212> TYPE: PRT
<213> ORGANISM: Rhizopus oryzae CP96001

<400> SEQUENCE: 39

Tyr Ser Ala Val Ser Gly Gly Ala Ser Gly
 1               5                  10

<210> SEQ ID NO 40
<211> LENGTH: 17
<212> TYPE: PRT
<213> ORGANISM: Rhizopus oryzae CP96001

<400> SEQUENCE: 40

Ser Ala Ser Asp Cys Ser Ser Leu Pro Ser Ala Leu Gln Ala Gly Cys
 1               5                  10                  15

Lys

<210> SEQ ID NO 41
<211> LENGTH: 18
<212> TYPE: PRT
<213> ORGANISM: Rhizopus oryzae CP96001

<400> SEQUENCE: 41

Tyr Gly Gly Ile Ser Ser Ala Ser Asp Cys Ser Ser Leu Pro Ser Ala
 1               5                  10                  15

Leu Gln

<210> SEQ ID NO 42
<211> LENGTH: 6
<212> TYPE: PRT
<213> ORGANISM: Rhizopus oryzae CP96001

<400> SEQUENCE: 42

Arg Phe Asn Trp Phe Lys
 1               5

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: misc_feature
<222> LOCATION: (15)..(15)
<223> OTHER INFORMATION: inosine
<220> FEATURE:
<221> NAME/KEY: misc_feature
<222> LOCATION: (18)..(18)
<223> OTHER INFORMATION: a, g, c or t

<400> SEQUENCE: 43
aaraaytgga ayggnccnac                                         20

<210> SEQ ID NO 44
```

```
<211> LENGTH: 17
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: misc_feature
<222> LOCATION: (15)
<223> OTHER INFORMATION: a, g, c, or t

<400> SEQUENCE: 44
ttraaccart traancg                                                    17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 45
ttraaccart traayct                                                    17

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 46
caatgtcttc cctctggaag cag                                             23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 47
tgcccttagt gacagcaatg ccc                                             23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 48
cttccttccg cactccaagc tgg                                             23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 49
ccagcttgga gtgcggaagg aag                                             23

<210> SEQ ID NO 50
<211> LENGTH: 23
<212> TYPE: DNA
<213> ORGANISM: Artificial Sequence
```

```
<220> FEATURE:
<223> OTHER INFORMATION: Description of Artificial Sequence:primer

<400> SEQUENCE: 50
tcactaaggg cagtgacacc atc                                          23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 51
cagagggaag acattgagag tag                                          23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 52
acaacattat ttcttcaaac atg                                          23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 53
aaatgccgca tcaagtttta ttg                                          23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 54
ttcacttcta cctctgttgc tgg                                          23

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 55
gtaataaact tcatagatct atgtaaaaag aatg                              34

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 56
ggatgagtat aaaagatctt attttcttga ac                                32
```

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 57
cactttcaga agctttattg ccac                                    24

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 58
gagctagagc cagagttaga ag                                      22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 59
gagaactgac atcggcctta cc                                      22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 60
acaacattat ttcttcgaat atg                                     23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 61
tttagcagca gaggccattt cag                                     23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 62
ttttctatcc tgatacagag atg                                     23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence:primer

```
<400> SEQUENCE: 63
gcgctcataa aacgactact acc                                             23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 64
tgcccttagt gacagcaatg tcc                                             23

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 65
caagaaaata agatcttta tactcctact                                       30

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 66
aacggcaata aggcctctga atgtagc                                         27

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 67
gaaagcaatg gccagaaaac ttctgaaag                                       29

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 68
gcttcaaact ctctagactc tagcggc                                         27

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 69
cggtaaggcc gacgtcagtt ctcc                                            24

<210> SEQ ID NO 70
<211> LENGTH: 23
```

```
<212> TYPE: DNA
<213> ORGANISM: Artificial Sequence
<220> FEATURE:
<223> OTHER INFORMATION: Description of Artificial Sequence:primer

<400> SEQUENCE: 70
tacaggagcc aacaggggag gtg                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 71
ttcacagcag gtaggtccat tcc                                              23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 72
cctacggttt cgccgctgct tcc                                              23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 73
tagataccaa caccaccacc ggg                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 74
tgaagttcct taccattgcc tcc                                              23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 75
tggtgaaacc actcgctact ggg                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 76
```
ttctgcctct gactgttcta acc                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 77
aatagagtta ctctatacga tag                              23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 78
caccaccaga gacagcggag tag                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 79
tgcgttgatt atcctgacaa tcc                              23

<210> SEQ ID NO 80
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 80
gcggatccat gaagttcctt accattgcc                        29

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 81
gcggatcctt attttcttga acagccaga                        29

<210> SEQ ID NO 82
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 82
gtggaggtga gatcttcatt gggaac                           26

<210> SEQ ID NO 83
<211> LENGTH: 24
<212> TYPE: DNA
<213> ORGANISM: Artificial Sequence -continued

```
<220> FEATURE:
<223> OTHER INFORMATION: Description of Artificial Sequence:primer

<400> SEQUENCE: 83
cagcggagta ctttgtagaa gcag                                          24

<210> SEQ ID NO 84
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 84
gggagatctt gggacaagat gaagtttatt actattg                            37

<210> SEQ ID NO 85
<211> LENGTH: 53
<212> TYPE: DNA
<213> ORGANISM: Artificial Sequence
<220> FEATURE:
<223> OTHER INFORMATION: Description of Artificial Sequence:primer

<400> SEQUENCE: 85
ggtcaaacaa gtctgtgcgg atcctgggac aagatggcca agttcttcct tac          53

<210> SEQ ID NO 86
<211> LENGTH: 132
<212> TYPE: DNA
<213> ORGANISM: Artificial Sequence
<220> FEATURE:
<223> OTHER INFORMATION: Description of Artificial Sequence:primer

<400> SEQUENCE: 86
gggggatcct gggacaagat gaagttcatc actatcgcct cctccgccct ccttgccctc   60
gcccttggca ctgagatggc ctccgccgct gagtgctcca agctctacgg ccagtgcggc  120
ggaaagaact gg                                                      132

<210> SEQ ID NO 87
<211> LENGTH: 136
<212> TYPE: DNA
<213> ORGANISM: Artificial Sequence
<220> FEATURE:
<223> OTHER INFORMATION: Description of Artificial Sequence:primer

<400> SEQUENCE: 87
ggccgactcg ctcgacttgt ttcccgagga gccgctcggc aggcactggc tgtagtagtc   60
attcgagacc ttgcaggtcg agccgctctc gcagcaggtg gggccgttcc agttctttcc  120
gccgcactgg ccgtag                                                  136

<210> SEQ ID NO 88
<211> LENGTH: 150
<212> TYPE: DNA
<213> ORGANISM: Artificial Sequence
<220> FEATURE:
<223> OTHER INFORMATION: Description of Artificial Sequence:primer

<400> SEQUENCE: 88
gggctcgagt tggacggagt cgaagccttg gcgacggtcg tggtcttctt ggcgggagcg   60
gtcgtagtct tcttgtgagc ggcggtcgtg gtcttcttgt gggcagcggt cgtggtcttc  120
ttgtgggccg actcgctcga cttgtttccc                                   150
```

<210> SEQ ID NO 89
<211> LENGTH: 158
<212> TYPE: DNA
<213> ORGANISM: Artificial Sequence
<220> FEATURE:
<223> OTHER INFORMATION: Description of Artificial Sequence:primer

<400> SEQUENCE: 89
ggaaacaagt cgagcgagtc ggcccacaag aagaccacga ccgctgccca caagaagacc    60
acgaccgccg ctcacaagaa gactacgacc gctcccgcca agaagaccac gaccgtcgcc   120
aaggcttcga ctccgtccaa ctcgagcagc tcgtcctc                           158

<210> SEQ ID NO 90
<211> LENGTH: 160
<212> TYPE: DNA
<213> ORGANISM: Artificial Sequence
<220> FEATURE:
<223> OTHER INFORMATION: Description of Artificial Sequence:primer

<400> SEQUENCE: 90
gtccttgttg caggacttga caggcgagct gacgttagcc ttgccgggcc acgagcacga    60
agccttgcag cagtcccagt agcgggtagt gacgccgttg ccgctagcgc caccgctgac   120
agcgctgtac tttcccgagg acgagctgct cgagttggac                         160

<210> SEQ ID NO 91
<211> LENGTH: 120
<212> TYPE: DNA
<213> ORGANISM: Artificial Sequence
<220> FEATURE:
<223> OTHER INFORMATION: Description of Artificial Sequence:primer

<400> SEQUENCE: 91
agcccatggc tggttgtcgt tgcacatgta ggagttgccg ccgttgcagc cggactgggc    60
gttggagtcg ctaagagcgg tgacgccgtc cttgttgcag gacttgacag gcgagctgac   120

<210> SEQ ID NO 92
<211> LENGTH: 118
<212> TYPE: DNA
<213> ORGANISM: Artificial Sequence
<220> FEATURE:
<223> OTHER INFORMATION: Description of Artificial Sequence:primer

<400> SEQUENCE: 92
ggtgagctcg aagcaggagc agcaccagcg gctctcgcca ccgccgctaa tggcagcggc    60
agcgaaaccg taagcaaggt tgtcgttgac agcccatggc tggttgtcgt tgcacatg    118

<210> SEQ ID NO 93
<211> LENGTH: 154
<212> TYPE: DNA
<213> ORGANISM: Artificial Sequence
<220> FEATURE:
<223> OTHER INFORMATION: Description of Artificial Sequence:primer

<400> SEQUENCE: 93
gtgcccactt cgatctccag atgcccggcg gcggcgtcgg catcttcaac ggatgctcgt    60
cccagtgggg cgctcccaac gacgctggg gctcgcgcta cggcggcatc agctccgcca   120
gcgactgctc gtccctcccc agcgccctcc aggc                               154

<210> SEQ ID NO 94
<211> LENGTH: 154

-continued

<210> SEQ ID NO 94
<211> LENGTH: 154
<212> TYPE: DNA
<213> ORGANISM: Artificial Sequence
<220> FEATURE:
<223> OTHER INFORMATION: Description of Artificial Sequence:primer

<400> SEQUENCE: 94 gggggatcc tgcgtttact tgcgcgagca tccggtctta gcggtgatct ccttggggca        60
ggtgacctcc ttgtaggtca tggacgggtt gtcggcgttc ttgaaccagt tgaagcgcca      120
cttgcagccg gcctggaggg cgctggggag ggac                                   154

<210> SEQ ID NO 95
<211> LENGTH: 117
<212> TYPE: DNA
<213> ORGANISM: Artificial Sequence
<220> FEATURE:
<223> OTHER INFORMATION: Description of Artificial Sequence:primer

<400> SEQUENCE: 95
ggggagctca ccttcacctc caccagcgtt gctggcaaga agatggtcgt ccaggtcacc        60
aacactggcg gtgaccttgg cagctcgacc ggtgcccact tcgatctcca gatgccc         117

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 96 gggggatcc tgcgtttact tgcgcgagca tc                                       32

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 97
tcagcggtgg cgctagcggc aac                                                23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 98
ctaatggcag cggcagcgaa acc                                                23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 99
ccggtgccca cttcgatctc cag                                                23

<210> SEQ ID NO 100
<211> LENGTH: 23
<212> TYPE: DNA

```
<213> ORGANISM: Artificial Sequence
<220> FEATURE:
<223> OTHER INFORMATION: Description of Artificial Sequence:primer

<400> SEQUENCE: 100
tctttccgcc gcactgtccg tag                                          23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 101
acgacaacca gccatgggct gtc                                          23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 102
tctcgaatga ctactacagc cag                                          23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 103
cccactggga cgagcatccg ttg                                          23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 104
cgagctgctc gagttggacg gag                                          23

<210> SEQ ID NO 105
<211> LENGTH: 16
<212> TYPE: PRT
<213> ORGANISM: Rhizopus oryzae CP96001

<400> SEQUENCE: 105

Ala Glu Cys Ser Lys Leu Tyr Gly Gln Cys Gly Gly Lys Asn Trp Asn
 1               5                  10                  15

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 106
gactgaccgg tgttcatcc                                               19
```

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 107
ctcggttgtc atagatgtgg                                              20

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 108
cccacagaag ggatccatga tggtcgc                                      27

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 109
gcgaattcat gaagttcacc gttgctatt                                    29

<210> SEQ ID NO 110
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 110
gcgaattctt actttctttc gcaacctg                                     28

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 111
cttggtgctg ccagcgttac cag                                          23

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 112
gcggatccat gaagttctcc atcatcg                                      27

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence:primer

```
<400> SEQUENCE: 113
gcggatcctt acttgcgctc gcaacca                                              27
```